US010557161B2

(12) United States Patent
Quinn et al.

(10) Patent No.: US 10,557,161 B2
(45) Date of Patent: Feb. 11, 2020

(54) RECOMBINANT HUMAN ADA2 AND ADA2 FUSION PROTEINS AND METHODS FOR TREATING ADA2 DEFICIENCIES

(71) Applicant: Alexion Pharmaceuticals, Inc., Boston, MA (US)

(72) Inventors: Anthony Quinn, Gloucester, MA (US); Zhinan Xia, Wellesley, MA (US); Markley C. Leavitt, Lexington, MA (US); Mohammed Qatanani, Needham, MA (US); Changlin Li, Athens, GA (US); Gary Kachun Yiu, Acton, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 146 days.

(21) Appl. No.: 15/527,176

(22) PCT Filed: Nov. 17, 2015

(86) PCT No.: PCT/US2015/061085
§ 371 (c)(1),
(2) Date: May 16, 2017

(87) PCT Pub. No.: WO2016/081457
PCT Pub. Date: May 26, 2016

(65) Prior Publication Data
US 2018/0201969 A1     Jul. 19, 2018

Related U.S. Application Data

(60) Provisional application No. 62/080,588, filed on Nov. 17, 2014.

(51) Int. Cl.
| | | |
|---|---|---|
| *C12P 21/02* | (2006.01) | |
| *C12N 9/78* | (2006.01) | |
| *A61K 38/50* | (2006.01) | |
| *A61K 38/51* | (2006.01) | |

(52) U.S. Cl.
CPC .............. *C12P 21/02* (2013.01); *A61K 38/50* (2013.01); *A61K 38/51* (2013.01); *C12N 9/78* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,639,052 B1 | 10/2003 | Moore |
| 8,563,803 B2 | 10/2013 | Ivarie et al. |
| 2006/0111297 A1 | 5/2006 | Roberts |

OTHER PUBLICATIONS

Martinon et al., New players driving inflammation in monogenic autoinflammatory diseases. Nat Rev Rheumatol. Jan. 2015;11(1):11-20.
Tang et al., Different subsets of macrophages in patients with new onset tuberculous pleural effusion. PLoS One. Feb. 10, 2014;9(2):e88343. 9 pages.
Sockolosky et al., Fusion of a short peptide that binds immunoglobulin G to a recombinant protein substantially increases its plasma half-life in mice. PLoS One. Jul. 24, 2014;9(7):e102566. 10 pages.
Zavialov et al., Human adenosine deaminase 2 induces differentiation of monocytes into macrophages and stimulates proliferation of T helper cells and macrophages. J Leukoc Biol. Aug. 2010;88(2):279-90.
International Search Report for Application No. PCT/US2015/061085, dated Feb. 23, 2016. 4 pages.
International Preliminary Report on Patentability for Application No. PCT/US2015/061085, dated Jun. 1, 2017. 9 pages.

*Primary Examiner* — Kagnew H Gebreyesus
(74) *Attorney, Agent, or Firm* — McCarter & English, LLP; Maria Laccotripe Zacharakis; Marcie B. Clark

(57) ABSTRACT

The present invention is directed to isolated recombinant human ADA2 proteins, ADA2 biologically active fragments, and ADA2 fusion proteins. The proteins of the invention can be surprisingly used to restore ADA2 activity in subjects having loss-of-function mutations in ADA2 and increase differentiation of monocytes into macrophages, e.g., M2 macrophages, e.g., M2c macrophages, stimulate CD4+ T cell proliferation, and increase endothelial cell development. More specifically, the ADA2 proteins, ADA2 biologically active fragments, and ADA2 fusion proteins of the invention can be used to treat subjects having ADA2-associated diseases or disorders, including but not limited to, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM.

17 Claims, 38 Drawing Sheets

Specification includes a Sequence Listing.

| Linker |
|---|
| GGGSGGGAS (SEQ ID NO: 31) |
| GGGSGGGSGGGAS (SEQ ID NO: 32) |
| SHGGGSGGGSGGGSGGGAS (SEQ ID NO: 33) |
| GGGSGGGSGGGSGGGAS (SEQ ID NO: 34) |
| GGGAS (SEQ ID NO: 35) |

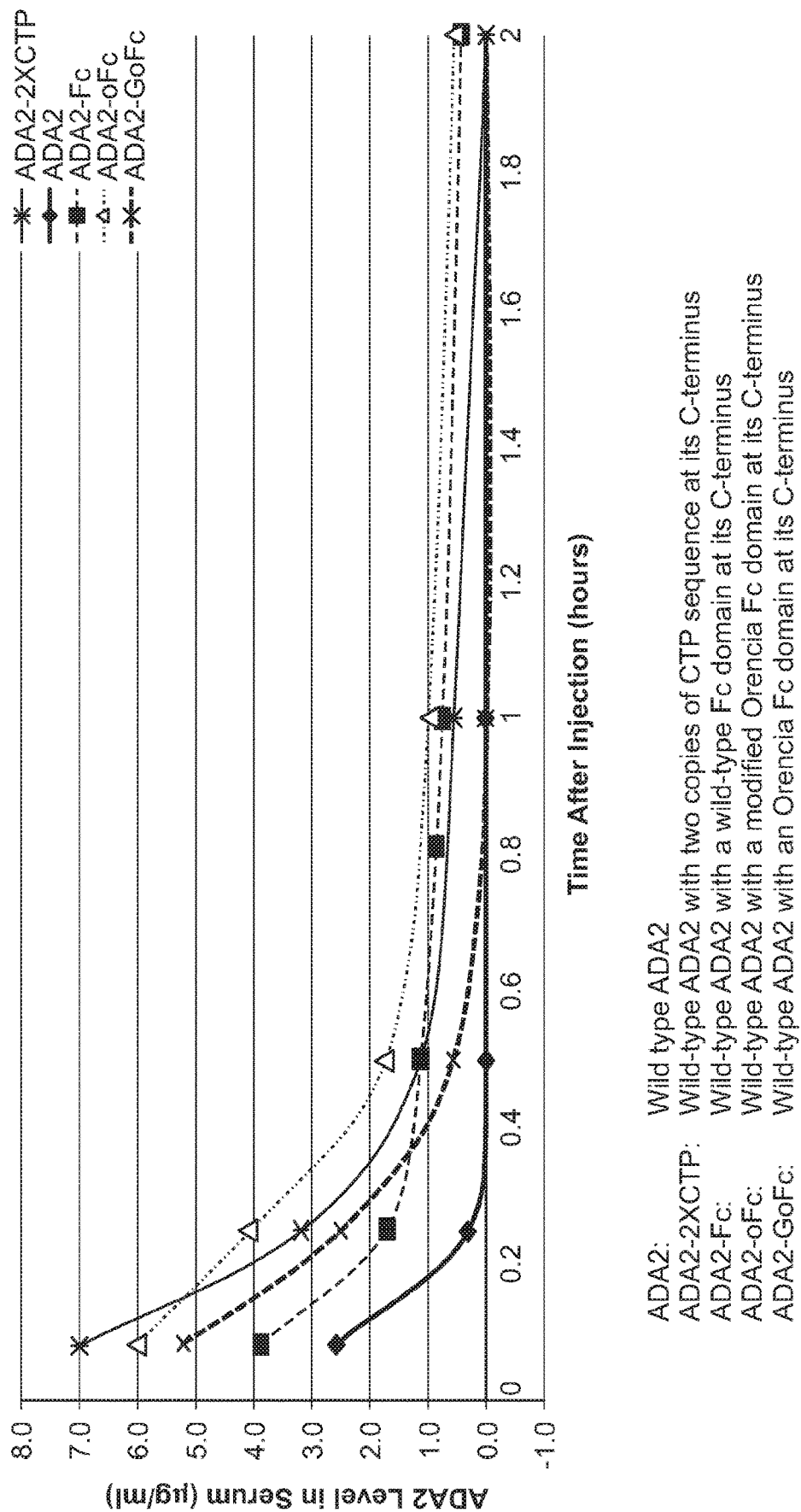

WT-293: Wild type ADA2 produced in HEK293-6E cells
N185A-293: ADA2 with a N→A mutation at amino acid position 185
WT-CHO: Wild type ADA2 produced in CHO-S cells WT-293: Wild type ADA2 produced in HEK293-6E cells
N185A-293: ADA2 with a N→A mutation at amino acid position 185
WT-CHO: Wild type ADA2 produced in CHO-S cells Rescue of cranial bleeding in 2 dpf KD zebrafish by protein injection

FIG. 25

```
  1  mlvdgpserp alcflllava msffgsalsi detrahlilk ekmmrlggrl vlntkeeian
 61  erimtikiae mkeamrtlif ppsmhffqak hliersqvfn ilrmmpkgaa ihlhdigivt
121  mdwivrnvty rphchicftp rgimgfrfah ptprpsekcs kwilledyrk rvqnvtefdd
181  slirnftlvt qhpeviytnq nvvwskfeti fftisgllhy apvfrdyvfr smqefyednv
241  lymeirarll pvyelsgehh deewsvktyq evaqkfveth pefigikily sdhrskdvav
301  iaesirmamg lrikfptvva gfdlvghedt ghsihdykea imipakdgvk ipyffhaget
361  dwggtsidrn ildalmintt righgfalsk hpavrtyswk kdipievcpi snqviklvsd
421  lrnhpvatlm atghpmviss ddpamfgakg lsydfyevfm giggmkadlr tlkqlamnsi
481  kystllesek ntfmeiwkkr wdkfiadvat k
```

(SEQ ID NO:1)

FIG. 26 atgtgttggtggatggcccatctgagcggccagccctgtgcttcttgcttgcttgtgttggctgttggcaatgtctttcttcggctc
agctctatcatagatgaaacacgggcgcatgagagcggccaatgatcgctgagatgaagagatgcggctgggggggcgctgttgc
tgaacaccaagaggagctggccaatgagagctgccacttttccaggccatgatctcgagatgacgctcaaaatcgctgagatgaagagaccc
ctgatattcccaccagcatgcctcttgcacctccatcgttccacctccaccttcattgagagaagtcaagtgtttaatattctaag
gatgatgccaaaaggggctgcccactgccacatctgtttctccacccaaggggatcatcgtcgtgactggctgtgaggaatgtca
cctacagcctcactgttccaagtggattctgctgaggattctgtcagttgctacgaacgtcactgagtttgatga
ccatcagaaaaatgttccaagtggattctcactctgtgaccctggtgaccaccccgaggtgattacacaccaaatgttgtctggtcga
cagcttgctgaggaatctctctccaccatctcggtctcatccattacgcaccagtgttcagagactgttcttccgagc
aatttgaaccatctctcttccaccatctctggtctcatccattacgcaccagtgttcagagactgttcttccgagc
atgcaggagttctacgagacaacgtgctcagtgatcatcatggagatcagagccagcaggctcagagaagtagctcagagacctgagt
agagcaccatgactgacgaagagatcaagtcagtgatcatcatggagatcagagccagcaggctcagagaagtagctcagagacctgagt
ttattggaatcaagaagtacttattcccacggtggtgatcacagatcacagatcacagaagtcatcgcagaatccatccgaatggcc
atgggctccgaatacaagggtactccatagacaggaacattctggatgctgttgaccgttaagctgtctgaaaaaggatgtgaccgttaagctgtctgaaaaaggatgtgccattga
gcatgactggcagggctacttcgactgtgcagcgtcaggaacattctggatgctgttgaacacccatagccacttcctatgactgcctgaaaacacccatagcc
cagactggcagggctacttcgactgtcagagcctggtgtcgactatgtttggtgccaaaagccttgtcctatgactgcctgaaaagccttgtcctatgactgcctgaaaagcctg
tttgcttgagcaaacacccccagtcaggactcaggacttactcctgaaaaaggacatcccatagccgtgcctctgctgaacacccatagcc
taaccaggcagggaacattctggatgcgtcagagactcagagcctggtgtcgactatgttggtgccaaaagccttgtcctatgactgcctg
tgatcagctctgatgaccctgatgacctgaggacctgaggaccctcaaacagctggccatgaactcatcaagtaactcatccaagtaacacagtaacagtaaccccctgttggagag
ggggatgaaggctgaccctgaggacctgaggacctcaaacagctggccatgaactctatcaagtaactcatccaagtaacacagtaacagtaaccccctgttggagag
tgagaaaatacttcatgaaatctgaagagagatgggataagttcatagcagatgggataagttcatagcagatggctacaaagtga (SEQ ID NO:2)

FIG. 27

```
  1  mlvdgpserp  alcflllava  msffgsalsi  detrahlilk  ekmmrlggrl  vlntkeelan
 61  erlmtlkiae  mkeamrtlif  ppsmhffqak  hliersqvfn  ilrmmpkgaa  lhlhdigivt
121  mdwlvrnvty  rphchicftp  rgimqfrfah  ptprpsekcs  kwilledyrk  rvqnvtefdd
181  silrnftlvt  qhpeviytnq  nvvwskfeti  fftisgliihy  apvfrdyvfr  smqefyednv
241  lymeirarll  pvyeisgehh  deewsvktyq  evaqkfveth  pefigikiiy  sdhrskdvav
301  iaesirmamg  lrikfptvva  gfdlvghedt  ghsihdykea  lmipakdgvk  lpyffhaget
361  dwqgtsidrn  iidalmintt  righgfalsk  hpavrtyswk  kdipievcpi  snqviklvsd
421  lrnhpvatlm  atghpmviss  Edpamfgakg  isydfyevfm  giggmkadlr  tikqlamnsi
481  kystllesek  ntfmeiwkkr  wdkfiadvat  k
```

(SEQ ID NO:11)

FIG. 28

```
  1  mlvdgpserp  alcflllava  msffgsalsi  detrahlilk  ekmmrlggrl  vlntkeelan
 61  erlmtlkiae  mkeamrtlif  ppsmhffqak  hliersqvfn  ilrmmpkgaa  lhlhdigivt
121  mdwlvrnvty  rphchicftp  rgimqfrfah  ptprpsekcs  kwilledyrk  rvqnvtefdd
181  silrnftlvt  qhpeviytnq  nvvwskfeti  fftisgliihy  apvfrdyvfr  smqefyednv
241  lymeirarll  pvyeisgehh  deewsvktyq  evaqkfveth  pefigikiiy  sdhrskdvav
301  iaesirmamg  lrikfptvva  gfdlvghedt  ghsihdykea  lmipakdgvk  lpyffhaget
361  dwqgtsidrn  iidalmintt  righgfalsk  hpavrtyswk  kdipievcpi  snqviklvsd
421  lrnhpvatlm  atghpmviss  dApamfgakg  isydfyevfm  giggmkadlr  tikqlamnsi
481  kystllesek  ntfmeiwkkr  wdkfiadvat  k
```

(SEQ ID NO:13)

FIG. 29

```
  1  mlvdgpserp alcflllava msffgsalsi detrahilik ekmmrlggrl vlntkeelan
 61  erlmtikiae mkeamrtlif ppsmhffqak hliersqvfn ilrmmpkgaa lhlhdigivt
121  mdwlvrnvty rphchicftp rgimqfrfah ptprpsekcs kwilledyrk rvqnvtefdd
181  slirnftlvt qhpeviytnq nvvwskfeti fftisgliihy apvfrdyvfr smqefyednv
241  lymeirarll pvyelsgehh deewsvktyq evaqkfveth pefigikiiy sdhrskdvav
301  iaesirmamg lrikfptvva gfdlvghedt ghslhdykea imipakdgvk lpyffhaget
361  dGggtsidrn ildalmlntt righgfalsk hpavrtyswk kdipievcpi snqvlklvsd
421  lrnhpvatlm atghpmviss ddpamfgakg lsydfyevfm giggmkadir tlkqlamnsi
481  kystliesek ntfmeiwkkr wdkfiadvat k
```

(SEQ ID NO:15)

FIG. 30

```
  1  mlvdgpserp alcflllava msffgsalsi detrahilik ekmmrlggrl vlntkeelan
 61  erlmtikiae mkeamrtlif ppsmhffqak hliersqvfn ilrmmpkgaa lQlhdigivt
121  mdwlvrnvty rphchicftp rgimqfrfah ptprpsekcs kwilledyrk rvqnvtefdd
181  slirnftlvt qhpeviytnq nvvwskfeti fftisgliihy apvfrdyvfr smqefyednv
241  lymeirarll pvyelsgehh deewsvktyq evaqkfveth pefigikiiy sdhrskdvav
301  iaesirmamg lrikfptvva gfdlvghedt ghslhdykea imipakdgvk lpyffhaget
361  dwggtsidrn ildalmlntt righgfalsk hpavrtyswk kdipievcpi snqvlklvsd
421  lrnhpvatlm atghpmviss ddpamfgakg lsydfyevfm giggmkadir tlkqlamnsi
481  kystliesek ntfmeiwkkr wdkfiadvat k
```

(SEQ ID NO:17)

FIG. 31A

ATGTTGGTGGATGGCCATCTGAGCGGCCAGCCCCTGTGCTCTTCTTGCTGTGGCAATGTCTTTCTTCGGCTC
TGCTCTATCCATAGATGAAACACGGGCGCCAATGTTGTTGAAAGAAAAGATGATGCGGCTGGTGGCTGGTGC
TGAACACCAAGGAGGAGCTGCCAATGCACTTTTTCCAGGCCATCTCTTCATTGAGAGAAGTCAAGTGCTGAGGACC
CTGATATTCCACCCAGCCAAGCATTGCCCTCCATGACATTGGCCATCTATGGACTGGCTGGTGAGGAATGTCA
GATGATGCCAAAGGGCTGCCACATCTGTTTCACCCTGACCATCATGAAGGGGGATTATCGGAGTTCAGATTTGCTGCCAACTCCCGT
CCTACAGGCCTCACTGCCTCCAAGTTCCAAGTTGGATTCTGCTGGAGGATTATCGGAGTGCAGAACGTCACTGAGTTTGATGA
CCATCAGAGAAAAATGTTCCAAGTTGGATTCTGCTGAGCCCAGCACCCTCATCATGGAAGCCAAAATGTTGTCTGGTCGA
CAGCTTGCTGAGGAATTTCACTCTGGTGACCCCAGCTCTCTGTCTGATACACAAAATGTTGTCTGGTCGA
AATTTGAAACCATCTGCCTACGAGGACAACGTGCTCAGTCGAGATCAGAGCCAGCTAGCTCAGAAGTTTGTGGAAACTCATCCTGAGT
ATGCAGGAGTTCTACGAGGACAACGTGCTCAGTCGAGATCAGAGCCAGCTAGCTCAGAAGTTTGTGGAAACTCATCCTGAGT
AGAGCACCATGACGAAGAGTGGTCAGTGAAGACTTATCAGGAAGTAGCTCAGAAGTTTGTGGAAACTCATCCTGAGT
TTATTGGAATCAAAATCATTTATTCGGATCACAGATCAAAGATGTGGCTGCCTTAAGCTCGTTAACTGCCTTGGGCATCGGCCTCCTT
ATGGGGCTCCGAATCAAGTTCCCCAGCTTCTGATGATCCCCGCCAAGGATGCCAGGGTTTGACCTGGCAGGGTTGCCATGAGGACATTCGGCCATGGA
GCATGACTACAAGGAAGCTACTTCACACCCGTGTCTTGGATGTCTTGAGGAACATTCTGGAAAAAGGACATCCTGTAGCTTACTTCTTCCAGAATGCTGTCCTACACACTGGCTCATCTC
CAGACTGGCAGGAAGCTGGAGCTACTTCACACCCGTGTCTTGGATGTCTTGAGGAACATTCTGAGGTTCTGAACTGGAACACTACCAGAATCTGTGTCCTACTCTCATCTC
TTTGCTTTGAGCAAATCAGGTCAGGACTTATTCCTGGAAAAAGGACCCTGTAGCAACAGCTGGCCAATGGGCAATGGATAAGCTTCATCAACACGAATGCTGTCCCATGGCATT
TAACCAGTGCTGAAATGGTGCTGAAACCCTGTAGCAACAGCTGGCCATGATGGATAAGCTTCATCAGCAGATGTGGCTACAGTGGCTACCCCTGTTGGAGAG
TGATCAGCCTGATGACCAGCTATGTTTGTGCCAAAGCTGGCCATGATGGATAAGCTTCATCAGCAGATGTGGCTACAGTGGCTACCCCTGTTGGAGAG
GGGGGATGAAGGCTGAACTGAGGAAATACACATGCCCCAGACCCGTGCCCGATCTCCCAGATGCACATGCCCAGCAGAGATGCTGGAGGCTCATTAGCTCATCAGATGAGCCCA
TGAGAAAAATACTTTCATGAATGCCCAGACCCGTGCCCGATCTCCCAGATGCACATGCCCAGCAGAGATGCTGGAGGCTCATTCATCAGATGAGCCACGA
AATCTTGTGACAAACCAGGTCAAGTTCAACCTGTGTTCACCGTGTACGTCAGCGTGGAGGTGCATAATGCCAAGACAAAGCCGCGGAGGAGCACGA
CCCCAAACCCTGAGGTCAAGTTCAACTGGTACGTGGACGGCGTGGAGGTGCATAATGCCAAGACAAAGCCGCGGAGGAGCACGA
AGACCCTGAGGTCAAGTTCAACTGGTACGTGGACGGCGTGGAGGTGCATAATGCCAAGACAAAGCCGCGGAGGAGCAAG
AGTACAACAGCACGTACCGTGTGGTCAGCGTCCTCACCGTCCTGCACCAGGACTGGCTGAATGGCAAGGAGTACAAGTG
TCTATCCAAGGTGTACACCCTGCCCCCATCCCGGGAGGAGATGACCAAGAACCAGGTCAGCCTGACCTGCCTGGTCAAAGGCT
ACAGGTGTACACCCTGCCCCCATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCTCCCTGTCCCCGGGTAAATGA (SEQ ID NO:20)

FIG. 31B

MLVDGPSERPALCFLLLAVAMSFFGSALSIDETRAHLLLKEKMMRLGGRLVLNTKEELANERLMTLKIAEMKEAMRT
LIFPPSMHFFQAKHLIERSQVENILRMMPKGAALHLHDIGIVTMDWLVRNVTYRPHCHICFTPRGIMQFRFAHPTPR
PSEKCSKWILLEDYRKRVQNVTEFDDSLLRNFTLVTQHPEVIYTNQNVVWSKFETIFFTISGLIHYAPVFRDYVFRS
MQEFYEDNVLYMEIRARLLPVYELSGEHHDEEWSVKTYQEVAQKFVETHPEFIGIKIIYSDHRSKDVAVIAESIRMA
MGLRIKFPTVVAGFDLVGHEDTGHSLHDYKEALMIPAKDGVKLPYFFHAGETDWQGTSIDRNILDALMLNTTRIGHG
FALSKHPAVRTYSWKKDIPIEVCPISNQVLKLVSDLRNHPVATLMATGHPMVISSDDPAMFGAKGLSYDFYEVFMGI
GGMKADLRTLKQLAMNSIKYSTLLESEKNTFMEIWKKRWDKFIADVATKEPKSCDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO:19)

FIG. 32A

ATGTTGGTGGATGGCCCATCTGAGCGGCCAGCCCTGTGCTCTTCTTGCTGTTGGCTGTGTGGCAATGTCTTTCTTCGGCTC
TGCTCTATCCATAGATGAAACACGGGCGGCGCATCTGTTGTTGAAAGAAAAGATGATGCGGCTGGGGGCGGCTGGTGC
TGAACACCAAGGAGGAGCCCCAATGAGAGGCTCAAATCGCTGAGATGAAGAGGCCATGAGGACC
CTGATATTCCCACCCAGCACTTTTCCAGGCCAAGCATTGAGAGAAGTCAAGTGTTTAATATTCTAAG
GATGATGCCAAAAGGGGCTGCCTTGCACCTCCATGACATTGGCATGGACTGGCTGGTGAGGAATGTCA
CCTACAGGCCTCACTGCCACATCTGTTTCACCCCAAGGGGATCATGCAGTTCAGATTTGCTCAACTCCCGT
CCATCAGAGAAAATGTTCAAGTGATTCTGCTGGAGGTTATCGGAGGTGCAGAAGCGGGTTACACAACGTCACTGAGTTTGATGA
CAGCTTGCTGAGGAATTTCACTGCTGTGACCCAGCCTCTCATGGAGCGGATTACCATTACGCCAGTGCTGTTCACAAATGTTGTCTGTCGA
AATTTGAAACCATCTCTTCTACGAGGACAACGTGCTCTACATGGAGATCAGAGGCCAGGCTCAGAGAAGTAGCTCAGAAGTTTGTGGAAATCCGAATGCC
ATGCAGGAGTTCTACGAGGACAACGTGCTCTACATGGAGATCAGAGGCCAGGCTCAGAAGTAGCTCAGAAGTTTGTGGAAATCCGAATGCC
AGAGCCATGACGAAGAGTGGTTCAGTGAAGACTTATCAGGAAGTAGCTCAGATGTGGCTGTCTGTGGGCATGAGAGACACTGGCCACTCCTT
TTATTGGAATCAAATCATTATTCGATCACAGATCAAAAGATGCCAAAGTTTGACCGTGGTGGCCAAGGTTTGACCGTGGTGGCCAAGG
ATGGGCTCCGAATCAAGTTCCCCACGTGGTTGACCGTGGTGGCCAAGGTTTGACCGTGGTTAAGCGCGTTAAGCTGCGTTAAGCGGATG
GCATGACTACAAGGAAGCTCTTCCATAGACAGGAACATTCTGGATGCTGAACATCCCATTCCCATGATGAGATCTGCCATCTC
CAGACTGGCAGGTACTTTCAGCACCCCGCAGTCTGGACTTGAGGAACCACTCTGAGCCACTCTGATGGCCATCCGCCATGG
TTTGCTTTGAGCAAACACCCGCAAATCTGAAATCTGATGCAGTCTGGAACTGGTGAGGAAACCACTCTGAGCCACTCTGATGG
TAACCAGGTGCTGAACTGGTGAGGAAATCTGGGTGCCAAGATCAGAGAGAGAGAGAGAGAGAGAGAGAGAGAGAGAGAGAG
TGATCAGCTGATGACCCAGCTATGTTTGGTGCCAAACAGCTGGCCATGGGATAAGTTCATAGCAGATGGCTACAAAGGAGCCA
GGGGGATGAAGGCTGATCTGAGGACCCTCAAACAGCTGGCCATGGGATAAGTTCATAGCAGATGGCTACAAAGGAGCCA
TGAGAAAAAATACTTTCATGAAATGCAACACATGTCCCCTGGTCCTAGCCAGAACCCCAGGATCCAGGTGTTTCTTC
AATCCTCCTAAGCCAAGTGCACATGAACAGACACATGTCAACTGGTGAGCCTGAGGTCCACTCGGTGTGTCGACTGTCGACGA
CCTGGAGCCCGAAGTGAAGTTCAACGTTCAACTGGTGAGCCTGAGGTCCTCCCATCAGGACCATCTCCAAAGAACCAGGAGACTACAAA
GGACCCCGAAGTGAAGTTCAACGTTCAACTGGTGAGCCTGAGGTCCTCCCATCAGGACCATCTCCAAAGAACCAGGAGACTACAAA
AGTACACAGCAGTGAAGCACATAAGCCCCTCCCTGCCAGAGAACGAGTCCCAATGCAGCTCAATGCAGCTCAGCAGACCTGTGTGAAGGAT
TGCAAGGTCTATACCCTTCCGACATTGCCCTCCTTCTCCGTGTACTCCAAGCCTGCTCCCCACCACACCACCACCCCTGTC
CCAGGTCTATACCCTTCCGACATTGCCCTCCTTCTCCGTGTACTCCAAGCCTGCTCCCCACCACACCACCACCCCTGTC
TCTACCCTTCCGACTCCGACTCCGTGTACTCCAAGCCTGCTCCCCACCACACCACCACCCCTGTC
CTCGACTCCGTCCGTCATGCAGCTCCTGCATGGAGGCCCCTCCCACAACCACTACACACAGAAGTCCCCTCTGAGCCCGGCAAGTCTT
CAGCTGCTCCGTCATGCAGCTCCTGCATGGAGGCCCCTCCCACAACCACTACACACAGAAGTCCCCTCTGAGCCCGGCAAGTGA (SEQ ID NO:22)

FIG. 32B

MLVDGPSERPALCFLLLAVAMSFFGSALSIDETRAHLLLKEKMMRLGGRLVLNTKEELANERLMTLKIAEMKEAMRT
LIFPPSMHFFQAKHLIERSQVFNILRMMPKGAALHLHDIGIVTMDWLVRNVTYRPHCHICFTPRGIMQFRFAHPTPR
PSEKCSKWILLEDYRKRVQNVTEFDDSLLRNFTLVTQHPEVIYTNQNVVWSKFETIFFTISGLIHYAPVFRDYVFRS
MQEFYEDNVLYMEIRARLLPVYELSGEHHDEEWSVKTYQEVAQKFVETHPEFIGIKIIYSDHRSKDVAVIAESIRMA
MGLRIKFPTVVAGFDLVGHEDTGHSLHDYKEALMIPAKDGVKLPYFFHAGETDWQTSIDRNILDALMLNTTRIGHG
FALSKHPAVRTYSWKKDIPIEVCPISNQVLKLVSDLRNHPVATLMATGHPMVISSDDPAMFGAKGLSYDFYEVFMGI
GGMKADLRTLKQLAMNSIKYSTLLESEKNTFMEIWKKRWDKFIADVATKEPKSSDKTHTCPPCPAPEAAGGSSVLF
PPKPKDTLMISRTPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO:21)

FIG. 33A

ATGTTGGTGGATGGCCATCTGAGCGGCCAGCCCTGTGCTTCTTGCTGTTGGCTGTGTGGCAATGTCTTTCTTCGCTC
TGCTCTATCGATGAAACACGGGCGCATCTGTTGTTGAAAGAAAAGATGATGCGGCCTGTGGTGC
TGAACACCAAGGAGGAGCTGGCCAATGAGAGGCTCATGACGCTCAAAATCGCTGAGATGAAGTCAAGTGAGGACC
CTGATATATTCCACCCAGCATGCACTTTTTCCAGGCCAAGCATCTCATTGAGAGAAGTCAAGTGTTTAATATTCTAAG
GATGATGCCAAAAGGGGCTGCCTTGCCACATCTGTTTCACCCAAGGGGATCATGACATTGGCATGACTGGCTGTGAGGAATGTCA
CCTACAGGCCCTCACTGCCACATCTGTTTCACCCAAGGGGATCATGCAGTTCAGATTTGCTCACCCAACTCCCCGT
CCATCAGAGAAAAATGTTCCAAGTGGAATTCTGCTGACCCAGCACCCGGAAGCTGCAGAACGTCACTGAGTTTGATGA
AATTTGAAACCATCTCTTCACCATCTCTGGTGACCCAGCACCCGGAGGTGATTTACACAACAAAATGTTGTCTTCCGAGAGC
ATGCAGGAGTTCTACGAGGACAACGTGTCAGTGGTCAGTAGCTCAGAGAGTCCAGGCCAGCTCTGCCGGTGTATGACTCAGTGG
AGAGCACCATGACGAAGAGTGGTCAGTGAAGACTTATCAGGAAGTAGCTCAGAAGTTTGTGCGAGAATCCATCCGAATGGCC
TTATTGGAATCAAAATCATTTATTCCGATCACAGATCCAAAGATGTGGCTGTCTGTGGGCATGGAGGACACTGGCCACTCCTT
ATGGGGCTCCGAATCAAGTTCCCCACGGTGGTGCAGGGTTTGACCTGGTGCAGGATGGCGTTAAGCTGCCTTACTTCTTCCACGCCGGAGAAA
GCATGACTACAAGGAAGCTCTGATGATCCCCGCAGAAGCATTCTGGATGCTCTGATGCTGAACACTACCAGAATCGGCATGGA
CAGACTGGCAGGTACTTCCATAGACACCCCGCAGTCAGGACTTAATCCTGAAAAAGGAACATCCCTCGTCCTATCTC
TTTGCTTTGAGCAAACACCCTGAAACTGGCCTTGTGTGTGCCAAACAGCTGGCCATGAATCCCCAAAGCTGGCCACTGG
TAACCAGGTGCTGAAACTGGCCTTGCTTGACTTTGAGGAACCACCACTCTGTAGCCACTCTGATGGCCACTCGATGAGGATGGG
TGATCAGCCTCTGATGACCAGCACCCCAGTCAGCTGTAGAGAAATGTTCTATAGCAGATGTGGCTACAAGTCCTCTT
GGGGGATGAAAATACTTTCATGGAAATATGGAAGAGAGATGGGATAAGTTCATAGCAGATGTGGCTACAAGTCCTCTT
CCTCAAAGGCACCCTCCACTTCCAAGCTCCCCCCTACCCTTCGAGACCCATCCGGACTGGCCTACCCTGTTGGAGAG
CCTCAAAGGCACCCTCCACTTCCAAGCTCCCCCTACCCTCTCCTTCGCGTCCCCTTCCGATACACCAATTCT
ACCCCAGTGA (SEQ ID NO:24)

FIG. 33B

MLVDGPSERPALCFLLLAVAMSFFGSALSIDETRAHLLLKEKMMRLGGRLVLNTKEELANERLMTLKIAEMKEAMRT
LIFPPSMHFFQAKHLIERSQVFNILRMMPKGAALHLHDIGIVTMDWLVRNVTYRPHCHICFTPRGIMQFRFAHPTPR
PSEKCSKWILLEDYRKRVQNVTEFDDSLLRNFTLVTQHPEVIYTNQNVVWSKFETIFFTISGLIHYAPVERDYVERS
MQEFYEDNVLYMEIRARLLPVYELSGEHHDEEWSVKTYQEVAQKFVETHPEFIGIKIIYSDHRSKDVAVIAESIRMA
MGLRIKFPTVVAGFDLVGHEDTGHSLHDYKEALMIPAKDGVKLPYFFHAGETDWQGTSIDRNILDAIMLNTTRIGHG
FALSKHPAVRTYSWKKDIPIEVCPISNQVLKLVSDLRNHPVATLMATGHPMVISSDDPAMFGAKGLSYDFYEVFMGI
GGMKADLRTLKQLAMNSIKYSTLLESEKNTFMEIWKKRWDKFIADVATKSSSSKAPPPSLPSPSRLPGPSDTPILPQ
SSSSKAPPPSLPSPSRLPGPSDTPILPQ (SEQ ID NO:23)

FIG. 34

ATGTTGGTGGATGGCCCATCTGAGCGGCCAGCCCCTGTGCTTCTTGCTGTTGGCAATGTCTCTTTCTTCGCTC
TGCTCTATCCATAGATGAAACACGGGCCGCCATCTGTTGTTGAAAGATGATGCGGCCTGGGGGGCGGCTGTGC
TGAACACCAAGGAGGAGCTGGCCAATGAGAGGCTCATGACGCTCAAATCGCTGAGATGAAGGAGGCCATGAGGACC
CTGATATTCCCACCCAGCATGCACTTTTGCACCTCCAGGCCAAGCATCTCATTGAGAGAAGTGTTTAATATTCTAAG
GATGATGCCAAAAGGGGCTGCCCTTGCCACATCGTGTTCAGGGGGATCATGACCAGTTCAGATTTGCTCATGGACTGGCTGGTGAGGAATGTCA
CCTACAGGCCCTCACTGCCACATCTGTTTCAAGTGGATTCTGGTGAGGACCACCCGGAGGATTATCGGAGGTGATTTACACAAACCAAAATGTTGTCTGGTCGA
CAGCTTGCTGAGGAAATTGTTCAAGTGGATTCTGGTGAGGACCACCCGGAGGATTATCGGAGGTGATTATCGGAGGTGATTTGATGA
AATTTGAAACCATCTCTTCTTCACGAGGACAACGTGCTCTACAGACTTATCAGAGACTATGTCTTCCGGAGC
ATGCAGGAGTTCTACGAGGAAGAGTGGTCAGTGAAGATCAGAGCCAGGCTGTCGCCGGTGTATGAACTCATCCTGAGT
AGAGCACCATGAATCAAAATCATTTATTCGGATCACAGATCCAAAAGATGTGCCTGTCATCGCCAGAATCCATCCGAATGGCC
TTATTGGAATCAAGAATCATTTATTCGGATCACAGATCCAAAAGATGTGCCTGTCATCGCCAGAATCCATCCGAATGGCC
ATGGGGCTCCGAATCAAGTTCCCCACGGTTGGTGGCAGGGTTTGACCTGGGCATGAGGAGACACTGGCCACTCCTT
GCATGACTACAAGGAAGCTCTGATGATCCCCAAGGATGCGGTTAAGCTGATGCTGATGCTGAACACTACTTCTTCCACGCCGGAGAAA
CAGACTGGCAGGGTACTTCCATAGAACACCCCGCAGTCAGGACTTACTTCGGATGCTGAAAAAGGACATCCCATAGAAGTCTGTCCCATCTC
TTTGCTTTGAGCAAACACCCCGCAGTCTGACTTTGAGGAACCACCACTCTGAGTTCCTATGAGTGCAGTACGAGTTCATGGCATT
TAACCAGGTGCTCTGAAACTGTGTCTGACCAGCTATGTTTGTGCCCCTCAAAACAGCTGGCCATGAACTCTATCAACTCAGTACCCTGTTGGAGAG
TGATCAGCTCTGATGACGAAGGCTGATCTGAGGACCCTCAAAACAGCTGGCCATGAACTCTATCAACTCAGTACCCTGTTGGAGAG
GGGGGATGAAGGCTGATCTGAGGACCCTCAAAACAGCTGGCCATGAACTCTATCAACTCAGTACCCTGTTGGAGAG
TGAGAAAAATACTTTCATGGAAATATGGAAGAAGATGGGATAAGTTCATAGCAGATGTGGCTACAAAGTGA (SEQ ID NO:36)

RECOMBINANT HUMAN ADA2 AND ADA2 FUSION PROTEINS AND METHODS FOR TREATING ADA2 DEFICIENCIES

RELATED APPLICATIONS

This application is a 35 U.S.C. § 371 national stage filing of International Application No. PCT/US2015/061085, filed on Nov. 17, 2015, which in turn claims priority to U.S. Provisional Application No. 62/080,588, filed on Nov. 17, 2014. The entire contents of each of the foregoing applications are expressly incorporated herein by reference.

SEQUENCE LISTING

The instant application contains a Sequence Listing which has been submitted electronically in ASCII format and is hereby incorporated by reference in its entirety. Said ASCII copy, created on Jan. 6, 2018, is named 2018-01-06_121424-03603_ST25.txt and is 105,396 bytes in size.

BACKGROUND OF THE INVENTION

Two types of adenosine deaminases exist in humans: ADA1 and ADA2. The primary role of ADA1, which acts as a monomer, is to eliminate intracellular toxic derivatives of adenosine and deoxyadenosine and to protect the cells from apoptosis (see, e.g., Franco et al., 2007, Crit. Rev. Immunol, 27:495-509 and Niisu et al., 1998, Blood, 92:3368-3375). The absence of ADA1 due to genetic mutations results in severe combined immunodeficiency (SCID) (see, e.g., Hershfield, 2005, Eur. J. Immunol., 35:25-30).

ADA2 (Adenosine Deaminase 2), also known as Cat Eye Syndrome Chromosome Region, Candidate 1, or CECR1, is an adenosine deaminase that catalyzes the deamination of adenosine and 2-prime-deoxyadenosine to inosine and deoxyinosine, respectively. In contrast to ADA1, ADA2 is a secreted homodimer and is highly expressed in plasma. ADA2 is highly expressed in dendritic cells, CD14+ monocytes, and lymphoid tissues, particularly in the thymus.

Recently, several groups have discovered that recessive loss-of-function mutations in CECR1, the gene encoding ADA2, can cause early-onset stroke and polyarteritis nodosa vasculopathy with highly varied clinical expression (Elkan et al., 2014, N. Engl. J. Med., 370(10):921-931 and Zhou et al., 2014, N. Engl. J. Med., 370(10):911-920). These loss-of-function mutations in humans reflect both impairment of the catalytic activity of ADA2 and the loss of its growth factor activities (see, Elkan et al., 2014). Current therapeutic options for ADA2-associated diseases and disorders are limited to management of symptoms using corticosteroid drugs or anti-TNF therapeutics. Thus, there exists a dire need to provide therapy for treating the root cause of the ADA2-associated diseases stemming from ADA2 deficiency by providing recombinant human ADA2 to patients and normalizing immunological signaling and cellular differentiation processes.

SUMMARY OF THE INVENTION

The present invention relates to isolated recombinant human ADA2 proteins or ADA2 fusion proteins and uses of thereof in the treatment of ADA2-associated diseases and disorders. The proteins of the invention can be surprisingly used to restore ADA2 activity in subjects having loss-of-function mutations in ADA2 and can increase differentiation of monocytes into macrophages, e.g., M2 macrophages, e.g., M2a macrophages, M2b macrophages or M2c macrophages, stimulate CD4+ T cell proliferation, and increase endothelial cell development. More specifically, the ADA2 proteins and ADA2 fusion proteins of the invention can be used to treat subjects having ADA2-associated diseases or disorders, including but not limited to, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM.

In one aspect, the invention provides a pharmaceutical composition comprising an isolated human ADA2 protein, or biologically active fragment thereof, and a pharmaceutically acceptable carrier, wherein the ADA2 protein, or biologically active fragment thereof, increases differentiation of monocytes into M2 macrophages. In one embodiment, the ADA2 protein comprises SEQ ID NO: 1, or a functional peptide having at least 95%, 96%, 97%, 98%, or 99% sequence identity to SEQ ID NO:1. In one embodiment, the ADA2 protein comprises SEQ ID NO: 1, or a protein having at least 95%, 96%, 97%, 98%, or 99% sequence identity to SEQ ID NO:1 and that retains the biological activity of wild-type ADA2. In another embodiment, the biologically active fragment comprises an adenosine deaminase domain of human ADA2. In one embodiment, the M2 macrophages are M2a and/or M2c macrophages that express CD163. In one embodiment, the M2 macrophages are M2c macrophages that express CD163.

In another aspect, the invention provides a fusion protein comprising an isolated human ADA2 protein, or biologically active fragment thereof, and a protein that increases the half-life of the fusion protein. In one embodiment, the protein that increases the half-life of the fusion protein comprises an Fc domain of IgG. In one embodiment, the protein that increases the half-life of the fusion protein comprises at least one CTP molecule. In one embodiment, the protein that increases the half-life of the fusion protein comprises two CTP molecules. In one embodiment, the protein that increases the half-life of the fusion protein comprises a CTP and an Fc domain of an IgG.

In one embodiment, the protein that increases the half-life is fused to the C-terminus of the ADA2 protein. In another embodiment, the protein that increases the half-life is fused to the N-terminus of the ADA2 protein.

In one embodiment, the protein that increases the half-life is fused to the ADA2 protein using a peptide linker. In one embodiment, the fusion protein has an amino acid sequence that is at least 75% identical to SEQ ID NO:19, SEQ ID NO:21, SEQ ID NO:23, or SEQ ID NO:25.

In one embodiment, the ADA2 fusion protein forms a homodimer.

In one embodiment, the invention includes ADA2 proteins that increase the half-life of the ADA2 protein. In one embodiment, one or more asparagine is substituted with a different amino acid to remove known or predicted N-glycosylation sites in the ADA2. In one embodiment, one or more asparagine is substituted with an alanine to remove a known or predicted N-glycosylation site in ADA2. In one embodiment, one or more asparagine is substituted with an alanine at position 127 of SEQ ID NO: 1. In one embodiment, one or more asparagine is substituted with an alanine at position 174 of SEQ ID NO: 1. In one embodiment, one or more asparagine is substituted with an alanine at position 185 of SEQ ID NO: 1. In one embodiment, one or more asparagine is substituted with an alanine at position 378 of SEQ ID NO: 1. In some embodiments, the ADA2 variant is ADA2-N127A (SEQ ID NO: 3), ADA2-N174A (SEQ ID NO: 5), ADA2-N185A (SEQ ID NO: 7), or ADA2-N378A (SEQ ID NO: 9).

In another aspect, the invention provides a nucleic acid encoding an ADA2 protein or an ADA2 fusion protein of the invention.

In another aspect, the invention provides a vector comprising a nucleic acid encoding an ADA2 protein or an ADA2 fusion protein of the invention.

In another aspect, the invention provides a host cell comprising a vector comprising the nucleic acid encoding an ADA2 protein or an ADA2 fusion protein of the invention.

In another embodiment, the invention provides a pharmaceutical composition comprising an ADA2 fusion protein of the invention.

In another aspect, the invention provides a method of producing a fusion protein comprising an isolated human ADA2 protein and a protein that increases the half-life of the fusion protein comprising culturing a host cell described herein under conditions permitting the production of the fusion protein. In one embodiment, the method further comprises recovering the protein.

In another aspect, the invention provides a method of producing an isolated human ADA2 protein comprising expressing the human ADA2 protein in an oviduct cell of an avian, and isolating the human ADA2 protein from egg white of an egg produced by the avian. In one embodiment, the avian comprises a transgene which includes a retroviral vector comprising a human ADA2 nucleic acid sequence operably linked to a promoter such that the avian expresses the human ADA2 nucleic acid in the oviduct cell of an avian.

In another aspect, the invention provides a method of producing an isolated human ADA2 fusion protein comprising expressing the ADA2 fusion protein in an oviduct cell of an avian, and isolating the ADA2 fusion protein from egg white of an egg produced by the avian.

In another aspect, the invention provides methods of treating a subject having an ADA2-associated disease or disorder, the method comprising administering to the subject the pharmaceutical compositions of the invention. In one embodiment, the ADA2-associated disease or disorder is a disease or disorder selected from the group consisting of polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, low serum IgM, microscopic polyangitis, Wegener's granulamatosis, Churg-Strauss syndrome, Takayasu arteritis, giant cell arteritis, Livedoid vasculopathy and small vessel vasculitis. In one embodiment, the ADA2-associated disease or disorder is polyarteritis nodosa (PAN). In one embodiment, the subject is a human.

In another aspect, the invention provides a method of increasing the differentiation of monocytes into M2 macrophages in a subject, the method comprising administering to the subject a pharmaceutical composition of the invention. In one embodiment, the subject has an ADA2-associated disease or disorder. In another embodiment, the ADA2-associated disease or disorder is a disease or disorder selected from the group consisting of polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, low serum IgM, microscopic polyangitis, Wegener's granulamatosis, Churg-Strauss syndrome, Takayasu arteritis, giant cell arteritis, Livedoid vasculopathy and small vessel vasculitis. In one embodiment, the subject is a human. In one embodiment, the M2 macrophages are M2c macrophages that express CD163.

Other features and advantages of the invention will be apparent from the following detailed description and claims.

BRIEF DESCRIPTION OF THE DRAWINGS

FIGS. 9A and 9B depict the results of pharmacokinetic studies of wild-type ADA2 and ADA2 fusion proteins in Sprague Dawley rats. FIG. 9A shows protein levels in serum over the course of about 24 hours after injection. FIG. 9B shows the same data over the course of 8 hours after injection.

FIG. 11A shows protein levels in serum over the course of about 24 hours after injection. FIG. 11B shows the same data over the course of 4 hours after injection.

FIG. 20 demonstrates that PMA significantly increased the expression of CD206 in U937 cells transduced with control shRNA.

FIG. 21 depicts that PMA-induced CD206/CD163 expression is increased with ADA2 in U937 cells transduced with CECR1 shRNA.

FIG. 22 depicts that PMA-induced CD163 expression is increased with ADA2 in U937 cells transduced with CECR1 shRNA.

FIG. 23A shows the percentage of fish illustrating cranial bleeding after injection with siRNAs against the ADA2 gene (cerc1b), followed by injection of recombinant wild-type ADA2 protein or fish water control. FIG. 23B shows the same data normalized to the knockdown of the ADA2 gene.

FIG. 25 depicts an amino acid sequence of a wild-type human ADA2 protein (SEQ ID NO: 1).

FIG. 26 depicts the nucleotide sequence of a wild-type human ADA2 nucleic acid (SEQ ID NO: 2).

FIG. 27 depicts the amino acid sequence of ADA2-D441E (SEQ ID NO:11), an ADA2 mutant with missense point mutations in the ADA2 active site (catalytic domain).

FIG. 28 depicts the amino acid sequence of ADA2-D442A (SEQ ID NO:13), an ADA2 mutant with missense point mutations in the ADA2 active site (catalytic domain).

FIG. 29 depicts the amino acid sequence of ADA2-W362G (SEQ ID NO:15), an ADA2 mutant with a missense point mutation important for intersubunit interactions of ADA2 (dimerization formation).

FIG. 30 depicts the amino acid sequence of ADA2-H112Q (SEQ ID NO:17), an ADA2 mutant with mis sense point mutations in the ADA2 active site (Zn' binding domain).

FIGS. 31A and 31B depict the nucleotide sequence of ADA2-wFC (SEQ ID NO:20) and the protein sequence of ADA2-wFC (SEQ ID NO:19), respectively. The boxed nucleotides denote nucleotide differences between this coding region and that of the NCBI sequence of wild-type CECR1 transcript variant 3 (NM_001282225.1). The protein sequence encoded by the degenerate CECR1 (ADA2) nucleic acid sequence is identical to the wild-type ADA2 protein (e.g., SEQ ID NO:1) due to degeneracy of the code. The wild-type Fc sequence is underlined.

FIGS. 32A and 32B depict the nucleotide sequence of ADA2-oFc (SEQ ID NO:22) and the protein sequence of ADA2-oFc (SEQ ID NO:21), respectively. The boxed nucleotides denote nucleotide differences between this coding region and that of the NCBI sequence of wild-type CECR1 (ADA2) transcript variant 3 (NM_001282225.1).

Figure 1:
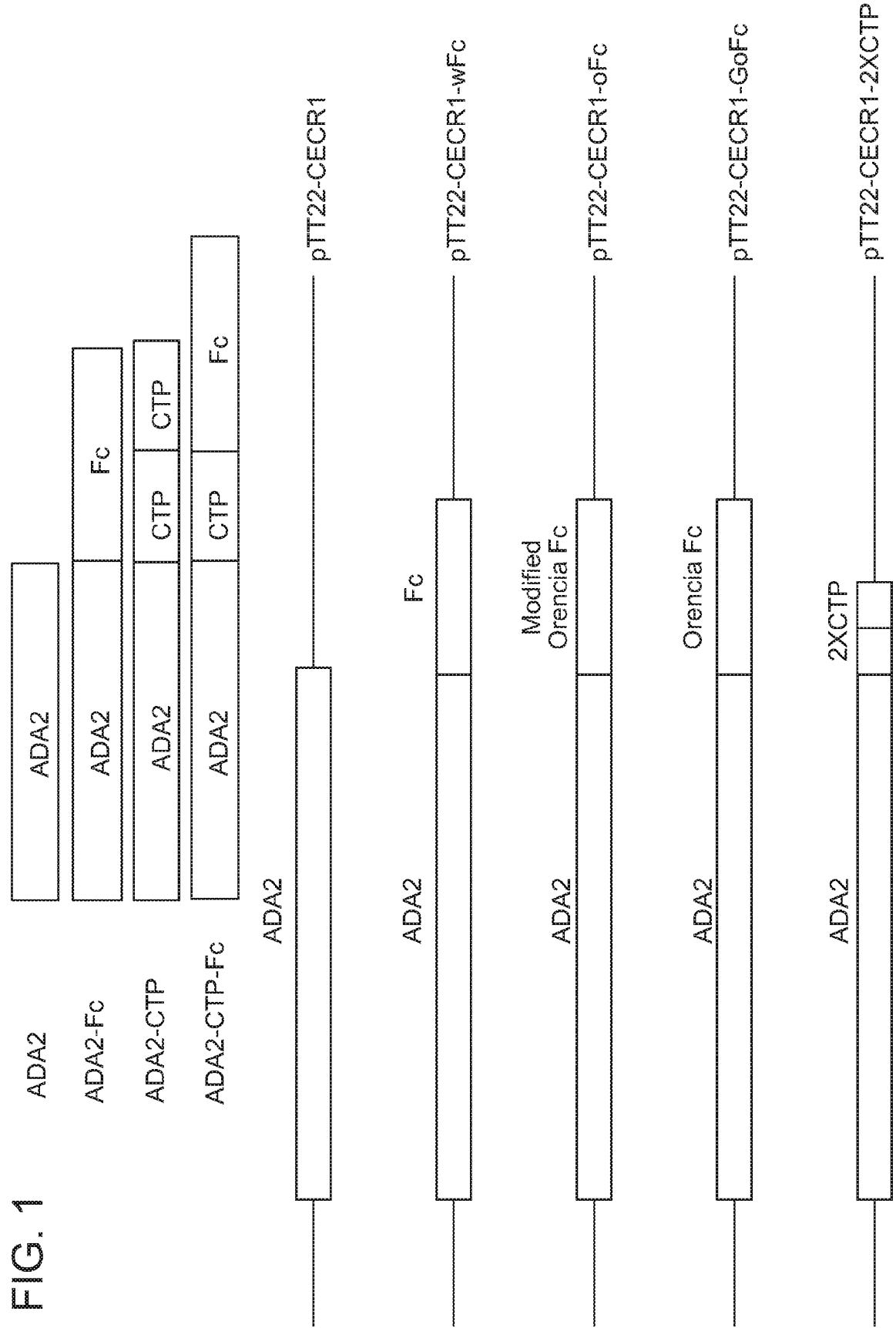
FIG. 1 depicts ADA2 proteins and ADA2 fusion proteins of the invention.

The protein sequence encoded by the degenerate CECR1 (ADA2) nucleic acid sequence is identical to the wild-type ADA2 protein (e.g., SEQ ID NO:1) due to degeneracy of the code. The Orencia Fc sequence is underlined.

FIGS. 33A and 33B depict the nucleotide sequence of ADA2-2xCTP (SEQ ID NO:24) and the protein sequence of ADA2-2xCTP (SEQ ID NO:23). The boxed nucleotides denote nucleotide differences between this coding region and that of the NCBI sequence of wild-type CECR1 (ADA2) transcript variant 3 (NM_001282225.1). The protein sequence encoded by the degenerate CECR1(ADA2) nucleic acid sequence is identical to the wild-type ADA2 protein (e.g., SEQ ID NO:1) due to degeneracy of the code. The 2xCTP sequence is underlined.

FIG. 34 depicts a nucleotide sequence of CECR1 (ADA2) of SEQ ID NO:36. The boxed nucleotides denote nucleotide differences between this coding region and that of the NCBI sequence of wild-type CECR1 (ADA2) transcript variant 3 (NM_001282225.1). The protein sequence encoded by the degenerate CECR1 nucleic acid sequence is identical to the wild-type ADA2 protein (e.g., SEQ ID NO:1) due to degeneracy of the code.

DETAILED DESCRIPTION OF THE INVENTION

The present invention provides isolated recombinant human ADA2 proteins or ADA2 fusion proteins. The proteins of the invention can be surprisingly used to restore ADA2 activity in subjects having loss-of-function mutations in ADA2 and can increase differentiation of monocytes into M2 macrophages, e.g., M2a macrophages, M2b macrophages or M2c macrophages, stimulate CD4+ T cell proliferation, and increase endothelial cell development. More specifically, the ADA2 proteins and ADA2 fusion proteins of the invention can be used to treat subjects having ADA2-associated diseases or disorders, including but not limited to, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM.

Various aspects of the invention are described in further detail in the following subsections:

I. Isolated ADA2 Proteins, Fusions and Antibodies

In one aspect, the invention provides isolated human ADA2 proteins, biologically active portions thereof, and ADA2 fusion proteins. In one embodiment, native human ADA2 proteins can be isolated from cells or tissue sources by an appropriate purification scheme using standard protein purification techniques. In another embodiment, isolated human ADA2 proteins or ADA2 fusion proteins are produced by recombinant DNA techniques. Alternative to recombinant expression, an ADA2 protein or fusion protein can be synthesized chemically using standard peptide synthesis techniques.

In one embodiment, a human ADA2 protein of the invention has an amino acid sequence shown in SEQ ID NO: 1.

```
SEQ ID NO: 1: Wild-Type Human ADA2
  1 mlvdgpserp alcflllava msffgsalsi detrahlllk ekmmrlggrl vintkeelan 61 erlmtlkiae mkeamrtlif ppsmhffqak hliersqvfn ilrmmpkgaa lhlhdigivt 121 mdwlvrnvty rphchicftp rgimqfrfah ptprpsekcs kwilledyrk rvqnvtefdd 181 sllrnftlvt qhpeviytnq nvvwskfeti fftisglihy apvfrdyvfr smgefyednv 241 lymeirarll pvyelsgehh deewsvktyq evaqkfveth pefigikiiy sdhrskdvav 301 iaesirmamg lrikfptvva gfdlvghedt ghslhdykea lmipakdgvk lpyffhaget 361 dwqgtsidrn ildalmlntt righgfalsk hpavrtyswk kdipievcpi snqvlklvsd 421 lrnhpvatlm atghpmviss ddpamfgakg lsydfyevfm giggmkadlr tlkqlamnsi 481 kystllesek ntfmeiwkkr wdkfiadvat k
```

ADA2 variants created to study deaminase activity include D441E (SEQ ID NO:11); D442A (SEQ ID NO: 13); W362G (SEQ ID NO: 15); and H112Q (SEQ ID NO:17), where D441E and D442A are defective in deaminase catalytic activity, W362G is defective in dimerization; and H112Q is defective in zinc binding.

```
SEQ ID NO: 11: ADA2-D441E
  1 mlvdgpserp alcflllava msffgsalsi detrahlllk ekmmrlggrl vintkeelan 61 erlmtlkiae mkeamrtlif ppsmhffqak hliersqvfn ilrmmpkgaa lhlhdigivt 121 mdwlvrnvty rphchicftp rgimqfrfah ptprpsekcs kwilledyrk rvqnvtefdd 181 sllrnftivt qhpeviytnq nvvwskfeti fftisglihy apvfrdyvfr smgefyednv 241 lymeirarll pvyelsgehh deewsvktyq evaqkfveth pefigikiiy sdhrskdvav 301 iaesirmamg lrikfptvva gfdlvghedt ghslhdykea lmipakdgvk lpyffhaget 361 dwqgtsidrn ildalmlntt righgfalsk hpavrtyswk kdipievcpi snqvlklvsd
```

```
421 lrnhpvatlm atghpmviss edpamfgakg lsydfyevfm giggmkadlr tlkqlamnsi 481 kystllesek ntfmeiwkkr wdkfiadvat k SEQ ID NO: 13: ADA2-D442A
  1 mlvdgpserp alcflllava msffgsalsi detrahlllk ekmmrlggrl vintkeelan 61 erlmtlkiae mkeamrtlif ppsmhffqak hliersqvfn ilrmmpkgaa lhlhdigivt 121 mdwlvrnvty rphchicftp rgimqfrfah ptprpsekcs kwilledyrk rvqnvtefdd 181 sllrnftivt qhpeviytnq nvvwskfeti fftisglihy apvfrdyvfr smgefyednv 241 lymeirarll pvyelsgehh deewsvktyq evaqkfveth pefigikiiy sdhrskdvav 301 iaesirmamg lrikfptvva gfdlvghedt ghslhdykea lmipakdgvk lpyffhaget 361 dwqgtsidrn ildalmlntt righgfalsk hpavrtyswk kdipievcpi snqvlklvsd 421 lrnhpvatlm atghpmviss dapamfgakg lsydfyevfm giggmkadlr tlkqlamnsi 481 kystllesek ntfmeiwkkr wdkfiadvat k SEQ ID NO: 15: ADA2-W362G
  1 mlvdgpserp alcflllava msffgsalsi detrahlllk ekmmrlggrl vintkeelan 61 erlmtlkiae mkeamrtlif ppsmhffqak hliersqvfn ilrmmpkgaa lhlhdigivt 121 mdwlvrnvty rphchicftp rgimqfrfah ptprpsekcs kwilledyrk rvqnvtefdd 181 sllrnftivt qhpeviytnq nvvwskfeti fftisglihy apvfrdyvfr smgefyednv 241 lymeirarll pvyelsgehh deewsvktyq evaqkfveth pefigikiiy sdhrskdvav 301 iaesirmamg lrikfptvva gfdlvghedt ghslhdykea lmipakdgvk lpyffhaget 361 dgqgtsidrn ildalmlntt righgfalsk hpavrtyswk kdipievcpi snqvlklvsd 421 lrnhpvatlm atghpmviss ddpamfgakg lsydfyevfm giggmkadlr tlkqlamnsi 481 kystllesek ntfmeiwkkr wdkfiadvat k SEQ ID NO: 17: ADA2-H112Q
  1 mlvdgpserp alcflllava msffgsalsi detrahlllk ekmmrlggrl vintkeelan 61 erlmtlkiae mkeamrtlif ppsmhffqak hliersqvfn ilrmmpkgaa lqlhdigivt 121 mdwlvrnvty rphchicftp rgimqfrfah ptprpsekcs kwilledyrk rvqnvtefdd 181 sllrnftivt qhpeviytnq nvvwskfeti fftisglihy apvfrdyvfr smgefyednv 241 lymeirarll pvyelsgehh deewsvktyq evaqkfveth pefigikiiy sdhrskdvav 301 iaesirmamg lrikfptvva gfdlvghedt ghslhdykea lmipakdgvk lpyffhaget 361 dwqgtsidrn ildalmlntt righgfalsk hpavrtyswk kdipievcpi snqvlklvsd 421 lrnhpvatlm atghpmviss ddpamfgakg lsydfyevfm giggmkadlr tlkqlamnsi 481 kystllesek ntfmeiwkkr wdkfiadvat k
```

In other embodiments, the invention includes ADA2 variants that increase the half-life of the ADA2 protein. In some embodiments, the ADA2 protein is a variant comprising one or more amino acid substitutions that increases the half-life of the protein. In some embodiments, one or more asparagine is substituted with a different amino acid to remove known or predicted N-glycosylation sites in the ADA2. In some embodiments, one or more asparagine is substituted with an alanine to remove a known or predicted N-glycosylation site in ADA2. In one embodiment, an asparagine residue is substituted with an alanine residue at position 127 of SEQ ID NO: 1. In one embodiment, an asparagine residue is substituted with an alanine residue at position 174 of SEQ ID NO: 1. In one embodiment, an asparagine residue is substituted with an alanine residue at position 185 of SEQ ID NO: 1. In one embodiment, an asparagine residue is substituted with an alanine residue at position 378 of SEQ ID NO: 1. In some embodiments, the ADA2 variant is ADA2-N127A (SEQ ID NO: 3), ADA2-N174A (SEQ ID NO: 5), ADA2-N185A (SEQ ID NO: 7), or ADA2-N378A (SEQ ID NO: 9). Representative sequences of the ADA2 variants are shown below.

SEQ ID NO: 3: Amino Acid Sequence of ADA2-N127A
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRAV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATK

SEQ ID NO: 5: Amino Acid Sequence of ADA2-N174A
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQAVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATK

SEQ ID NO: 7: Amino Acid Sequence of ADA2-N185A
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRAFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATK

SEQ ID NO: 9: Amino Acid Sequence of ADA2-N378A
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLATTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATK

In one embodiment, the ADA2 variants of the invention comprise one or more amino acid substitutions that increase the half-life of the protein. As used herein, "one or more amino acid substitutions that increase the half-life of the protein" refers to one or more mutations that, when introduced into an ADA2 polypeptide or biologically active fragment, changes one or more amino acid residues present in the wild-type sequence into one or more different amino acid residues, thereby leading to an increase in the half-life of the variant ADA2 polypeptide or biologically active fragment as compared to the half-life of the wild-type ADA2 polypeptide or biologically active fragment. In one embodiment, the half-life of the ADA2 variant protein is increased 50% as compared to the half-life of the wild-type ADA2 polypeptide or biologically active fragment. In another embodiment, the half-life of the ADA2 variant protein is increased 60% as compared to the half-life of the wild-type ADA2 polypeptide or biologically active fragment. In another embodiment, the half-life of the ADA2 variant protein is increased 70% as compared to the half-life of the wild-type ADA2 polypeptide or biologically active fragment. In another embodiment, the half-life of the ADA2 variant protein is increased 80% as compared to the half-life of the wild-type ADA2 polypeptide or biologically active fragment. In another embodiment, the half-life of the ADA2 variant protein is increased 90% as compared to the half-life of the wild-type ADA2 polypeptide or biologically active fragment. In another embodiment, the half-life of the ADA2 variant protein is increased 2 fold, 3 fold, 4 fold, 5 fold, 6 fold, 7 fold, 8 fold, 9 fold, or 10 fold as compared to the half-life of the wild-type ADA2 polypeptide or biologically active fragment. Methods for determining the half-life of a protein or fusion protein are well known in the art. For example, Zhou et al., Determining Protein Half-Lives, Methods in Molecular Biology, 284:67-77, 2004 discloses numerous methods for testing of the half-life of a protein.

In other embodiments, the ADA2 protein of the invention is substantially homologous to SEQ ID NO:1, and retains the functional activity of the protein of SEQ ID NO:1, yet differs in amino acid sequence due to natural allelic variation or mutagenesis, as described in detail herein. Accordingly, in another embodiment, the ADA2 protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:1. In another embodiment, the ADA2 protein of the invention is sufficiently identical to SEQ ID NO:1.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%-80%, and even more preferably 90%-95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70%-80%, or 90%-95% identity and share a common functional activity are defined herein as sufficiently identical.

As used herein, a "biologically active portion" or "biologically active fragment" of an ADA2 protein includes a fragment of an ADA2 protein which participates in an interaction between an ADA2 molecule and a non-ADA2 molecule. Alternatively, a "biologically active portion" or a "biologically active fragment" of an ADA2 protein includes a fragment of an ADA2 protein which retains one or more activities of the wild-type ADA2 protein including, but not limited to, adenosine deaminase activity, binding to a receptor, increasing differentiation of monocytes into macrophages, e.g., M2 macrophages, e.g., M2a macrophages, M2b macrophages or M2c macrophages, stimulating CD4+ T cell proliferation, and/or increasing endothelial cell development.

Biologically active portions of an ADA2 protein include peptides comprising amino acid sequences sufficiently identical to (e.g., at least 90%, 91%, 92%, 93%, 94%, 95%, 96%, 97%, 98%, 99%) or derived from the amino acid sequence of the wild-type human ADA2 protein, e.g., the amino acid sequence shown in SEQ ID NO:1, which can include less amino acids than the full length ADA2 proteins, and exhibit at least one activity of an ADA2 protein described herein. Typically, biologically active portions comprise a domain or motif with at least one activity of the ADA2 protein, e.g., increasing differentiation of monocytes into macrophages, e.g., M2 macrophages, e.g., M2a macrophages, M2b macrophages or M2c macrophages, stimulating CD4+ T cell proliferation, and/or increasing endothelial cell development. The biologically active portion comprises a domain or motif having at least one activity of inducing proliferation of the M2 macrophages that exhibit CD163+ expression (e.g., M2a and/or M2c phenotypes).

A biologically active portion of an ADA2 protein can be a polypeptide which is, for example, 10, 25, 50, 100, 200, or more amino acids in length. Biologically active portions of an ADA2 protein can be used in the pharmaceutical compositions of the invention. Alternatively, biologically active portions of an ADA2 protein can be used in an ADA2 fusion protein of the invention. For example, a biologically active portion of an ADA2 protein can be linked (or fused) to at least one CTP domain (e.g., SEQ ID NO:29: SSSSKAPPPSLPSPSRLPGPSDTPILPQ), at least two CTP domains (e.g., SEQ ID NO:30: SSSSKAPPPSLPSPSRLPGPSDTPILPQSSSSKAPPPSLPSPSRLPGPSDTPILPQ) or an Fc domain of an IgG. In one embodiment, the Fc domain of an Ig is a wild-type Fc domain of an Ig, for example:

```
SEQ ID NO: 27: Wild-Type Fc Domain
EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In another embodiment, the Fc domain of an Ig is an Orencia Fc domain of an Ig, for example:

```
SEQ ID NO: 28: Orencia Fc Domain
EPKSSDKTHTCPPCPAPEAAGGSSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

The biologically active portion can be linked via its C-terminus or its N-terminus. Biologically active portions, in which other regions of the protein are deleted, can be prepared by recombinant techniques and evaluated for one or more of the functional activities of a native ADA2 protein.

Without wishing to be bound by theory, there exist a several possible modes of ADA2 action in restoration of immune function in subjects suffering from ADA2 deficiency. ADA2 may decrease adenosine concentrations to remove toxic derivatives of adenosine (i.e., desoxiadenosine) in and/or around the cell to deactivate adenosine receptors. ADA2 may bind indirectly/directly to the adenosine receptors, proteoglycans, and/or other putative receptors. ADA2 protein may help to bridge cells during "immunological synapse" formation. It is believed that ADA2 protein may bind to a receptor to elicit M2 (anti-inflammatory) phenotypes in macrophages. The binding domain can be an important element for eliciting the anti-inflammatory effect, particularly resulting in growth of endothelial cells, restoring and normalizing vasculature and other damaged tissues associated ADA2 defects.

Symptoms associated with ADA2 deficiency include, but are not limited to, lacunar stroke and vasculitis, Sneddon's syndrome, microscopic polyangitis, Wegnener's granulamatosis, Churg-Strauss syndrome, Takayasu arteritis, Giant cell arteritis, Livedoid vasculopathy, and small vessel vasculitis. The ADA2 proteins and fusion proteins of the invention can reduce acute-phase reactant, gastrointestinal manifestation (e.g., abdominal pain), neurological manifestations (e.g., pain, numbness), and stroke occurrence in case of recurring stroke. The ADA2 proteins and fusion proteins of the present invention can ameliorate fever and rash in case of livedo articularis, livedo racemosa, reduces neutrophil and macrophage infiltration in skin biopsies, ameliorate hypertension in case with renal hypertension. Any measure of remission or reduction in number of events over predefined time period would be a suitable indication for successful treatment.

An "isolated" or "purified" ADA2 protein or biologically active portion thereof is substantially free of cellular material or other contaminating proteins from the cell or tissue source from which the ADA2 protein or ADA2 fusion protein is derived, or substantially free from chemical precursors or other chemicals when chemically synthesized. The language "substantially free of cellular material" includes preparations of ADA2 protein or ADA2 fusion protein in which the protein is separated from cellular components of the cells from which it is isolated or recombinantly produced. In one embodiment, the language "substantially free of cellular material" includes preparations of ADA2 protein or ADA2 fusion protein having less than about 30% (by dry weight) of non-ADA2 protein/fusion protein (also referred to herein as a "contaminating protein"), more preferably less than about 20% of non-ADA2 protein/fusion protein, still more preferably less than about 10% of non-ADA2 protein/fusion protein, and most preferably less than about 5% non-ADA2 protein/fusion protein. When the ADA2 protein, fusion protein, or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ADA2 protein or ADA2 fusion protein in which the protein is separated from chemical precursors or other chemicals which are involved in the synthesis of the protein. In one embodiment, the language "substantially free of chemical precursors or other chemicals" includes preparations of ADA2 protein or fusion protein having less than about 30% (by dry weight) of chemical precursors or non-ADA2 chemicals, more preferably less than about 20% chemical precursors or non-ADA2 chemicals, still more preferably less than about 10% chemical precursors or non-ADA2 chemicals, and most preferably less than about 5% chemical precursors or non-ADA2 chemicals.

Preferred ADA2 proteins and ADA2 fusion proteins of the invention comprising ADA2 having at least one ADA2 activity. Other preferred ADA2 proteins and ADA2 fusion proteins of the invention form functional homodimers. ADA2 proteins and ADA2 fusion proteins of the invention are, preferably, encoded by a nucleic acid molecule having a nucleotide sequence which hybridizes under stringent hybridization conditions to a nucleic acid molecule comprising the nucleotide sequence of SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the ADA2 amino acid sequence of SEQ ID NO:1, at least 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to ADA2 nucleic acid molecules of the invention. BLAST protein searches can be performed with the XBLAST program, score=50, wordlength=3 to obtain amino acid sequences homologous to ADA2 protein molecules of the invention. To obtain gapped alignments for comparison purposes, Gapped BLAST can be utilized as described in Altschul et al., (1997) Nucleic Acids Res. 25(17):3389-

3402. When utilizing BLAST and Gapped BLAST programs, the default parameters of the respective programs (e.g., XBLAST and NBLAST) can be used.

The invention also provides ADA2 fusion proteins. As used herein, an "ADA2 fusion protein" comprises an ADA2 protein or an ADA2 biologically active fragment operatively linked to a non-ADA2 polypeptide. An "ADA2 polypeptide" or "ADA2 protein" refers to a polypeptide having an amino acid sequence corresponding to ADA2 or a fragment thereof, or being homologous to an ADA2 protein or biologically active portion thereof, as described above, whereas a "non-ADA2 polypeptide" refers to a polypeptide having an amino acid sequence corresponding to a protein which is not substantially homologous to the ADA2 protein, e.g., a protein which is different from the ADA2 protein and which is derived from the same or a different organism. Within an ADA2 fusion protein, the ADA2 polypeptide or protein can correspond to all, or a fragment or portion of the full length human ADA2 protein. In a preferred embodiment, an ADA2 fusion protein of the invention comprises at least one biologically active portion of an ADA2 protein. In another preferred embodiment, an ADA2 fusion protein comprises at least two biologically active portions of an ADA2 protein.

Within the fusion protein, the term "operatively linked" is intended to indicate that the ADA2 polypeptide and the non-ADA2 polypeptide are fused in-frame to each other. The non-ADA2 polypeptide can be fused to the N-terminus or C-terminus of the ADA2 polypeptide. In one embodiment, the non-ADA2 polypeptide is fused to the N-terminus of the ADA2 polypeptide. In another embodiment, the non-ADA2 polypeptide is fused to the C-terminus of the ADA2 polypeptide.

The non-ADA2 polypeptide can be fused directly to the ADA2 polypeptide or biologically active fragment. Alternatively, the non-ADA2 polypeptide can be fused to the ADA2 polypeptide or biologically active fragment via a linker. Examples of peptide linkers are set forth in FIG. 5 and include GGGSGGGAS (SEQ ID NO:31), GGGSGGGSGGGAS (SEQ ID NO:32), SHGGGSGGGSGGGSGGGAS (SEQ ID NO:33), GGGSGGGSGGGSGGGAS (SEQ ID NO:34) or GGGAS (SEQ ID NO:35).

In one embodiment, the ADA2 fusion protein of the invention comprises an ADA2 polypeptide and a protein that increases the half-life of the fusion protein. As used herein, a "protein that increases the half-life of the fusion protein" refers to a protein that, when fused to an ADA2 polypeptide or biologically active fragment, increases the half-life of the ADA2 polypeptide or biologically active fragment as compared to the half-life of the ADA2 polypeptide, alone, or the ADA2 biologically active fragment, alone. In one embodiment, the half-life of the ADA2 fusion protein is increased 50% as compared to the half-life of the ADA2 polypeptide or biologically active fragment, alone. In another embodiment, the half-life of the ADA2 fusion protein is increased 60% as compared to the half-life of the ADA2 polypeptide or biologically active fragment, alone. In another embodiment, the half-life of the ADA2 fusion protein is increased 70% as compared to the half-life of the ADA2 polypeptide or biologically active fragment, alone. In another embodiment, the half-life of the ADA2 fusion protein is increased 80% as compared to the half-life of the ADA2 polypeptide or biologically active fragment, alone. In another embodiment, the half-life of the ADA2 fusion protein is increased 90% as compared to the half-life of the ADA2 polypeptide or biologically active fragment, alone. In another embodiment, the half-life of the ADA2 fusion protein is increased 2 fold, 3 fold, 4 fold, 5 fold, 6 fold, 7 fold, 8 fold, 9 fold, or 10 fold as compared to the half-life of the ADA2 polypeptide or biologically active fragment, alone. Methods for determining the half-life of a protein or fusion protein are well known in the art. For example, Zhou et al., Determining Protein Half-Lives, Methods in Molecular Biology, 284:67-77, 2004 discloses numerous methods for testing of the half-life of a protein.

In one embodiment, the protein which increases the half-life of the fusion protein is a CTP sequence (SEQ ID NO:29) (see also, Fares et al., 2010, Endocrinol., 151(9): 4410-4417; Fares et al., 1992, Proc. Natl. Acad. Sci, 89(10): 4304-4308; and Furuhashi et al., 1995, Molec. Endocrinol., 9(1):54-63). In another embodiment, the protein which increases the half-life of the fusion protein is two CTP sequences in tandem.

In another embodiment, the protein which increases the half-life of the fusion protein is an Fc domain of an Ig. In one embodiment, the Fc domain of an Ig is a wild-type Fc domain. In one embodiment, the Fc domain of an Ig is a wild-type Fc domain of IgG1. In another embodiment, the Fc domain of an Ig is an Orencia Fc domain.

In one embodiment, the fusion protein is a CTP-ADA2 fusion protein in which the ADA2 sequence is fused to the C-terminus of the CTP sequence. In another embodiment, the fusion protein is a CTP-ADA2 fusion protein in which the ADA2 sequence is fused to the N-terminus of the CTP sequence. In one embodiment, the fusion protein is a CTP-ADA2 fusion protein in which the ADA2 sequence is fused to the C-terminus of two CTP sequences. In another embodiment, the fusion protein is a CTP-ADA2 fusion protein in which the ADA2 sequence is fused to the N-terminus of two CTP sequences. In another embodiment, the fusion protein is a Fc-ADA2 fusion protein in which the ADA2 sequence is fused to the C-terminus of the Fc domain of an Ig. In another embodiment, the fusion protein is an Fc-ADA2 fusion protein in which the ADA2 sequence is fused to the N-terminus of the Fc domain of an Ig.

Representative sequences for ADA2 fusion proteins of the invention are shown below.

```
SEQ ID NO: 19: Amino Acid Sequence of ADA2-wFc
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH
```

-continued

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATKE

PKSCDKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPGK

SEQ ID NO: 21: Amino Acid Sequence of ADA2-oFc
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATKE

PKSSDKTHTCPPCPAPEAAGGSSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGK

SEQ ID NO: 23: Amino Acid Sequence of ADA2-2xCTP
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATKS

SSSKAPPPSLPSPSRLPGPSDTPILPQSSSSKAPPPSLPSPSRLPGPSDTPILPQ

SEQ ID NO: 25: Amino Acid Sequence of ADA2-GoFc
MLVDGPSERPALCFLLLAVAMSFFGSALSIDETRAHLLLKEKMMRLGGRLVLNTKEELANERLM

TLKIAEMKEAMRTLIFPPSMHFFQAKHLIERSQVFNILRMMPKGAALHLHDIGIVTMDWLVRNV

TYRPHCHICFTPRGIMQFRFAHPTPRPSEKCSKWILLEDYRKRVQNVTEFDDSLLRNFTLVTQH

PEVIYTNQNVVWSKFETIFFTISGLIHYAPVFRDYVFRSMQEFYEDNVLYMEIRARLLPVYELS

GEHHDEEWSVKTYQEVAQKFVETHPEFIGIKIIYSDHRSKDVAVIAESIRMAMGLRIKFPTVVA

GFDLVGHEDTGHSLHDYKEALMIPAKDGVKLPYFFHAGETDWQGTSIDRNILDALMLNTTRIGH

GFALSKHPAVRTYSWKKDIPIEVCPISNQVLKLVSDLRNHPVATLMATGHPMVISSDDPAMFGA

KGLSYDFYEVFMGIGGMKADLRTLKQLAMNSIKYSTLLESEKNTFMEIWKKRWDKFIADVATKE

PKSSDKTHTSPPSPAPELLGGSSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGK

In another embodiment, the fusion protein is an ADA2 protein containing a heterologous signal sequence at its N-terminus. In certain host cells (e.g., mammalian host cells), expression and/or secretion of the ADA2 proteins or the ADA2 fusion proteins of the invention can be increased through use of a heterologous signal sequence.

The ADA2 proteins and ADA2 fusion proteins of the invention can be incorporated into pharmaceutical compositions and administered to a subject in vivo. The ADA2 proteins and ADA2 fusion proteins are useful therapeutically for the treatment of ADA2-associated diseases or disorders, as described below.

Moreover, the ADA2 proteins and ADA2 fusion proteins of the invention can be used as immunogens to produce anti-ADA2 antibodies in a subject, to purify ADA2 ligands and in screening assays to identify molecules which inhibit the interaction of ADA2 with an ADA2 substrate.

Preferably, an ADA2 protein or an ADA2 fusion protein of the invention is produced by standard recombinant DNA techniques. For example, for fusion proteins, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An ADA2-encoding nucleic acid can be cloned into such an expression vector such that the fusion moiety is linked in-frame to the ADA2 protein.

ADA2 proteins, functional fragments, or ADA2 fusion proteins of the invention can be purified to various grades of purity. The purity of the protein in a composition is at least equal to or greater than 80%, 82%, 85%, 87%, 90%, 93%, 95%, 96%, 97%, 98%, or 99% by total protein as determined by HPLC methods. A composition comprising an ADA2 protein, functional fragment, or fusion protein of the invention can be purified to a grade that is essentially free of non-ADA2 protein, ADA2 protein fragment, or ADA2 fusion protein. A composition comprising ADA2, functional fragments, or fusion proteins can also be purified to a state wherein the ADA2, functional fragment, or fusion protein is essentially pure. An ADA2, functional fragment, or fusion protein can be present in a solution or in a lyophilized preparation.

II. Isolated ADA2 (CECR1) Nucleic Acid Molecules

One aspect of the invention pertains to isolated nucleic acid molecules that encode ADA2 proteins, ADA2 fusion proteins, or biologically active portions thereof, as well as nucleic acid fragments sufficient for use as hybridization probes to identify ADA2-encoding nucleic acid molecules (e.g., ADA2 mRNA) and fragments for use as PCR primers for the amplification or mutation of ADA2 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ADA2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention includes, e.g., a nucleic acid molecule having the nucleotide sequence of SEQ ID NO: 2 (wild-type human ADA2). ADA2 nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

```
SEQ ID NO: 2: Wild-Type Human ADA2 (CECR1)
atgttggtggatggcccatctgagcggccagccctgtgcttcttgctgttggctgtggcaatgt ctttcttcggctcagctctatccatagatgaaacacgggcgcatctgttgttgaaagaaaagat gatgcggctggggggcggctggtgctgaacaccaaggaggagctggccaatgagaggctcatg acgctcaaaatcgctgagatgaaggaggccatgaggaccctgatattcccacccagcatgcact ttttccaggccaagcatctcattgagagaagtcaagtgtttaatattctaaggatgatgccaaa aggggctgccttgcacctccatgacattggcatcgtgactatggactggctggtgaggaatgtc acctacaggcctcactgccacatctgtttcaccccaaggggggatcatgcagttcagatttgctc acccaactccccgtccatcagaaaaatgttccaagtggattctgctggaggattatcggaagcg ggtgcagaacgtcactgagtttgatgacagcttgctgaggaatttcactctggtgacccagcac ccggaggtgatttacacaaaccaaaatgttgtctggtcgaaatttgaaaccatcttcttcacca
```

```
tctctggtctcatccattacgcaccagtgttcagagactatgtcttccggagcatgcaggagtt ctacgaggacaacgtgctctacatggagatcagagccaggctgctgccggtgtatgagctcagt ggagagcaccatgacgaagagtggtcagtgaagacttaccaggaagtagctcagaagtttgtgg aaactcaccctgagtttattggaatcaaaatcatttattcggatcacagatccaaagatgtggc tgtcatcgcagaatccatccgaatggccatggggctccgaatcaagttccccacggtggtggca gggtttgacctggtggggcatgaggacactggccactccttgcatgactacaaggaagctctga tgatccccgccaaggatggcgttaagctgccttacttcttccacgccggagaaacagactggca gggtacttccatagacaggaacattctggatgctctgatgctgaacactaccagaatcggccat ggatttgctttgagcaaacaccccgcagtcaggacttactcctggaaaaaggacatccccatag aagtctgtcccatctctaaccaggtgctgaaactggtgtctgacttgaggaaccaccctgtagc cactctgatggccactgggcacccatggtgatcagctctgatgacccagctatgtttggtgcc aaaggcttgtcctatgatttctatgaggtcttcatgggcattggggggatgaaggctgacctga ggaccctcaaacagctggccatgaactctatcaagtacagtaccctgttggagagtgagaaaaa tactttcatggaaatctggaagaagagatgggataagttcatagcagatgtggctacaaagtga
```

A nucleic acid molecule of the present invention includes, e.g., a nucleic acid molecule having the nucleotide sequence of SEQ ID NO:36, which differs from the wild-type human ADA2 nucleic acid sequence (SEQ ID NO:2), but still encodes a protein identical to wild-type human ADA2 (SEQ ID NO:1) due to degeneracy of the code. For example, nucleic acids indicated with boxes in SEQ ID NO:36 differ from the nucleic acids of the wild-type ADA2 of SEQ ID NO:2.

```
SEQ ID NO: 36: ADA2 Nucleic Acid Sequence
ATGTTGGTGGATGGCCCATCTGAGCGGCCAGCCCTGTGCTTCTTGCTGTTGGCTGTGGCAATGT

CTTTCTTCGGCTCAGCTCTATCCATAGATGAAACACGGGCGCATCTGTTGTTGAAAGAAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGCACCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTAACAGGAAGTAGCTCAGAAGTTTGTGG

AAACTCACCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTAATCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC
```

-continued

AAAGGCTTGTCCTATGATTTCTATGAGGTCTTCATGGGCATTGGGGGGATGAAGGCTGA[]CTGA

GGACCCTCAAACAGCTGGCCATGAACTCTATCAAGTACAGTACCCTGTTGGAGAGTGAGAAAAA

TACTTTCATGGAAAT[A]TGGAAGAAGAGATGGGATAAGTTCATAGCAGATGTGGCTACAAAGTGA

The present invention also includes nucleic acid sequences for ADA2-Fc fusions, including ADA2-wild-type Fc fusions (SEQ ID NO:20), ADA2-Orencia-Fc fusions (SEQ ID NO:22), and modified ADA2-Orencia-Fc fusions (SEQ ID NO:26).

```
SEQ ID NO: 20: ADA2-Wild-Type Fc Fusion Nucleic Acid Sequence
ATGTTGGTGGATGGCCCATCTGAGCGGCCAGCCCTGTGCTTCTTGCTGTTGGCTGTGGCAATGT

CTTTCTTCGGCTC[]GCTCTATCCATAGATGAAACACGGGCGCATCTGTTGTTGAAAGAAAAGAT

GATGCGGCTGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAATGTTGTCTGGTCGAAATTTGAAACCATCTTCTTCACCA

TCTCTGGTCTCATCCATTACGC[]CCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTA[]CAGGAAGTAGCTCAGAAGTTTGTGG

AAACTCA[]CCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTA[]TCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGA[]CTGA

GGACCCTCAAACAGCTGGCCATGAACTCTATCAAGTACAGTACCCTGTTGGAGAGTGAGAAAAA

TACTTTCATGGAAAT[A]TGGAAGAAGAGATGGGATAAGTTCATAGCAGATGTGGCTACAAAGGAG

CCCAAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGAGGT

CACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGTG

TGGTCAGCGTCCTCACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCAAAGGGCAGCCCCGA
```

-continued

GAACCACAGGTGTACACCCTGCCCCCATCCCGGGAGGAGATGACCAAGAACCAGGTCAGCCTGA

CCTGCCTGGTCAAAGGCTTCTATCCCAGCGACATCGCCGTGGAGTGGGAGAGCAATGGGCAGCC

GGAGAACAACTACAAGACCACGCCTCCCGTGCTGGACTCCGACGGCTCCTTCTTCCTCTACAGC

AAGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCCCCGGGTAAATGA

SEQ ID NO: 22: ADA2-Orencia Fc Fusion Nucleic Acid Sequence
ATGTTGGTGGATGGCCCATCTGAGCGGCCAGCCCTGTGCTTCTTGCTGTTGGCTGTGGCAATGT

CTTTCTTCGGCTC☐GCTCTATCCATAGATGAAACACGGGCGCATCTGTTGTTGAAAGAAAAGAT

GATGCGGCTGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGC☐CCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTA☐CAGGAAGTAGCTCAGAAGTTTGTGG

AAACTCA☐CCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTA☐TCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGA☐CTGA

GGACCCTCAAACAGCTGGCCATGAACTCTATCAAGTACAGTACCCTGTTGGAGAGTGAGAAAAA

TACTTTCATGGAAAT☐TGGAAGAAGAGATGGGATAAGTTCATAGCAGATGTGGCTACAAAGGAG

CCCAAATCCTCCGACAAGACACACACATGTCCTCCCTGTCCCGCTCCTGAAGCTGCCGGAGGAT

CCAGCGTGTTTCTCTTCCCTCCTAAGCCCAAGGACACCCTCATGATCAGCAGAACCCCCGAAGT

CACCTGCGTCGTGGTCGACGTCTCCCACGAGGACCCCGAAGTGAAGTTCAACTGGTACGTGGAC

GGAGTCGAGGTCCACAACGCCAAGACCAAGCCCAGGGAGGAGCAGTACAACAGCACATACAGGG

TGGTGAGCGTCCTCACCGTCCTCCATCAGGACTGGCTGAACGGCAAGGAGTACAAATGCAAGGT

GAGCAATAAGGCCCTCCCTGCCCCCATCGAAAAGACCATCTCCAAAGCCAAGGGCCAACCTAGA

GAACCCCAGGTCTATACCCTCCCTCCCTCCAGAGACGAGCTCACAAAGAACCAGGTCAGCCTGA

CCTGTCTGGTGAAGGGATTCTACCCTTCCGACATTGCCGTCGAGTGGGAGTCCAATGGCCAGCC

CGAGAACAATTACAAGACCACACCCCCTGTCCTCGACTCCGACGGCTCCTTCTTCCTGTACTCC

AAGCTGACCGTCGACAAGTCCAGGTGGCAACAGGGCAACGTCTTCAGCTGCTCCGTCATGCATG

AGGCCCTCCACAACCACTACACACAGAAGTCCCTCTCCCTGAGCCCCGGCAAGTGA

SEQ ID NO: 26: Modified ADA2-Orencia Fc Fusion Nucleic Acid
Sequence (ADA2-GoFc)
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGCTCCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTATCAGGAAGTAGCTCAGAAGTTTGTGG

AAACTCATCCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTATTCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGATCTGA

GGACCCTCAAACAGCTGGCCATGAACTCTATCAAGTACAGTACCCTGTTGGAGAGTGAGAAAAA

TACTTTCATGGAAATATGGAAGAAGAGATGGGATAAGTTCATAGCAGATGTGGCTACAAAGGAG

CCCAAATCTTCTGACAAAACTCACACATCCCCACCGTCCCCAGCACCTGAACTCCTGGGGGGAT

CGTCAGTCTTCCTCTTCCCCCCAAAACCCAAGGACACCCTCATGATCTCCCGGACCCCTGAGGT

CACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGTG

TGGTCAGCGTCCTCACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCAAAGGGCAGCCCCGA

GAACCACAGGTGTACACCCTGCCCCCATCCCGGGATGAGCTGACCAAGAACCAGGTCAGCCTGA

CCTGCCTGGTCAAAGGCTTCTATCCCAGCGACATCGCCGTGGAGTGGGAGAGCAATGGGCAGCC

GGAGAACAACTACAAGACCACGCCTCCCGTGCTGGACTCCGACGGCTCCTTCTTCCTCTACAGC

AAGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCCCCGGGTAAATGA

The present invention also includes nucleic acid sequences for ADA2-CTP fusions, including ADA2-2xCTP fusions (SEQ ID NO:24).

```
SEQ ID NO: 24: ADA2-2xCTP Fusion Nucleic Acid Sequence
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGCTCCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTATCAGGAAGTAGCTCAGAAGTTTGTGG

AAACTCATCCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTATTCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGATCTGA

GGACCCTCAAACAGCTGGCCATGAACTCTATCAAGTACAGTACCCTGTTGGAGAGTGAGAAAAA

TACTTTCATGGAAATATGGAAGAAGAGATGGGATAAGTTCATAGCAGATGTGGCTACAAAGTCC

TCTTCCTCAAAGGCACCTCCACCTAGCCTTCCAAGTCCATCCCGACTCCCGGGGCCCTCGGACA

CCCCGATCCTCCCACAATCTTCCTCTTCCAAAGCTCCCCCTCCATCCCTACCTTCTCCTTCGCG

TCTCCCTGGTCCTTCCGATACACCAATTCTACCCCAGTGA
```

The present invention also includes nucleic acid sequences for ADA2 variants, including ADA2-N127A (SEQ ID NO:4), ADA2-N174A (SEQ ID NO:6), ADA2-N185A (SEQ ID NO:8, ADA2-N378A (SEQ ID NO:10), ADA2-D441E (SEQ ID NO:12), ADA2-D442A (SEQ ID NO:14), ADA2-W362G (SEQ ID NO:16), and ADA2-H112Q (SEQ ID NO:18).

```
SEQ ID NO: 4: ADA2-N127A
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAGAT
```

-continued

```
GATGCGGCTGGGGGGCGGCTGGTGCTGAACACCAAGGAGGAGCTGGCCAATGAGAGGCTCATG
ACGCTCAAAATCGCTGAGATGAAGGAGGCCATGAGGACCCTGATATTCCCACCCAGCATGCACT
TTTTCCAGGCCAAGCATCTCATTGAGAGAAGTCAAGTGTTTAATATTCTAAGGATGATGCCAAA
AGGGGCTGCCTTGCACCTCCATGACATTGGCATCGTGACTATGGACTGGCTGGTGAGGGCCGTC
ACCTACAGGCCTCACTGCCACATCTGTTTCACCCCAAGGGGGATCATGCAGTTCAGATTTGCTC
ACCCAACTCCCCGTCCATCAGAAAAATGTTCCAAGTGGATTCTGCTGGAGGATTATCGGAAGCG
GGTGCAGAACGTCACTGAGTTTGATGACAGCTTGCTGAGGAATTTCACTCTGGTGACCCAGCAC
CCGGAGGTGATTTACACAAACCAAAATGTTGTCTGGTCGAAATTTGAAACCATCTTCTTCACCA
TCTCTGGTCTCATCCATTACGCTCCAGTGTTCAGAGACTATGTCTTCCGGAGCATGCAGGAGTT
CTACGAGGACAACGTGCTCTACATGGAGATCAGAGCCAGGCTGCTGCCGGTGTATGAGCTCAGT
GGAGAGCACCATGACGAAGAGTGGTCAGTGAAGACTTATCAGGAAGTAGCTCAGAAGTTTGTGG
AAACTCATCCTGAGTTTATTGGAATCAAAATCATTTATTCGGATCACAGATCCAAAGATGTGGC
TGTCATCGCAGAATCCATCCGAATGGCCATGGGGCTCCGAATCAAGTTCCCCACGGTGGTGGCA
GGGTTTGACCTGGTGGGGCATGAGGACACTGGCCACTCCTTGCATGACTACAAGGAAGCTCTGA
TGATCCCCGCCAAGGATGGCGTTAAGCTGCCTTACTTCTTCCACGCCGGAGAAACAGACTGGCA
GGGTACTTCCATAGACAGGAACATTCTGGATGCTCTGATGCTGAACACTACCAGAATCGGCCAT
GGATTTGCTTTGAGCAAACACCCCGCAGTCAGGACTTATTCCTGGAAAAAGGACATCCCCATAG
AAGTCTGTCCCATCTCTAACCAGGTGCTGAAACTGGTGTCTGACTTGAGGAACCACCCTGTAGC
CACTCTGATGGCCACTGGGCACCCCATGGTGATCAGCTCTGATGACCCAGCTATGTTTGGTGCC
AAAGGCTTGTCCTATGATTTCTATGAGGTCTTCATGGGCATTGGGGGGATGAAGGCTGATCTGA
GGACCCTCAAACAGCTGGCCATGAACTCTATCAAGTACAGTACCCTGTTGGAGAGTGAGAAAAA
TACTTTCATGGAAATATGGAAGAAGAGATGGGATAAGTTCATAGCAGATGTGGCTACAAAGTGA
SEQ ID NO: 6: ADA2-N174A
ATGTTGGTGGATGGCCCATCTGAGCGGCCAGCCCTGTGCTTCTTGCTGTTGGCTGTGGCAATGT
CTTTCTTCGGCTCTGCTCTATCCATAGATGAAACACGGGCGCATCTGTTGTTGAAAGAAAAGAT
GATGCGGCTGGGGGGCGGCTGGTGCTGAACACCAAGGAGGAGCTGGCCAATGAGAGGCTCATG
ACGCTCAAAATCGCTGAGATGAAGGAGGCCATGAGGACCCTGATATTCCCACCCAGCATGCACT
TTTTCCAGGCCAAGCATCTCATTGAGAGAAGTCAAGTGTTTAATATTCTAAGGATGATGCCAAA
AGGGGCTGCCTTGCACCTCCATGACATTGGCATCGTGACTATGGACTGGCTGGTGAGGAATGTC
ACCTACAGGCCTCACTGCCACATCTGTTTCACCCCAAGGGGGATCATGCAGTTCAGATTTGCTC
ACCCAACTCCCCGTCCATCAGAAAAATGTTCCAAGTGGATTCTGCTGGAGGATTATCGGAAGCG
GGTGCAGGCCGTCACTGAGTTTGATGACAGCTTGCTGAGGAATTTCACTCTGGTGACCCAGCAC
CCGGAGGTGATTTACACAAACCAAAATGTTGTCTGGTCGAAATTTGAAACCATCTTCTTCACCA
TCTCTGGTCTCATCCATTACGCTCCAGTGTTCAGAGACTATGTCTTCCGGAGCATGCAGGAGTT
CTACGAGGACAACGTGCTCTACATGGAGATCAGAGCCAGGCTGCTGCCGGTGTATGAGCTCAGT
GGAGAGCACCATGACGAAGAGTGGTCAGTGAAGACTTATCAGGAAGTAGCTCAGAAGTTTGTGG
AAACTCATCCTGAGTTTATTGGAATCAAAATCATTTATTCGGATCACAGATCCAAAGATGTGGC
TGTCATCGCAGAATCCATCCGAATGGCCATGGGGCTCCGAATCAAGTTCCCCACGGTGGTGGCA
GGGTTTGACCTGGTGGGGCATGAGGACACTGGCCACTCCTTGCATGACTACAAGGAAGCTCTGA
TGATCCCCGCCAAGGATGGCGTTAAGCTGCCTTACTTCTTCCACGCCGGAGAAACAGACTGGCA
GGGTACTTCCATAGACAGGAACATTCTGGATGCTCTGATGCTGAACACTACCAGAATCGGCCAT
```

```
GGATTTGCTTTGAGCAAACACCCCGCAGTCAGGACTTATTCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGATCTGA

GGACCCTCAAACAGCTGGCCATGAACTCTATCAAGTACAGTACCCTGTTGGAGAGTGAGAAAAA

TACTTTCATGGAAATATGGAAGAAGAGATGGGATAAGTTCATAGCAGATGTGGCTACAAAGTGA

SEQ ID NO: 8: ADA2-N185A
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGGCCTTCACTCTGGTGACCCAGCAC

CCGGAGGTGATTTACACAAACCAAAATGTTGTCTGGTCGAAATTTGAAACCATCTTCTTCACCA

TCTCTGGTCTCATCCATTACGCTCCAGTGTTCAGAGACTATGTCTTCCGGAGCATGCAGGAGTT

CTACGAGGACAACGTGCTCTACATGGAGATCAGAGCCAGGCTGCTGCCGGTGTATGAGCTCAGT

GGAGAGCACCATGACGAAGAGTGGTCAGTGAAGACTTATCAGGAAGTAGCTCAGAAGTTTGTGG

AAACTCATCCTGAGTTTATTGGAATCAAAATCATTTATTCGGATCACAGATCCAAAGATGTGGC

TGTCATCGCAGAATCCATCCGAATGGCCATGGGGCTCCGAATCAAGTTCCCCACGGTGGTGGCA

GGGTTTGACCTGGTGGGCATGAGGACACTGGCCACTCCTTGCATGACTACAAGGAAGCTCTGA

TGATCCCCGCCAAGGATGGCGTTAAGCTGCCTTACTTCTTCCACGCCGGAGAAACAGACTGGCA

GGGTACTTCCATAGACAGGAACATTCTGGATGCTCTGATGCTGAACACTACCAGAATCGGCCAT

GGATTTGCTTTGAGCAAACACCCCGCAGTCAGGACTTATTCCTGGAAAAAGGACATCCCCATAG

AAGTCTGTCCCATCTCTAACCAGGTGCTGAAACTGGTGTCTGACTTGAGGAACCACCCTGTAGC

CACTCTGATGGCCACTGGGCACCCCATGGTGATCAGCTCTGATGACCCAGCTATGTTTGGTGCC

AAAGGCTTGTCCTATGATTTCTATGAGGTCTTCATGGGCATTGGGGGGATGAAGGCTGATCTGA

GGACCCTCAAACAGCTGGCCATGAACTCTATCAAGTACAGTACCCTGTTGGAGAGTGAGAAAAA

TACTTTCATGGAAATATGGAAGAAGAGATGGGATAAGTTCATAGCAGATGTGGCTACAAAGTGA

SEQ ID NO: 10: ADA2-N378A
ATGTTGGTGGATGGCCCATCTGAGCGGCCAGCCCTGTGCTTCTTGCTGTTGGCTGTGGCAATGT

CTTTCTTCGGCTCTGCTCTATCCATAGATGAAACACGGGCGCATCTGTTGTTGAAAGAAAAGAT

GATGCGGCTGGGGGGGCGGCTGGTGCTGAACACCAAGGAGGAGCTGGCCAATGAGAGGCTCATG

ACGCTCAAAATCGCTGAGATGAAGGAGGCCATGAGGACCCTGATATTCCCACCCAGCATGCACT

TTTTCCAGGCCAAGCATCTCATTGAGAGAAGTCAAGTGTTTAATATTCTAAGGATGATGCCAAA

AGGGGCTGCCTTGCACCTCCATGACATTGGCATCGTGACTATGGACTGGCTGGTGAGGAATGTC

ACCTACAGGCCTCACTGCCACATCTGTTTCACCCCAAGGGGGATCATGCAGTTCAGATTTGCTC

ACCCAACTCCCCGTCCATCAGAAAAATGTTCCAAGTGGATTCTGCTGGAGGATTATCGGAAGCG

GGTGCAGAACGTCACTGAGTTTGATGACAGCTTGCTGAGGAATTTCACTCTGGTGACCCAGCAC

CCGGAGGTGATTTACACAAACCAAAATGTTGTCTGGTCGAAATTTGAAACCATCTTCTTCACCA
```

TCTCTGGTCTCATCCATTACGCTCCAGTGTTCAGAGACTATGTCTTCCGGAGCATGCAGGAGTT
CTACGAGGACAACGTGCTCTACATGGAGATCAGAGCCAGGCTGCTGCCGGTGTATGAGCTCAGT
GGAGAGCACCATGACGAAGAGTGGTCAGTGAAGACTTATCAGGAAGTAGCTCAGAAGTTTGTGG
AAACTCATCCTGAGTTTATTGGAATCAAAATCATTTATTCGGATCACAGATCCAAAGATGTGGC
TGTCATCGCAGAATCCATCCGAATGGCCATGGGGCTCCGAATCAAGTTCCCCACGGTGGTGGCA
GGGTTTGACCTGGTGGGGCATGAGGACACTGGCCACTCCTTGCATGACTACAAGGAAGCTCTGA
TGATCCCCGCCAAGGATGGCGTTAAGCTGCCTTACTTCTTCCACGCCGGAGAAACAGACTGGCA
GGGTACTTCCATAGACAGGAACATTCTGGATGCTCTGATGCTGGCCACTACCAGAATCGGCCAT
GGATTTGCTTTGAGCAAACACCCCGCAGTCAGGACTTATTCCTGGAAAAAGGACATCCCCATAG
AAGTCTGTCCCATCTCTAACCAGGTGCTGAAACTGGTGTCTGACTTGAGGAACCACCCTGTAGC
CACTCTGATGGCCACTGGGCACCCCATGGTGATCAGCTCTGATGACCCAGCTATGTTTGGTGCC
AAAGGCTTGTCCTATGATTTCTATGAGGTCTTCATGGGCATTGGGGGGATGAAGGCTGATCTGA
GGACCCTCAAACAGCTGGCCATGAACTCTATCAAGTACAGTACCCTGTTGGAGAGTGAGAAAAA
TACTTTCATGGAAATATGGAAGAAGAGATGGGATAAGTTCATAGCAGATGTGGCTACAAAGTGA
SEQ ID NO: 12: ADA2-D441E
ATGCTGGTCGACGGCCCTTCAGAACGGCCTGCTCTGTGCTTCCTGCTGCTGGCTGTCGCAATGA
GCTTCTTTGGTAGTGCCCTGTCCATCGACGAGACCCGGGCCCACCTGCTGCTGAAGGAGAAGAT
GATGAGGCTGGGCGGCAGACTGGTGCTGAACACCAAGGAGGAGCTGGCTAATGAGCGGCTGATG
ACACTGAAGATCGCCGAGATGAAGGAGGCTATGAGGACCCTGATCTTCCCCCCTTCCATGCACT
TCTTTCAAGCCAAGCACCTGATTGAGAGATCTCAGGTGTTTAACATCCTGCGGATGATGCCCAA
GGGCGCCGCTCTGCACTGCACGACATCGGCATCGTGACCATGGATTGGCTGGTGCGGAATGTG
ACATACAGGCCTCACTGCCACATCTGTTTCACCCCACGGGGCATCATGCAGTTCAGATTTGCCC
ACCCAACACCCCGGCCTTCTGAGAAGTGCAGCAAGTGGATCCTGCTGGAGGACTACCGGAAGAG
GGTGCAGAACGTGACCGAGTTCGACGATTCCCTGCTGCGGAACTTCACCCTGGTGACACAGCAC
CCTGAAGTGATCTACACCAACCAGAATGTGGTGTGGTCTAAGTTCGAGACCATCTTCTTTACAA
TCAGCGGCCTGATCCACTACGCCCCAGTGTTCAGAGACTACGTGTTCCGGAGCATGCAGGAGTT
TTACGAGGATAACGTGCTGTATATGGAGATCAGAGCTCGGCTGCTGCCCGTGTACGAGCTGTCC
GGCGAGCACCACGATGAGGAGTGGTCTGTGAAGACCTACCAGGAGGTGGCCCAGAAGTTCGTGG
AGACACACCCCGAGTTTATCGGCATCAAGATCATCTATTCCGACCACCGGTCTAAGGATGTGGC
CGTGATCGCTGAGAGCATCCGGATGGCCATGGGCCTGAGGATCAAGTTCCCTACAGTGGTGGCT
GGCTTTGACCTGGTCGGCCACGAGGATACAGGCCACTCCCTGCACGACTACAAGGAGGCCCTGA
TGATCCCCGCTAAGGATGGCGTGAAGCTGCCTTATTTCTTTCACGCCGGCGAGACCGATTGGCA
GGGCACAAGCATCGACAGGAACATCCTGGATGCTCTGATGCTGAATACCACAAGAATCGGCCAC
GGCTTCGCCCTGAGCAAGCACCCTGCTGTGCGGACCTACTCCTGGAAGAAGGACATCCCAATCG
AGGTGTGCCCCATCTCTAACCAAGTGCTGAAGCTGGTGAGCGATCTGCGGAATCACCCAGTGGC
CACCCTGATGGCTACAGGCCACCCAATGGTCATCAGCTCCGAAGATCCCGCCATGTTTGGCGCT
AAGGGCCTGTCTTACGACTTCTATGAGGTGTTTATGGGCATCGGCGGCATGAAGGCCGATCTGC
GGACCCTGAAGCAGCTGGCTATGAACAGCATCAAGTATTCCACACTGCTGGAGAGCGAGAAGAA
TACATTCATGGAAATCTGGAAGAAACGGTGGGACAAGTTCATCGCTGACGTGGCTACTAAATGA

SEQ ID NO: 14: ADA2-D442A
ATGCTGGTCGACGGCCCTTCAGAACGGCCTGCTCTGTGCTTCCTGCTGCTGGCTGTCGCAATGA

GCTTCTTTGGTAGTGCCCTGTCCATCGACGAGACCCGGGCCCACCTGCTGCTGAAGGAGAAGAT

GATGAGGCTGGGCGGCAGACTGGTGCTGAACACCAAGGAGGAGCTGGCTAATGAGCGGCTGATG

ACACTGAAGATCGCCGAGATGAAGGAGGCTATGAGGACCCTGATCTTCCCCCCTTCCATGCACT

TCTTTCAAGCCAAGCACCTGATTGAGAGATCTCAGGTGTTTAACATCCTGCGGATGATGCCCAA

GGGCGCCGCTCTGCACCTGCACGACATCGGCATCGTGACCATGGATTGGCTGGTGCGGAATGTG

ACATACAGGCCTCACTGCCACATCTGTTTCACCCCACGGGGCATCATGCAGTTCAGATTTGCCC

ACCCAACACCCCGGCCTTCTGAGAAGTGCAGCAAGTGGATCCTGCTGGAGGACTACCGGAAGAG

GGTGCAGAACGTGACCGAGTTCGACGATTCCCTGCTGCGGAACTTCACCCTGGTGACACAGCAC

CCTGAAGTGATCTACACCAACCAGAATGTGGTGTGGTCTAAGTTCGAGACCATCTTCTTTACAA

TCAGCGGCCTGATCCACTACGCCCCAGTGTTCAGAGACTACGTGTTCCGGAGCATGCAGGAGTT

TTACGAGGATAACGTGCTGTATATGGAGATCAGAGCTCGGCTGCTGCCCGTGTACGAGCTGTCC

GGCGAGCACCACGATGAGGAGTGGTCTGTGAAGACCTACCAGGAGGTGGCCCAGAAGTTCGTGG

AGACACACCCCGAGTTTATCGGCATCAAGATCATCTATTCCGACCACCGGTCTAAGGATGTGGC

CGTGATCGCTGAGAGCATCCGGATGGCCATGGGCCTGAGGATCAAGTTCCCTACAGTGGTGGCT

GGCTTTGACCTGGTCGGCCACGAGGATACAGGCCACTCCCTGCACGACTACAAGGAGGCCCTGA

TGATCCCCGCTAAGGATGGCGTGAAGCTGCCTTATTTCTTTCACGCCGGCGAGACCGATTGGCA

GGGCACAAGCATCGACAGGAACATCCTGGATGCTCTGATGCTGAATACCACAAGAATCGGCCAC

GGCTTCGCCCTGAGCAAGCACCCTGCTGTGCGGACCTACTCCTGGAAGAAGGACATCCCAATCG

AGGTGTGCCCCATCTCTAACCAAGTGCTGAAGCTGGTGAGCGATCTGCGGAATCACCCAGTGGC

CACCCTGATGGCTACAGGCCACCCAATGGTCATCAGCTCCGACGCTCCCGCCATGTTTGGCGCT

AAGGGCCTGTCTTACGACTTCTATGAGGTGTTTATGGGCATCGGCGGCATGAAGGCCGATCTGC

GGACCCTGAAGCAGCTGGCTATGAACAGCATCAAGTATTCCACACTGCTGGAGAGCGAGAAGAA

TACATTCATGGAAATCTGGAAGAAACGGTGGGACAAGTTCATCGCTGACGTGGCTACTAAATGA

SEQ ID NO: 16: ADA2-W362G
ATGCTGGTCGACGGCCCTTCAGAACGGCCTGCTCTGTGCTTCCTGCTGCTGGCTGTCGCAATGA

GCTTCTTTGGTAGTGCCCTGTCCATCGACGAGACCCGGGCCCACCTGCTGCTGAAGGAGAAGAT

GATGAGGCTGGGCGGCAGACTGGTGCTGAACACCAAGGAGGAGCTGGCTAATGAGCGGCTGATG

ACACTGAAGATCGCCGAGATGAAGGAGGCTATGAGGACCCTGATCTTCCCCCCTTCCATGCACT

TCTTTCAAGCCAAGCACCTGATTGAGAGATCTCAGGTGTTTAACATCCTGCGGATGATGCCCAA

GGGCGCCGCTCTGCACCTGCACGACATCGGCATCGTGACCATGGATTGGCTGGTGCGGAATGTG

ACATACAGGCCTCACTGCCACATCTGTTTCACCCCACGGGGCATCATGCAGTTCAGATTTGCCC

ACCCAACACCCCGGCCTTCTGAGAAGTGCAGCAAGTGGATCCTGCTGGAGGACTACCGGAAGAG

GGTGCAGAACGTGACCGAGTTCGACGATTCCCTGCTGCGGAACTTCACCCTGGTGACACAGCAC

CCTGAAGTGATCTACACCAACCAGAATGTGGTGTGGTCTAAGTTCGAGACCATCTTCTTTACAA

TCAGCGGCCTGATCCACTACGCCCCAGTGTTCAGAGACTACGTGTTCCGGAGCATGCAGGAGTT

TTACGAGGATAACGTGCTGTATATGGAGATCAGAGCTCGGCTGCTGCCCGTGTACGAGCTGTCC

GGCGAGCACCACGATGAGGAGTGGTCTGTGAAGACCTACCAGGAGGTGGCCCAGAAGTTCGTGG

AGACACACCCCGAGTTTATCGGCATCAAGATCATCTATTCCGACCACCGGTCTAAGGATGTGGC

CGTGATCGCTGAGAGCATCCGGATGGCCATGGGCCTGAGGATCAAGTTCCCTACAGTGGTGGCT

```
GGCTTTGACCTGGTCGGCCACGAGGATACAGGCCACTCCCTGCACGACTACAAGGAGGCCCTGA

TGATCCCCGCTAAGGATGGCGTGAAGCTGCCTTATTTCTTTCACGCCGGCGAGACCGATGGCCA

GGGCACAAGCATCGACAGGAACATCCTGGATGCTCTGATGCTGAATACCACAAGAATCGGCCAC

GGCTTCGCCCTGAGCAAGCACCCTGCTGTGCGGACCTACTCCTGGAAGAAGGACATCCCAATCG

AGGTGTGCCCCATCTCTAACCAAGTGCTGAAGCTGGTGAGCGATCTGCGGAATCACCCAGTGGC

CACCCTGATGGCTACAGGCCACCCAATGGTCATCAGCTCCGACGATCCCGCCATGTTTGGCGCT

AAGGGCCTGTCTTACGACTTCTATGAGGTGTTTATGGGCATCGGCGGCATGAAGGCCGATCTGC

GGACCCTGAAGCAGCTGGCTATGAACAGCATCAAGTATTCCACACTGCTGGAGAGCGAGAAGAA

TACATTCATGGAAATCTGGAAGAAACGGTGGGACAAGTTCATCGCTGACGTGGCTACTAAATGA

SEQ ID NO: 18: ADA2-H112Q
ATGCTGGTCGACGGCCCTTCAGAACGGCCTGCTCTGTGCTTCCTGCTGCTGGCTGTCGCAATGA

GCTTCTTTGGTAGTGCCCTGTCCATCGACGAGACCCGGGCCCACCTGCTGCTGAAGGAGAAGAT

GATGAGGCTGGGCGGCAGACTGGTGCTGAACACCAAGGAGGAGCTGGCTAATGAGCGGCTGATG

ACACTGAAGATCGCCGAGATGAAGGAGGCTATGAGGACCCTGATCTTCCCCCCTTCCATGCACT

TCTTTCAAGCCAAGCACCTGATTGAGAGATCTCAGGTGTTTAACATCCTGCGGATGATGCCCAA

GGGCGCCGCTCTGCAACTGCACGACATCGGCATCGTGACCATGGATTGGCTGGTGCGGAATGTG

ACATACAGGCCTCACTGCCACATCTGTTTCACCCCACGGGGCATCATGCAGTTCAGATTTGCCC

ACCCAACACCCCGGCCTTCTGAGAAGTGCAGCAAGTGGATCCTGCTGGAGGACTACCGGAAGAG

GGTGCAGAACGTGACCGAGTTCGACGATTCCCTGCTGCGGAACTTCACCCTGGTGACACAGCAC

CCTGAAGTGATCTACACCAACCAGAATGTGGTGTGGTCTAAGTTCGAGACCATCTTCTTTACAA

TCAGCGGCCTGATCCACTACGCCCCAGTGTTCAGAGACTACGTGTTCCGGAGCATGCAGGAGTT

TTACGAGGATAACGTGCTGTATATGGAGATCAGAGCTCGGCTGCTGCCCGTGTACGAGCTGTCC

GGCGAGCACCACGATGAGGAGTGGTCTGTGAAGACCTACCAGGAGGTGGCCCAGAAGTTCGTGG

AGACACACCCCGAGTTTATCGGCATCAAGATCATCTATTCCGACCACCGGTCTAAGGATGTGGC

CGTGATCGCTGAGAGCATCCGGATGGCCATGGGCCTGAGGATCAAGTTCCCTACAGTGGTGGCT

GGCTTTGACCTGGTCGGCCACGAGGATACAGGCCACTCCCTGCACGACTACAAGGAGGCCCTGA

TGATCCCCGCTAAGGATGGCGTGAAGCTGCCTTATTTCTTTCACGCCGGCGAGACCGATTGGCA

GGGCACAAGCATCGACAGGAACATCCTGGATGCTCTGATGCTGAATACCACAAGAATCGGCCAC

GGCTTCGCCCTGAGCAAGCACCCTGCTGTGCGGACCTACTCCTGGAAGAAGGACATCCCAATCG

AGGTGTGCCCCATCTCTAACCAAGTGCTGAAGCTGGTGAGCGATCTGCGGAATCACCCAGTGGC

CACCCTGATGGCTACAGGCCACCCAATGGTCATCAGCTCCGACGATCCCGCCATGTTTGGCGCT

AAGGGCCTGTCTTACGACTTCTATGAGGTGTTTATGGGCATCGGCGGCATGAAGGCCGATCTGC

GGACCCTGAAGCAGCTGGCTATGAACAGCATCAAGTATTCCACACTGCTGGAGAGCGAGAAGAA

TACATTCATGGAAATCTGGAAGAAACGGTGGGACAAGTTCATCGCTGACGTGGCTACTAAATGA
```

Moreover, a nucleic acid molecule encompassing all or a portion of the nucleic acids of the invention can be isolated by the polymerase chain reaction (PCR) using synthetic oligonucleotide primers designed based upon the sequence of the nucleic acids of the invention.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ADA2 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, or a portion of the nucleotide sequence.

In another preferred embodiment, an isolated nucleic acid molecule of the invention comprises a nucleic acid molecule which is a complement of the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, or a portion of any of these nucleotide sequences. A nucleic acid molecule which is complementary to the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, is one which is sufficiently complementary to the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, such that it can hybridize to the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99% or more identical to the entire length of the nucleotide sequence shown in SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, or a portion of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26.

Moreover, the nucleic acid molecule of the invention can comprise only a portion of the nucleic acid sequence of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, for example a fragment which can be used as a probe or primer or a fragment encoding a biologically active portion of an ADA2 protein. The nucleotide sequence determined from the cloning of the ADA2 gene allows for the generation of probes and primers designed for use in identifying and/or cloning other ADA2 family members, as well as ADA2 homologues from other species.

The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, of an anti-sense sequence of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, or of a naturally occurring allelic variant or mutant of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26. In an exemplary embodiment, a nucleic acid molecule of the present invention comprises a nucleotide sequence which is 350-400, 400-450, 450-500, 500-550, 550-600, 600-650, 650-700, 700-750, 750-800, 800-850, 850-900, 949, 950-1000, or more nucleotides in length and hybridizes under stringent hybridization conditions to a nucleic acid molecule of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26.

Probes based on the ADA2 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express an ADA2 protein, such as by measuring a level of an ADA2-encoding nucleic acid in a sample of cells from a subject e.g., detecting ADA2 mRNA levels or determining whether a genomic ADA2 gene has been mutated or deleted.

A nucleic acid fragment encoding a "biologically active portion of an ADA2 protein" can be prepared by isolating a portion of the nucleotide sequence of SEQ ID NO:2 or SEQ ID NO:36, which encodes a polypeptide having ADA2 biological activity (the biological activities of the ADA2 proteins and fusion proteins of the invention are described herein), expressing the encoded portion of the ADA2 protein (e.g., by recombinant expression in vitro) and assessing the activity of the encoded portion of the ADA2 protein.

The invention further encompasses nucleic acid molecules that differ from the nucleotide sequence shown in SEQ ID NO:2 due to degeneracy of the genetic code and thus encode the same ADA2 proteins as those encoded by the nucleotide sequence shown in SEQ ID NO:2. For example, SEQ ID NO:36 differs from SEQ ID NO:2 due to degeneracy of the genetic code, but still encodes the same ADA2 protein as SEQ ID NO:2.

In addition to the ADA2 nucleotide sequence of SEQ ID NOs:2 and 36, it will be appreciated by those skilled in the art that DNA sequence polymorphisms that lead to changes in the amino acid sequences of the ADA2 proteins may exist within a population (e.g., the human population). Such genetic polymorphism in the ADA2 genes may exist among individuals within a population due to natural allelic variation. As used herein, the terms "gene" and "recombinant gene" refer to nucleic acid molecules which include an open reading frame encoding an ADA2 protein, preferably a mammalian ADA2 protein, preferably a human ADA2 protein, and can further include non-coding regulatory sequences, and introns.

Allelic variants of human ADA2 include both functional and non-functional ADA2 proteins. Functional allelic variants are naturally occurring amino acid sequence variants of the human ADA2 protein that maintain the ability to bind an ADA2 ligand and/or modulate any of the ADA2 activities described herein. Functional allelic variants will typically contain only conservative substitution of one or more amino acids of SEQ ID NO:2 or SEQ ID NO:36 or substitution, deletion or insertion of non-critical residues in non-critical regions of the protein.

Non-functional allelic variants are naturally occurring amino acid sequence variants of the human ADA2 protein that do not have the ability to either bind an ADA2 interaction molecule and/or modulate any of the ADA2 activities described herein, including but not limited to increasing differentiation of monocytes into macrophages, e.g., M2 macrophages, e.g., M2a macrophages, M2b macrophages or M2c macrophages, stimulating CD4+ T cell proliferation, and increasing endothelial cell development. Non-functional allelic variants will typically contain a non-conservative substitution, a deletion, or insertion or premature truncation of the amino acid sequence of SEQ ID NO:2 or SEQ ID NO:36 or a substitution, insertion or deletion in critical residues or critical regions.

The present invention further provides non-human orthologues of the human ADA2 protein. Orthologues of the human ADA2 protein are proteins that are isolated from non-human organisms and possess the same ADA2 receptor binding and/or modulation of ADA2-mediated activities of the human ADA2 protein, including but not limited to, increasing differentiation of monocytes into macrophages, e.g., M2 macrophages, e.g., M2a macrophages, M2b macrophages or M2c macrophages, stimulating CD4+ T cell proliferation, and increasing endothelial cell development. Orthologues of the human ADA2 protein can readily be identified as comprising an amino acid sequence that is substantially identical to SEQ ID NO:2.

Moreover, nucleic acid molecules encoding other ADA2 family members and, thus, which have a nucleotide sequence which differs from the ADA2 sequences of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, are intended to be within the scope of the invention. For example, another ADA2 cDNA can be identified based on the nucleotide sequence of human ADA2. Moreover, nucleic acid molecules encoding ADA2 proteins from different species, and thus which have a nucleotide sequence which differs from the ADA2 sequence of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26, are intended to be within the scope of the invention. For example, a mouse ADA2 cDNA can be identified based on the nucleotide sequence of a human ADA2.

Nucleic acid molecules corresponding to natural allelic variants and homologues of the ADA2 cDNAs of the invention can be isolated based on their homology to the ADA2 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:2, SEQ ID NO:20, SEQ ID NO:22, SEQ ID NO:24, SEQ ID NO:36, SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:26. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other.

Such stringent conditions are known to those skilled in the art and can be found in Current Protocols in Molecular Biology, Ausubel et al., eds., John Wiley & Sons, Inc. (1995), sections 2, 4, and 6. Additional stringent conditions can be found in Molecular Cloning: A Laboratory Manual, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C., are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) Proc. Natl. Acad. Sci. USA 81:1991-1995), or alternatively 0.2×SSC, 1% SDS.

Preferably, an isolated nucleic acid molecule of the invention that hybridizes under stringent conditions to the sequence of SEQ ID NO:2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the ADA2 sequences that may exist in the population, the skilled artisan will further appreciate that changes can be introduced by mutation into the nucleotide sequences of SEQ ID NO:2 or SEQ ID NO:36, thereby leading to changes in the amino acid sequence of the encoded ADA2 proteins, without altering the functional ability of the ADA2 proteins. For example, nucleotide substitutions leading to amino acid substitutions at "non-essential" amino acid residues can be made in the sequence of SEQ ID NO:2 or SEQ ID NO:36. A "non-essential" amino acid residue is a residue that can be altered from the wild-type sequence of ADA2 (e.g., the sequence of SEQ ID NO:2) without altering the biological activity, whereas an "essential" amino acid residue is required for biological activity. For example, amino acid residues that are conserved among the ADA2 proteins of the present invention, are predicted to be particularly unamenable to alteration. Furthermore, additional amino acid residues that are conserved between the ADA2 proteins of the present invention and other members of the ADA2 family of proteins are not likely to be amenable to alteration.

Accordingly, another aspect of the invention pertains to nucleic acid molecules encoding ADA2 proteins that contain changes in amino acid residues that are not essential for activity. Such ADA2 proteins differ in amino acid sequence from SEQ ID NO:1, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:1.

An isolated nucleic acid molecule encoding an ADA2 protein homologous to the protein of SEQ ID NO:1 can be created by introducing one or more nucleotide substitutions, additions or deletions into the nucleotide sequence of SEQ ID NO: 2 such that one or more amino acid substitutions, additions or deletions are introduced into the encoded protein. Mutations can be introduced into SEQ ID NO:2 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an ADA2 protein is preferably replaced with another amino acid residue from the same side chain family. Alternatively, in another embodiment, mutations can be introduced randomly along all or part of an ADA2 coding sequence, such as by saturation mutagenesis, and the resultant mutants can be screened for ADA2 biological activity to identify mutants that retain activity. Following mutagenesis of SEQ ID NO:2 or SEQ ID NO:36, the encoded protein can be expressed recombinantly and the activity of the protein can be determined.

In a preferred embodiment, a mutant ADA2 protein or ADA2 fusion protein can be assayed for deaminase activity, the ability to increase differentiation of monocytes into macrophages, e.g., M2 macrophages, e.g., M2a macrophages, M2b macrophages or M2c macrophages, stimulate CD4+ T cell proliferation, and/or increase endothelial cell development.

In yet another embodiment, the ADA2 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. US. 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

III. Recombinant Expression Vectors and Host Cells

Another aspect of the invention pertains to vectors, preferably expression vectors, containing a nucleic acid encoding an ADA2 protein (or a portion thereof), or an ADA2 fusion protein. ADA2 proteins, functional fragments thereof, and fusion proteins can be produced from transgenic animals (e.g., cow, sheep, goat and birds), insect cells, plants, yeast or bacteria as known in the art using the methods described herein.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ADA2 proteins, ADA2 protein fragments, ADA2 fusion proteins, and the like).

The recombinant expression vectors of the invention can be designed for expression of ADA2 proteins and fusions in prokaryotic or eukaryotic cells. For example, ADA2 proteins and fusions can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified ADA2 proteins or ADA2 fusion proteins can be utilized in ADA2 activity assays, (e.g., direct assays or competitive assays described in detail herein), or to generate antibodies specific for ADA2 proteins, for example.

Examples of suitable inducible non-fusion E. coli expression vectors include pTrc (Amann et al., (1988) Gene 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

In another embodiment, the ADA2 expression vector is a yeast expression vector. Examples of vectors for expression in yeast S. cerivisae include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, ADA2 proteins and fusion proteins can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170: 31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Suitable mammalian cells that can be used to obtain ADA2 proteins, fusion proteins, or functional fragments include primary cell cultures derived from a mammal at any stage of development or maturity. Mammalian cells also include cells of mammalian origin that have been transformed to divide for an unlimited number of generation, such as human embryonic kidney line (e.g., HEK293), human fibrosarcoma cell line (e.g., HT1080), human cervical carcinoma cells (HeLa), human lung cells (W138), human liver cells (Hep G2), human retinoblasts, BALB/c mouse myeloma line, COS-7, baby hamster kidney cells (e.g., BHK), Chinese hamster ovary cells (e.g., CHO+/−DHFR), mouse Sertoli cells (TM4), rat liver cells (BRL 3A), mouse mammary tumor (e.g., MMT-060562), TRI cells; MRC 5 cells, FS4 cells, monkey kidney cells (e.g., CV1, VERO-76), canine kidney cells (e.g., MDCK). Different host cells can be chosen to ensure its capacity to modify and process ADA2 proteins, fusion proteins, or functional fragments thereof.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ADA2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ADA2 protein or fusion protein can be expressed in bacterial cells such as E. coli, insect cells, yeast or mammalian cells (such as Chinese hamster ovary cells (CHO) or COS cells), or avian cells. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an ADA2 protein or fusion protein or can be introduced on a separate vector. Cells stably transfected with the introduced nucleic acid can be identified by drug selection (e.g., cells that have incorporated the selectable marker gene will survive, while the other cells die).

The present invention also contemplates production of ADA2, ADA2 variants, ADA2 functional fragments, or ADA2 fusions in a transgenic avian system. When an avian expression system is used, the vectors described in U.S. Pat. Nos. 6,730,822; 6,825,396; 6,875,588; 7,294,507; 7,521,591; 7,534,929; and U.S. Patent Publication No. 2006/0185024, the entire contents of each of which are incorporated herein by reference, are preferred. The present invention includes production of ADA2, ADA2 functional fragments, or ADA2 fusions with or without a second moiety (e.g., targeting or proteolytic cleavage sequence). The avian expression vector can include one or more regulatory sequences such as oviduct-specific promoter, for example, and without limitation, ovomucoid promoters, ovalbumin promoters, lysozyme promoters, conalbumin promoters, ovomucin promoters, ovotransferrin promoters and functional portions of each of these promoters. Suitable non-specific promoters can include, for example and without limitation, cytomegalovirus (CMV) promoters, MDOT promoters and Rous-sarcoma virus (RSV) promoters, murine leukemia virus (MLV) promoters, mouse mammary tumor virus (MMTV) promoters and SV40 promoters and functional portions of each of these promoters. Non-limiting examples of other promoters which can be useful in the present invention include, without limitation, Pol III promoters (for example, type 1, type 2 and type 3 Pol III promoters) such as H1 promoters, U6 promoters, tRNA promoters, RNase MPR promoters and functional portions of each of these promoters. Typically, functional terminator sequences are selected for use in accordance with the promoter that is employed.

A host cell of the invention, such as a prokaryotic or eukaryotic host cell in culture, can be used to produce (i.e., express) an ADA2 protein or fusion protein. Accordingly, the invention further provides methods for producing an ADA2 protein or ADA2 fusion protein using the host cells of the invention. In one embodiment, the method comprises culturing the host cell of invention (into which a recombinant expression vector encoding an ADA2 protein or an ADA2 fusion protein has been introduced) in a suitable medium such that an ADA2 protein or ADA2 fusion protein is produced. In another embodiment, the method further comprises isolating an ADA2 protein or an ADA2 fusion protein from the medium or the host cell.

The host cells of the invention can also be used to produce non-human transgenic animals. For example, in one embodiment, a host cell of the invention is a fertilized oocyte or an embryonic stem cell into which ADA2-coding sequences have been introduced. Such host cells can then be used to create non-human transgenic animals in which exogenous ADA2 sequences have been introduced into their genome or homologous recombinant animals in which endogenous ADA2 sequences have been altered. Such animals are useful for studying the function and/or activity of an ADA2 and for identifying and/or evaluating modulators of ADA2 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ADA2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an ADA2-encoding nucleic acid into the male pronuclei of a fertilized oocyte, e.g., by microinjection, retroviral infection, and allowing the oocyte to develop in a pseudopregnant female foster animal. The ADA2 cDNA sequence can be introduced as a transgene into the genome of a non-human animal. Alternatively, a nonhuman homologue of a human ADA2 gene, such as a mouse or rat ADA2 gene, can be used as a transgene. Alternatively, an ADA2 gene homologue, such as another ADA2 family member, can be isolated based on hybridization to the ADA2 cDNA sequences or the DNA insert of the plasmid and used as a transgene. Intronic sequences and polyadenylation signals can also be included in the transgene to increase the efficiency of expression of the transgene. A tissue-specific regulatory sequence(s) can be operably linked to an ADA2 transgene to direct expression of an ADA2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of an ADA2 transgene in its genome and/or expression of ADA2 mRNA in tissues or cells of the animals. A transgenic founder animal can then be used to breed additional animals carrying the transgene. Moreover, transgenic animals carrying a transgene encoding an ADA2 protein or an ADA2 fusion protein can further be bred to other transgenic animals carrying other transgenes.

To create a homologous recombinant animal, a vector is prepared which contains at least a portion of an ADA2 gene into which a deletion, addition or substitution has been introduced to thereby alter, e.g., functionally disrupt, the ADA2 gene. The ADA2 gene can be a human gene, but more preferably, is a non-human homologue of a human ADA2 gene. For example, a mouse ADA2 gene can be used to construct a homologous recombination vector suitable for altering an endogenous ADA2 gene in the mouse genome. In a preferred embodiment, the vector is designed such that, upon homologous recombination, the endogenous ADA2 gene is functionally disrupted (i.e., no longer encodes a functional protein; also referred to as a "knock out" vector). Alternatively, the vector can be designed such that, upon homologous recombination, the endogenous ADA2 gene is mutated or otherwise altered but still encodes functional protein (e.g., the upstream regulatory region can be altered to thereby alter the expression of the endogenous ADA2 protein). In the homologous recombination vector, the altered portion of the ADA2 gene is flanked at its 5' and 3' ends by additional nucleic acid sequence of the ADA2 gene to allow for homologous recombination to occur between the exogenous ADA2 gene carried by the vector and an endogenous ADA2 gene in an embryonic stem cell. The additional flanking ADA2 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced ADA2 gene has homologously recombined with the endogenous ADA2 gene are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In a specific embodiment of the invention, ADA2 deficient zebrafish can be created, for example, as described in Zhou et al., 2014, N. Engl. J. Med., 370(10):911-920.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The present invention further provides preparations and formulations comprising the isolated human ADA2 proteins (and biologically active fragments thereof) and ADA2 fusion proteins of the present invention. It should be understood that any of the isolated human ADA2 proteins and ADA2 fusion proteins described herein, including ADA2 biologically active fragments having any one or more of the structural and functional features described in detail throughout the application, may be formulated or prepared as described herein. When various formulations are described in this section as including an ADA2 protein, it is understood that such an protein may be an ADA2 protein, an ADA2 fusion protein, an ADA2 biologically active fragment, or an ADA2 protein fragment fusion having any one or more of the characteristics of the ADA2 proteins and fusion proteins described herein.

The ADA2 proteins, fragments of ADA2 proteins, and ADA2 fusion proteins of the invention (also referred to herein as "active compounds") can be incorporated into pharmaceutical compositions suitable for administration. Such compositions typically comprise the nucleic acid molecule, protein, or antibody and a pharmaceutically acceptable carrier.

As used herein, the term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the ADA2 proteins and ADA2 protein fusions of the present invention, and with each other, in a manner such that there is no interaction which would substantially impair the desired pharmaceutical efficacy.

The formulations of the invention are present in a form known in the art and acceptable for therapeutic uses. In one embodiment, a formulation of the invention is a liquid formulation. In another embodiment, a formulation of the invention is a lyophilized formulation. In a further embodiment, a formulation of the invention is a reconstituted liquid formulation. In one embodiment, a formulation of the invention is a stable liquid formulation. In one embodiment, a liquid formulation of the invention is an aqueous formulation. In another embodiment, the liquid formulation is non-aqueous. In a specific embodiment, a liquid formulation of the invention is an aqueous formulation wherein the aqueous carrier is distilled water.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ADA2 protein, an ADA2 fusion protein, or an ADA2 protein fragment) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compositions of the invention are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The composition can also be prepared in the form of suppositories (e.g., with conventional suppository bases such as cocoa butter and other glycerides) or retention enemas for rectal delivery.

In one embodiment, the active compounds of the invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

In normal adults, the active ADA2 protein is available in the plasma about 80 to 150 ng/mL, whereas 150-250 ng/mL is available in normal pediatric population. Patients suffering from ADA deficiency exhibit significantly low plasma ADA2 activity, e.g., less than 25 ng/mL in the plasma, whereas carriers of a loss-of-function mutation exhibit 25-80 ng/mL of active ADA2 protein in the plasma. In one embodiment, the ADA2 fusion protein of the invention, when administered in an effective amount, increases the plasma ADA2 activity at least up to 80 ng/mL.

In one embodiment, the ADA2 protein of the present invention elicits macrophage proliferation and differentiation having an M2c phenotype. The macrophage exhibits CD163 expression.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions of the invention may be prepared for storage by mixing the isolated human ADA2 protein (or functional fragment thereof) or ADA2 fusion protein having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (*Remington's Pharmaceutical Sciences*, 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The pharmaceutical compositions of the invention comprising an isolated human ADA2 protein (or functional fragment thereof) or an ADA2 fusion protein may further comprise one or more active compounds as necessary for the particular indication being treated, preferably those with complementary activities that do not adversely affect each other. Such additional active compound(s) is/are suitably present in combination in amounts that are effective for the purpose intended.

The pharmaceutical compositions can be included in a container, pack, or dispenser together with instructions for administration.

V. Uses and Methods of ADA2 Proteins and ADA2 Fusion Proteins of the Invention

The ADA2 proteins, ADA2 fusion proteins, ADA2 nucleic acid molecules, and ADA2 antibodies described herein can be used in one or more of the following methods: a) ADA2 assays; b) predictive medicine (e.g., diagnostic assays, prognostic assays, monitoring clinical trials, and pharmacogenetics); and c) methods of treatment (e.g., therapeutic and prophylactic).

As described herein, an ADA2 protein or ADA2 fusion protein of the invention has one or more of the following activities: increases differentiation of monocytes into macrophages, e.g., M2 macrophages, e.g., M2a macrophages, M2b macrophages or M2c macrophages, stimulates CD4+ T cell proliferation, and increases endothelial cell development.

The isolated nucleic acid molecules of the invention can be used, for example, to express ADA2 protein or ADA2 fusion protein (e.g., via a recombinant expression vector in a host cell in gene therapy applications), to detect ADA2 mRNA (e.g., in a biological sample) or a genetic alteration in an ADA2 gene, and to modulate ADA2 activity, as described further below. The ADA2 proteins and ADA2 fusion proteins of the invention can be used to treat disorders characterized by insufficient production of ADA2. In addition, the ADA2 proteins and ADA2 fusion proteins can be used to screen for naturally occurring ADA2 substrates, to screen for drugs or compounds which modulate ADA2 activity, as well as to treat disorders characterized by insufficient or excessive production of ADA2 protein or production of ADA2 protein forms which have decreased or aberrant activity compared to ADA2 wild type protein (e.g., disorders such as polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM).

A. ADA2 Activity Assays

The invention provides a method (also referred to herein as a "screening assay") for determining the activity of an ADA2 protein, or biologically active fragment, or ADA2 fusion protein including, for example, the differentiation of monocytes into macrophages, e.g., M2 macrophages, e.g., M2a macrophages, M2b macrophages or M2c macrophages, the stimulation CD4+ T cell proliferation, and endothelial cell development.

Screening assays to determine ADA2 protein or ADA2 fusion protein adenosine deaminase activity in cell culture medium and cell lysates is known in the art (see, for example, Zavialov et al., 2005, Biochem. J., 391:51-57). To briefly summarize, a reaction mixture comprising adenosine and the ADA1 inhibitor EHNA are added with cell culture medium and cell lysates. The protein precipitate can be separated by centrifugation, and the supernatant can be run on an XK 16/20 column. The peaks of inosine and adenosine can then be subsequently eluted from the column, and the chromatography and the peak area analysis can be performed. The ADA activity in units/1 can be determined using the following formula:

$$1 \text{ unit}/1 = S_{inosine}/(S_{inosine} + S_{adenosine}/f)k_{dilution} C_M k_{correction} \times 10^6/\tau (\mu mol \times min^{-1} \times l^{-1}),$$

where $S_{inosine}$ and $S_{adenosine}$ are the areas of inosine and adenosine peaks; f=1.347 is the ratio between adenosine and inosine molar absorbance coefficients at 254 nm; $k_{dilution}$ is a dilution coefficient ($V_{sample}/V_{reaction\ mix}$); $C_M$ is the adenosine concentration in the reaction mixture (M); $k_{correction}=1+K_m/C_M$ is the difference between the maximal reaction rate at a saturating adenosine concentration and the observed reaction rate at the give adenosine concentration in the reaction mixture ($V_{max}/V_{experimental}$); and τ is the incubation time in minutes.

Screening assays to determine ADA2 protein and ADA2 fusion protein binding to cells are also known in the art (see, for example, Zavialov et al., J. Leukocyte Biol., 88:279-290, 2014). For example, cells can be stained with ADA2 by incubation with 32 nM ADA2-streptavidin-PE in 100 ul FACS buffer, and the binding of ADA2 to cells can be analyzed via flow cytometry.

Screening assays to determine the effect of ADA2 proteins or ADA2 fusion proteins on T cell proliferation are also known in the art. See, for example, Zavialov et al., J. Leukocyte Biol., 88:279-290, 2014. To briefly summarize, fresh peripheral blood can be isolated from a subject. Total T cells, CD4+ cells and CD14+ monocytes and be purified, stained, and analyzed via flow cytometry.

Screening assays to determine the effect of ADA2 proteins or ADA2 fusion proteins of the invention on the differentiation of monocytes are also known in the art. See, for example, Zavialov et al., J. Leukocyte Biol., 88:279-290, 2014. To briefly summarize, CD4+ T cells and CD14+ monocytes can be isolated from PBMCs using a kit from Iltenyi Biotech, labeled, and analyzed via flow cytometry. Viability of macrophages can be assessed by staining the cells with a BD PharMingen Annexin V apoptosis detection kit, and visualizing them using microscopy.

Assays to determine the effect of ADA2 proteins or ADA2 fusion proteins of the invention on macrophage phenotype are also commonly known in the art (see, for example, Novak and Koh, J. Leukocyte Biol., 93:875-881, 2013). For example, the macrophage M2a phenotype is associated with the markers: CD163, CD206, CD209, SR-A1, Dectin-1, DCL-1, IGF-1, FGL2, TGF-β, CCL13, CCL14, CCL17, CCL18, CCL23 and CCL26. The macrophage M2b phenotype is associated with the markers: IL-10, CCL1, CCL20, CXCL1, CXCL2 and CXCL3. The macrophage M2c phenotype is associated with markers: CD163, IL-21R, TLR1, TLR8 and CCL18. Flow-cytometry can be used to determine the phenotype of the macrophage after incubation with the ADA2 protein or ADA2 fusion protein of the invention using any one or combination of the markers listed above. Alternatively, RT-PCR can be used to determine the phenotype of the macrophage after incubation with the ADA2 protein or ADA2 fusion protein of the invention using any of the markers, or any combination of the markers, listed above.

B. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining ADA2 protein/fusion protein and/or nucleic acid expression as well as ADA2 activity, in the context of a biological sample (e.g., blood, serum, cells, tissue) to thereby determine whether an individual is afflicted with a disease or disorder, or is at risk of developing a disorder, associated with aberrant ADA2 expression or activity. The invention also provides for prognostic (or predictive) assays for determining whether an individual is at risk of developing a disorder associated with ADA2 protein, nucleic acid expression or activity. For example, mutations in an ADA2 gene can be assayed in a biological sample. Such assays can be used for prognostic or predictive purpose to thereby phophylactically treat an individual prior to the onset of a disorder characterized by or associated with ADA2 protein, nucleic acid expression or activity.

Another aspect of the invention pertains to monitoring the influence of agents (e.g., drugs, compounds) on the expression or activity of ADA2 in clinical trials.

These and other agents are described in further detail in the following sections.

1. Diagnostic Assays

An exemplary method for detecting the presence or absence of ADA2 protein or nucleic acid in a biological sample involves obtaining a biological sample from a test subject and contacting the biological sample with a compound or an agent capable of detecting ADA2 protein or nucleic acid (e.g., mRNA, genomic DNA) that encodes ADA2 protein such that the presence of ADA2 protein or nucleic acid is detected in the biological sample. A preferred agent for detecting ADA2 mRNA or genomic DNA is a labeled nucleic acid probe capable of hybridizing to ADA2 mRNA or genomic DNA. The nucleic acid probe can be, for example, a full-length ADA2 nucleic acid, or a portion thereof, such as an oligonucleotide of at least 15, 30, 50, 100, 250 or 500 nucleotides in length and sufficient to specifically hybridize under stringent conditions to ADA2 mRNA or genomic DNA. Other suitable probes for use in the diagnostic assays of the invention are described herein.

A preferred agent for detecting ADA2 protein is an antibody capable of binding to ADA2 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect ADA2 mRNA, protein, or genomic DNA in a biological sample in vitro as well as in vivo. For example, in vitro techniques for detection of ADA2 mRNA include Northern hybridizations and in situ hybridizations. In vitro techniques for detection of ADA2 protein include enzyme linked immunosorbent assays (ELISAs), Western blots, immunoprecipitations and immunofluorescence. In vitro techniques for detection of ADA2 genomic DNA include Southern hybridizations. Furthermore, in vivo techniques for detection of ADA2 protein include introducing into a subject a labeled anti-ADA2 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting ADA2 protein, mRNA, or genomic DNA, such that the presence of ADA2 protein, mRNA or genomic DNA is detected in the biological sample, and comparing the presence of ADA2 protein, mRNA or genomic DNA in the control sample with the presence of ADA2 protein, mRNA or genomic DNA in the test sample.

The invention also encompasses kits for detecting the presence of ADA2 in a biological sample. For example, the kit can comprise a labeled compound or agent capable of detecting ADA2 protein or mRNA in a biological sample; means for determining the amount of ADA2 in the sample; and means for comparing the amount of ADA2 in the sample with a standard. The compound or agent can be packaged in a suitable container. The kit can further comprise instructions for using the kit to detect ADA2 protein or nucleic acid.

2. Prognostic Assays

The methods described herein can furthermore be utilized to identify subjects having or at risk of developing an ADA2-associated disease or disorder associated with aberrant ADA2 expression or activity. For example, the assays described herein, such as the preceding diagnostic assays or the following assays, can be utilized to identify a subject having or at risk of developing an ADA2-associated disease or disorder characterized by a misregulation in ADA2 protein activity or nucleic acid expression, such as polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM.

Alternatively, the prognostic assays can be utilized to identify a subject having or at risk for developing an ADA2-associated disease or disorder characterized by a misregulation in ADA2 protein activity or nucleic acid expression. Thus, the present invention provides a method for identifying a disease or disorder associated with aberrant ADA2 expression or activity in which a test sample is obtained from a subject and ADA2 protein or nucleic acid (e.g., mRNA or genomic DNA) is detected, wherein the presence of ADA2 protein or nucleic acid is diagnostic for a subject having or at risk of developing a disease or disorder associated with aberrant ADA2 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an ADA2 protein or an ADA2 fusion protein to treat a disease or disorder associated with aberrant ADA2 expression or activity. Thus, the present invention provides methods for determining whether a subject can be effectively treated with an agent for a disorder associated with aberrant ADA2 expression or activity in which a test sample is obtained and ADA2 protein or nucleic acid expression or activity is detected (e.g., wherein the abundance of ADA2 protein or nucleic acid expression or activity is diagnostic for a subject that can be administered the agent to treat a disorder associated with aberrant ADA2 expression or activity).

The methods of the invention can also be used to detect genetic alterations in an ADA2 gene, thereby determining if a subject with the altered gene is at risk for a disorder characterized by misregulation in ADA2 protein activity or nucleic acid expression. In preferred embodiments, the methods include detecting, in a sample of cells from the subject, the presence or absence of a genetic alteration characterized by at least one of an alteration affecting the integrity of a gene encoding an ADA2 protein, or the mis-expression of the ADA2 gene. For example, such genetic alterations can be detected by ascertaining the existence of at least one of 1) a deletion of one or more nucleotides from a, ADA2 gene; 2) an addition of one or more nucleotides to an ADA2 gene; 3) a substitution of one or more nucleotides of an ADA2 gene, 4) a chromosomal rearrangement of an ADA2 gene; 5) an alteration in the level of a messenger RNA transcript of an ADA2 gene, 6) aberrant modification of an ADA2 gene, such as of the methylation pattern of the genomic DNA, 7) the presence of a non-wild type splicing pattern of a messenger RNA transcript of an ADA2 gene, 8) a non-wild type level of an ADA2-protein, 9) allelic loss of a, ADA2 gene, and 10) inappropriate post-translational modification of an ADA2 protein. As described herein, there are a large number of assays known in the art which can be used for detecting alterations in an ADA2 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the ADA2 gene (see Abravaya et al. (1995) Nucleic Acids Res 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to an ADA2 gene under conditions such that hybridization and amplification of the ADA2 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al., (1990) Proc. Natl. Acad. Sci. USA 87:1874-1878), transcriptional amplification system (Kwoh, D. Y. et al., (1989) Proc. Natl. Acad. Sci.

USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ADA2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in ADA2 can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in ADA2 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the ADA2 gene and detect mutations by comparing the sequence of the sample ADA2 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the ADA2 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes of formed by hybridizing (labeled) RNA or DNA containing the wild-type ADA2 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with 51 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ADA2 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an ADA2 sequence, e.g., a wild-type ADA2 sequence, is hybridized to a cDNA or other DNA product from a test cell(s). The duplex is treated with a DNA mismatch repair enzyme, and the cleavage products, if any, can be detected from electrophoresis protocols or the like. See, for examples U.S. Pat. No. 5,459,039.

In other embodiments, alterations in electrophoretic mobility will be used to identify mutations in ADA2 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat. Res. 285:125-144; and Hayashi (1992) Genet. Anal. Tech. Appl. 9:73-79). Single-stranded DNA fragments of sample and control ADA2 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an ADA2 gene.

Furthermore, any cell type or tissue in which ADA2 is expressed may be utilized in the prognostic assays described herein.

3. Monitoring of Effects During Clinical Trials

Monitoring the influence of an ADA2 protein or an ADA2 fusion protein agent can be applied not only in basic drug screening, but also in clinical trials. For example, the effectiveness of an ADA2 protein or an ADA2 fusion protein described herein to upregulate ADA2 activity in a subject, can be monitored in clinical trials of subjects exhibiting decreased ADA2 gene expression, protein levels, or down-regulated ADA2 activity. In such clinical trials, the expression or activity of genes downstream from ADA2, and preferably, other genes that have been implicated in, for example, ADA2-associated diseases and disorders can be used as a "read out" or markers of the phenotype of a particular cell.

For example, and not by way of limitation, genes that are modulated in cells by treatment with an ADA2 protein or an ADA2 fusion protein which increase ADA2 activity (e.g., identified in a screening assay as described herein) can be identified. Thus, to study the effect of ADA2 proteins and ADA2 fusion proteins on ADA2-associated disorders, for example, in a clinical trial, cells can be isolated and RNA prepared and analyzed for the levels of expression of ADA2 and other genes implicated in the ADA2-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of ADA2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an ADA2 protein or an ADA2 fusion protein including the steps of (i) obtaining a pre-administration sample from a subject prior to administration of the agent; (ii) detecting the level of expression of ADA2 protein, mRNA, or genomic DNA in the preadministration sample, or detecting the level of activity of the ADA2 protein in the preadministration sample; (iii) obtaining one or more post-administration samples from the subject; (iv) detecting the level of expression or level of activity of the ADA2 protein, mRNA, or genomic DNA in the post-administration samples; (v) comparing the level of expression or level activity in the pre-administration sample with the post administration sample or samples; and (vi) altering the administration of the ADA2 protein or ADA2 fusion protein to the subject accordingly. For example, increased administration of the agent may be desirable to increase the activity of ADA2 to higher levels than detected, i.e., to increase the effectiveness of the ADA2 protein or ADA2 fusion protein. Alternatively, decreased administration of the agent may be desirable to decrease expression or activity of ADA2 to lower levels than detected, i.e. to decrease the effectiveness of the ADA2 protein or ADA2 fusion protein. According to such an embodiment, ADA2 activity may be used as an indicator of the effectiveness of the ADA2 protein or ADA2 fusion protein, even in the absence of an observable phenotypic response.

C. Methods of Treatment

The present invention further provides methods for treating an ADA2-associated disease in a subject. The methods include administering to the subject a prophylactically effective amount or a therapeutically effective amount of a pharmaceutical composition comprising an isolated human ADA2 protein, or biologically active fragment thereof, or an ADA2 fusion protein of the invention. The pharmaceutical compositions of the present invention have numerous in vitro and in vivo therapeutic utilities involving the treatment of an ADA2-associated disease or disorder. The isolated human ADA2 proteins, or functional domains thereof, or ADA2 fusion proteins of the present invention can be administered to cells in culture, in vitro or ex vivo, or to human subjects, e.g., in vivo, to treat or prevent an ADA2-associated disease or disorder. For example, the isolated human ADA2 protein, or functional domain thereof, or ADA2 fusion protein can be used to elicit in vivo or in vitro one or more of the following biological activities: increasing differentiation of monocytes into macrophages, e.g., M2 macrophages, e.g., M2a macrophages, M2b macrophages or M2c macrophages, stimulating CD4+ T cell proliferation, and increasing endothelial cell development. Alternatively, the isolated human ADA2 protein, or functional domain thereof, or ADA2 fusion protein can be used to elicit in vivo or in vitro one or more of the following biological activities: reduction in acute-phase reactants, reduction in gastrointestinal manifestations (e.g., abdominal pain), reduction in neurological manifestations (e.g., pain or numbness), reduction in stroke occurrence, amelioration of fever and rash, reduction in neutrophil and macrophage infiltration in skin biopsies, and/or amelioration of hypertension in cases with renal hypertension. In a preferred embodiment, the isolated human ADA2 protein, or functional domain thereof, or ADA2 fusion protein can be used to elicit in vivo or in vitro a reduction in two or more, three or more, four or more, or five or more of the biological activities listed herein.

As used herein "an ADA2-associated disease" is a disease or condition which is mediated by ADA2 activity or is associated with aberrant ADA2 expression or activation. Specific examples of ADA2-associated diseases include, but are not limited to, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM. In a preferred embodiment, the ADA2-associated disease or disorder is polyarteritis nodosa.

As used herein, the term "subject" is intended to include human and non-human animals. Non-human animals include all vertebrates, e.g., mammals and non-mammals, such as non-human primates, sheep, dogs, cats, cows, horses, rabbits, chickens, amphibians, and reptiles. A preferred subject is a human subject having an ADA2-associated disease or disorder.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the ADA2 proteins or ADA2 fusion proteins of the present invention according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, an ADA2-associated disease or disorder by administering to the subject an ADA2 protein, biologically active fragment, or an ADA2 fusion protein of the invention. Subjects at risk for a disease which is caused or contributed to by aberrant ADA2 expression or activity can be identified by, for example, any or a combination of diagnostic or prognostic assays as described herein. Administration of a prophylactic agent can occur prior to the manifestation of symptoms characteristic of the ADA2 aberrancy, such that a disease or disorder is prevented or, alternatively, delayed in its progression.

The pharmaceutical compositions of the invention may contain a prophylactically effective amount of the isolated ADA2 protein, ADA2 functional domain, or ADA2 fusion protein. As used herein, the term "prophylactically effective amount" refers to the amount of protein effective to prevent development of an ADA2-associated disease or disorder in a subject. Those of skill in the art could determine the appropriate prophylactically effective amount from the data presented here in the Examples section. The exact dosage may depend on the particular active agent used.

2. Therapeutic Methods

Another aspect of the invention pertains to methods of modulating ADA2 activity in a subject having an ADA2-associated disease or disorder for therapeutic purposes.

Accordingly, in an exemplary embodiment, the method of the invention involves contacting a cell with an ADA2 protein or an ADA2 fusion protein of the invention. These methods can be performed in vitro (e.g., by culturing the cell with the ADA2 protein or the ADA2 fusion protein) or, alternatively, in vivo (e.g., by administering the ADA2 protein or the ADA2 fusion protein to a subject). As such, the present invention provides methods of treating an individual afflicted with an ADA2-associated disease or disorder, characterized by aberrant expression or activity of an ADA2 protein or nucleic acid molecule. Examples of such disorders include polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM. In a preferred embodiment of the invention, the ADA2-associated disease or disorder is polyarthritis nodosa (PAN). In another embodiment of the invention, the ADA2-associated disease or disorder is microscopic polyangitis, Wegener's granulamatosis, Churg-Strauss syndrome, Takayasu arteritis, Giant cell arteritis, Livedoid vasculopathy or small vessel vasculitis.

The term "treating" includes the application or administration of the ADA2 proteins, fragments and fusion proteins of the invention to a subject, or application or administration of ADA2 proteins, fragments and fusion proteins of the invention to a subject who has an ADA2-associated disease or disorder, with the purpose of curing, healing, alleviating, relieving, altering, remedying, ameliorating, preventing, improving, or affecting the ADA2-associated disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; or improving a subject's physical or mental well-being. Treatment may be therapeutic or prophylactic. The treatment or amelioration of symptoms can be based on objective or subjective parameters; including the results of a physical examination.

The pharmaceutical compositions of the invention may contain a therapeutically effective amount of the isolated ADA2 protein, ADA2 functional domain, or ADA2 fusion protein. As used herein, the term "therapeutically effective amount" refers to the amount of protein effective to treat an ADA2-associated disease or disorder in a subject. Those of skill in the art could determine the appropriate therapeutically effective amount from the data presented here in the Examples section. The exact dosage may depend on the particular active agent used.

Suitable routes of administering the isolated human ADA2 proteins, fragments, and fusion proteins of the invention in vivo and in vitro are well known in the art and can be selected by those of ordinary skill. For example, the isolated human ADA2 proteins, fragments, and fusion proteins can be administered by injection (e.g., intravenous or subcutaneous). Suitable dosages of the proteins used will depend on the age and weight of the subject and the concentration and/or formulation of the pharmaceutical composition.

A preferred embodiment of the present invention involves a method for treatment of an ADA2-associated disease or disorder which includes the step of administering a therapeutically effective amount of an ADA2 protein or an ADA2 fusion protein of the invention to a subject. As defined herein, a therapeutically effective amount of protein (i.e., an effective dosage) ranges from about 0.001 to 30 mg/kg body weight. The skilled artisan will appreciate that certain factors may influence the dosage required to effectively treat a subject, including but not limited to the severity of the ADA2-associated disease or disorder, previous treatments, the general health and/or age of the subject, and other diseases present. Moreover, treatment of a subject with a therapeutically effective amount of protein can include a single treatment or, preferably, can include a series of treatments. In a preferred example, a subject is treated with an ADA2 protein or ADA2 fusion protein of the invention one time per week for between about 1 to 10 weeks. It will also be appreciated that the effective dosage of protein used for treatment may increase or decrease over the course of a particular treatment. Changes in dosage may result from the results of diagnostic assays as described herein.

Stimulation of ADA2 activity is desirable in situations in which ADA2 is abnormally downregulated and/or in which increased ADA2 activity is likely to have a beneficial effect. In one embodiment, the method involves administering the ADA2 protein or ADA2 fusion protein of the invention alone, or in combination with other agent(s) which modulate (e.g., upregulate or downregulate) ADA2 expression or activity. In one embodiment, the method involves administering an ADA2 protein or an ADA2 fusion protein of the invention as therapy to compensate for reduced or aberrant ADA2 expression or activity in the subject having an ADA2-associated disease or disorder.

The isolated human ADA2 proteins, fragments, and fusion proteins of the invention can also be co-administered with one or other more therapeutic agents. In one embodiment, the isolated human ADA2 proteins, fragments, and fusion proteins can be administered before, after or concurrently with the agent or can be co-administered with other known therapies. Co-administration of the isolated human ADA2 proteins, fragments, and fusion proteins of the present invention with other therapeutic agents may provide two agents which operate via different mechanisms which yield an increased therapeutic effect. Such co-administration can solve problems due to development of resistance to drugs.

3. Pharmacogenomics

The ADA2 proteins and ADA2 fusion proteins of the present invention can be administered to individuals to treat (prophylactically or therapeutically) ADA2-associated disorders associated with aberrant ADA2 activity (e.g, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, and low serum IgM). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an ADA2 protein or ADA2 fusion protein as well as tailoring the dosage and/or therapeutic regimen of treatment with the ADA2 protein or ADA2 fusion protein.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11):983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an ADA2 protein or an ADA2 fusion protein of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual having an ADA2-associated disease or disorder. This knowledge, when applied to dosing or drug selection, can avoid adverse reactions or therapeutic failure and thus enhance therapeutic or prophylactic efficiency when treating a subject with an ADA2 protein or fusion protein of the invention.

Values and ranges included and/or intermediate within the ranges set forth herein are also intended to be within the scope of the present disclosure. Ranges having values recited herein as an upper or lower limit are also intended to be within the scope of the present disclosure.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Two types of adenosine deaminases exist in humans: ADA1 and ADA2. The primary role of ADA1, which acts as a monomer, is to eliminate intracellular toxic derivatives of adenosine and deoxyadenosine and to protect the cells from apoptosis (see, e.g., Franco et al., 2007, Crit. Rev. Immunol, 27:495-509 and Niisu et al., 1998, Blood, 92:3368-3375). The absence of ADA1 due to genetic mutations results in severe combined immunodeficiency (SCID), which is associated with apoptotic death of lymphocytes triggered by accumulation of adenosine and its derivatives (see, e.g., Hershfield, 2005, Eur. J. Immunol., 35:25-30).

ADA2 (Adenosine Deaminase 2), also known as Cat Eye Syndrome Chromosome Region, Candidate 1, or CECR1, is an adenosine deaminase that catalyzes the deamination of adenosine and 2-prime-deoxyadenosine to inosine and deoxyinosine, respectively. In contrast to ADA1, ADA2 is a secreted homodimer and is highly expressed in plasma, and dimerization is required for full enzymatic activity and secretion. ADA2 is highly expressed in dendritic cells, CD14+ monocytes, and lymphoid tissues, particularly in the thymus. In addition to having catalytic activity, ADA2 also plays a role as a growth factor for endothelial and leukocyte development and differentiation. ADA2 binds to different types of cells via heparin sulfate and chondroitin sulfate containing proteoglycans.

The activity of both ADA1 and ADA2 can be inhibited by 2-deoxycoformcin (pentostatin), but (+)erythro-9-(2-hydroxy-3-nonyl)adenine (EHNA) can be used to selectively inhibit ADA1.

Recently, several groups have discovered that recessive loss-of-function mutations in CECR1, the gene encoding ADA2, can cause early-onset stroke and polyarteritis nodosa vasculopathy with highly varied clinical expression (Elkan et al., 2014, N. Engl. J. Med., 370(10):921-931 and Zhou et al., 2014, N. Engl. J. Med., 370(10):911-920). These loss-of-function mutations in humans reflect both impairment of the catalytic activity of ADA2 and the loss of its growth factor activities (see, Elkan et al., 2014).

Polyarteritis nodosa (PAN) is a rare disease that was first described in 1866 as a systemic vasculitis that affects medium and small muscular arteries, resulting in secondary tissue ischemia affecting multiple organs. PAN has a varied age of onset, severity and organ involvement, with manifestations ranging from severe or fatal systemic vasculitis or multiple strokes in children to limited cutaneous manifestation in adults. Traditionally, PAN is diagnosed in middle age or later, but it often occurs in children, as well. The estimated incidence of PAN is 1-4.5 cases per 100,000 population annually. The course of PAN disease is highly variable in individual patients. Some may have rapidly progressive disease, leading to death in days or weeks, with mortality associated with kidney failure, cardiac complications, or GI complications.

Current therapeutic options for ADA2-associated diseases and disorders are lacking and are limited to management of the symptoms of the disease. Specifically, treatment of PAN is typically palliative and usually consists of the use of corticosteroid drugs to relieve inflammation. Cyclophosphamides are used as an add-on therapy. To date, gene therapy has not been considered due to the short half-life of recombinant ADA2 proteins.

Figure 5:
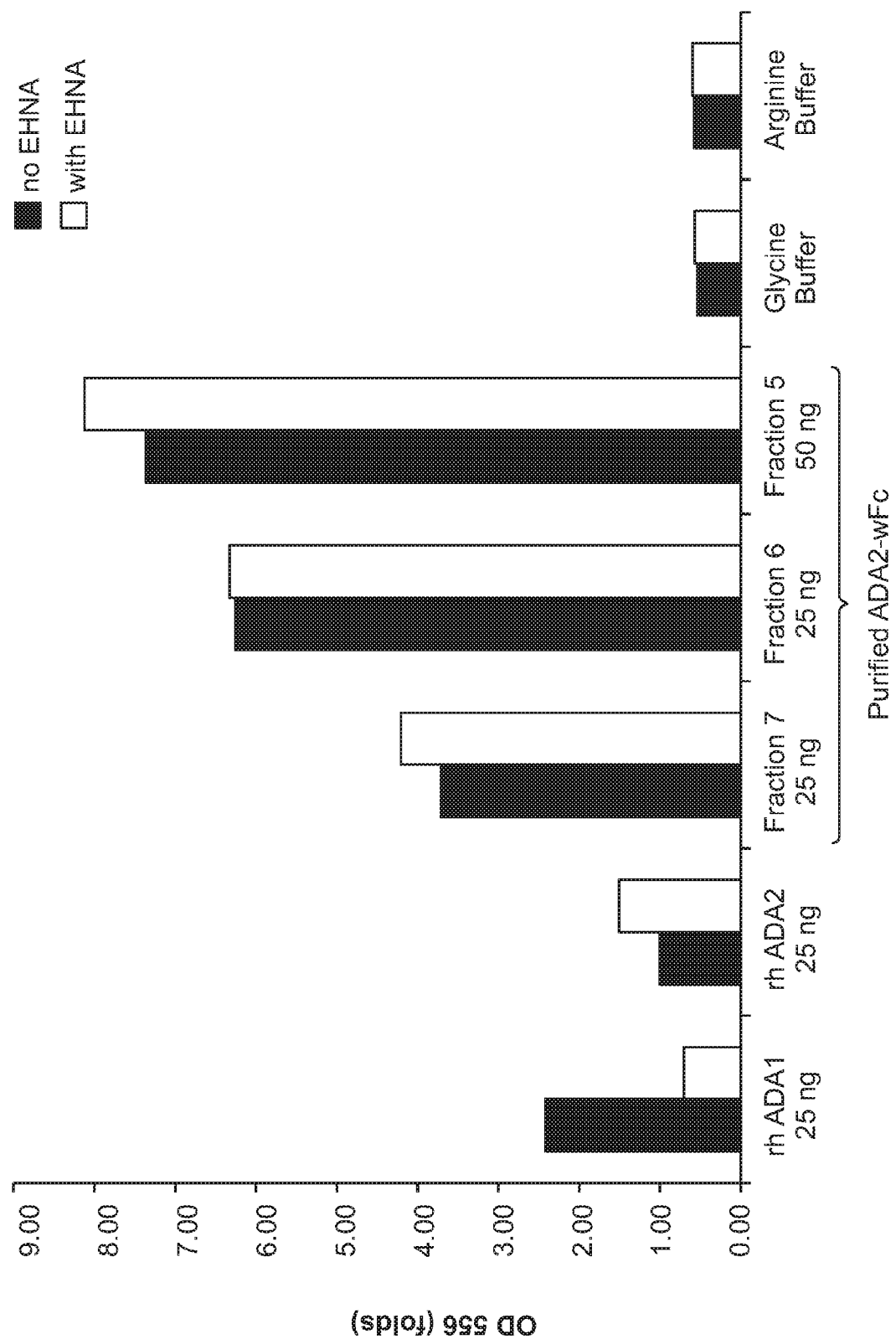
FIG. 5 depicts that the purified ADA2-Fc fusion proteins from the conditioned medium of HEK293-6E cells have high specific activities. Glycine Buffer comprises 62.5 mM Glycine and 375 mM Tris at pH 8.0. Arginine Buffer comprises 0.1 M glycine, 0.5 M arginine, 0.1 M betaine, and 60 mM Tris-HCl at pH 8.0. rhADA1 refers to Recombinant Human Adenosine Deaminase/ADA purchased from R&D Systems (Cat #7048-AD-010, Lot # DATP0614051). rhADA2 refers to Recombinant Human Adenosine Deaminase 2/CECR1 purchased from R&D Systems (Cat #7518-AD-010, Lot # DASB0414071). ADA2-wFc refers to ADA2 with a C-terminal wild-type Fc domain. Bars on the left of each grouping represent fractions not treated with EHNA. Bars on the right of each grouping represent fractions treated with EHNA.
Figure 6:
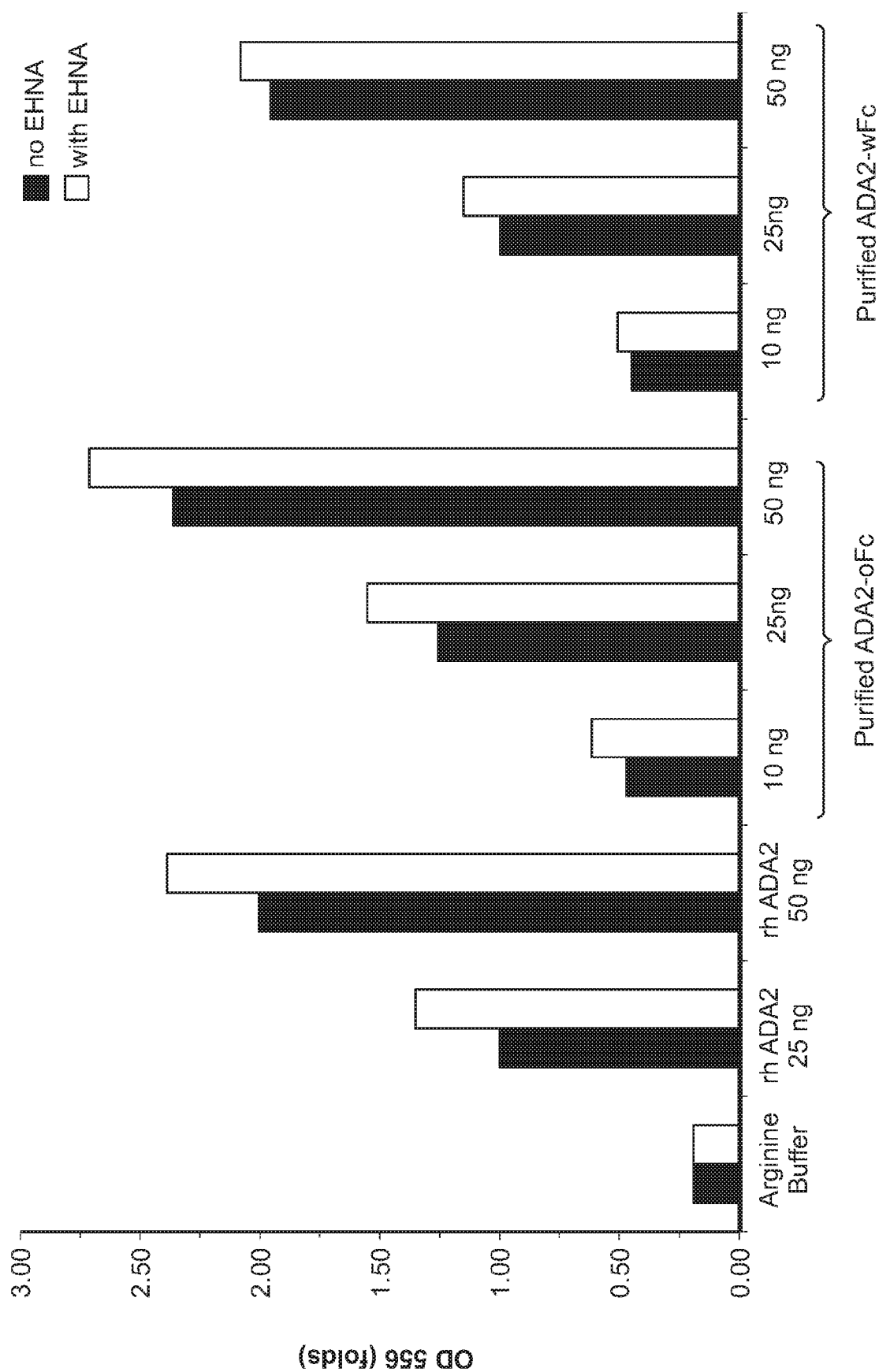
FIG. 6 depicts that the purified ADA2-Fc fusion proteins from the conditioned medium of HEK293-6E cells have high specific activities. Arginine Buffer comprises 0.1 M glycine, 0.5 M arginine, 0.1 M betaine, and 60 mM Tris-HCl at pH 8.0. rhADA2 refers to Recombinant Human Adenosine Deaminase 2/CECR1 purchased from R&D Systems (Cat #7518-AD-010, Lot # DASB0414071). ADA2-oFc refers to ADA2 with a C-terminal Orencia Fc domain. ADA2-wFc refers to ADA2 with a C-terminal wild-type Fc domain. Bars on the left of each grouping represent fractions not treated with EHNA. Bars on the right of each grouping represent fractions treated with EHNA.

The present invention is directed to isolated recombinant human ADA2 proteins or ADA2 fusion proteins (see FIGS. 5 and 6). ADA2 fusion proteins were generated in order to increase the half-life of the ADA2 protein, thereby increasing the effectiveness of the therapeutic effects of the compositions of the invention. The proteins of the invention can be surprisingly used to restore ADA2 activity in subjects having loss-of-function mutations in ADA2 and can increase differentiation of monocytes into macrophages, e.g., M2 macrophages, e.g., M2a macrophages, M2b macrophages or M2c macrophages, stimulate CD4+ T cell proliferation, and increase endothelial cell development. More specifically, the ADA2 proteins and ADA2 fusion proteins of the invention can be used to treat subjects having ADA2-associated diseases or disorders, including but not limited to, polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, low serum IgM, microscopic polyangitis, Wegener's granulamatosis, Churg-Strauss syndrome, Takayasu arteritis, giant cell arteritis, Livedoid vasculopathy and small vessel vasculitis.

Example 1: Generation of ADA2 Proteins and Fusion Proteins

Figure 2:
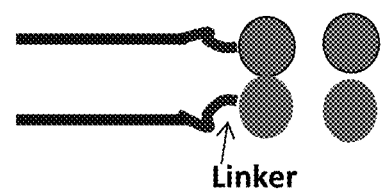
FIG. 2 depicts linkers that can be implemented in linking the ADA2 proteins to another peptide to create, for example, ADA2 fusion proteins which, for example, increase the half-life of the resultant ADA2 fusion protein. The protein that increases the half-life of the ADA2 protein or the ADA2 fusion protein can be a CTP molecule, two CTP molecules attached in tandem, or an Fc domain of an Ig.
Figure 2:
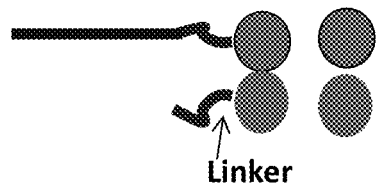

The effect of ADA2-Fc proteins from the conditioned medium of HEK293-6E cells was studied. Specifically, recombinant human ADA1 purchased from R&D systems and recombinant human ADA2 purchased from R&D systems were used as controls. Due to the short half-life of ADA2 protein and biologically active fragments, an ADA2-Fc fusion (a wild-type Fc domain fused to the C-terminus of human ADA2) and an ADA2-oFc fusion (an Orencia Fc domain fused to the C-terminus of human ADA2) were generated (FIGS. 1 and 2).

Figure 3:
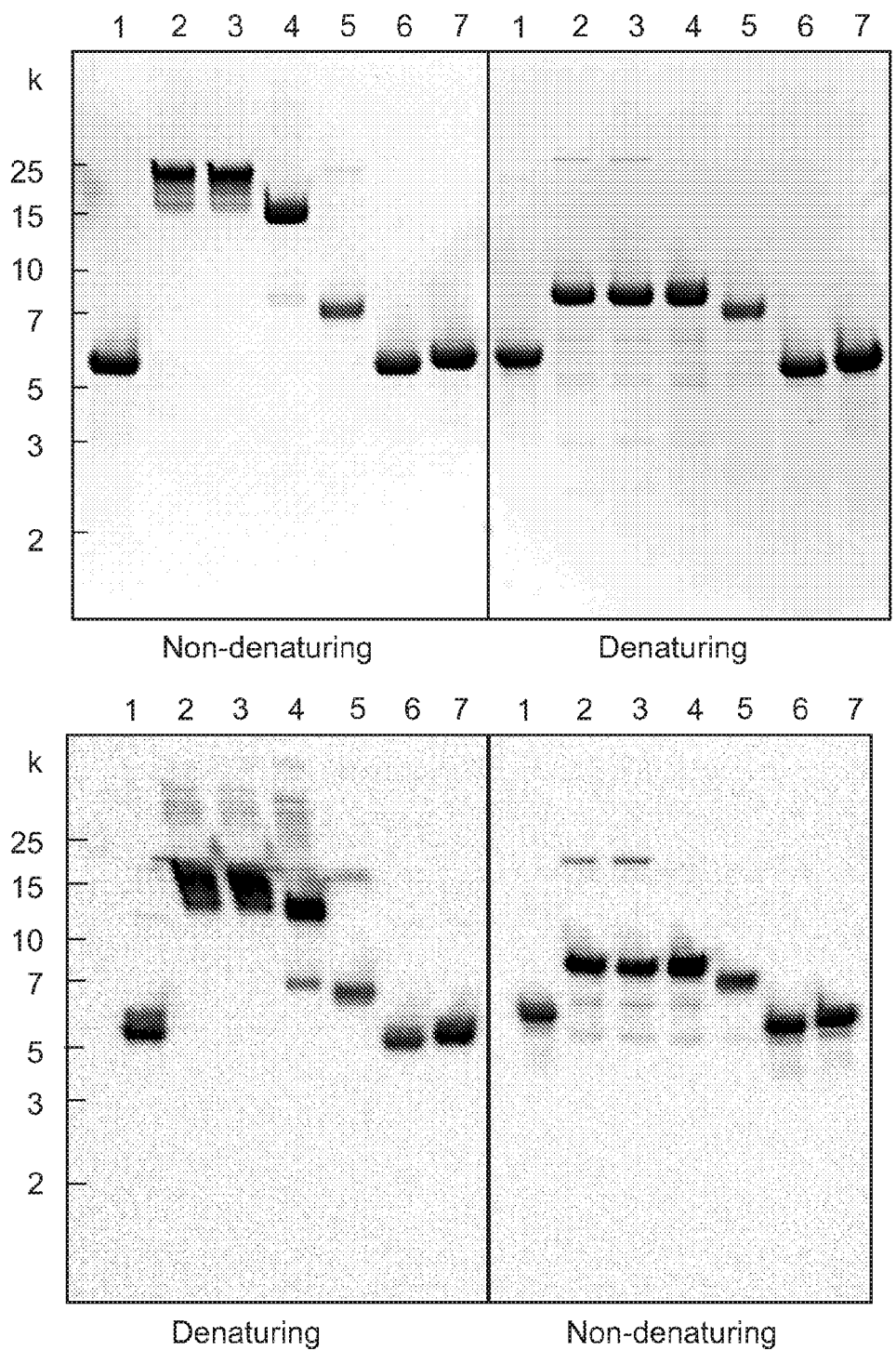
FIG. 3 depicts SDS-PAGE and Western blotting of ADA2 proteins and fusion proteins.

ADA2 proteins and fusions were resolved on 4-12% SDS-polyacrylamide gel at 100V in Tris-glycine SDS running buffer. The proteins were either stained with GelCode Blue Stain Reagent (Thermo Fisher Scientific) or transferred onto PVDF membranes using iBlot 2. The blot was blocked with 5% non-fat milk at room temperature for 30 minutes and incubated with an α-CECR1 rabbit polyclonal antibody (Thermo Fisher Scientific, Cat # PA5-30635) overnight at 4° C. After washing 4 times with PBST (1×PBS/0.05% Tween-20), 5 minutes each, the blot was incubated with an HRP-conjugated goat α-rabbit polyclonal secondary antibody at room temperature for one hour. The blot was washed 4 times with PBST, 5 minutes each, and the signals were detected using Pierce ECL Western Blotting Substrate (Thermo Fisher Scientific, Cat #32209). As can be seen in FIG. 3, the ADA2 proteins and fusion proteins were purified.

Example 2: ADA2 Protein and Fusion Protein Adenosine Deaminase Activity In Vitro The protein constructs were cloned and expressed in HEK293-6E cells. The medium was isolated, ADA2 proteins were purified, and adenosine deaminase activity was determined with or without EHNA, which selectively inhibits the activity of the ADA1 control.

Figure 4:
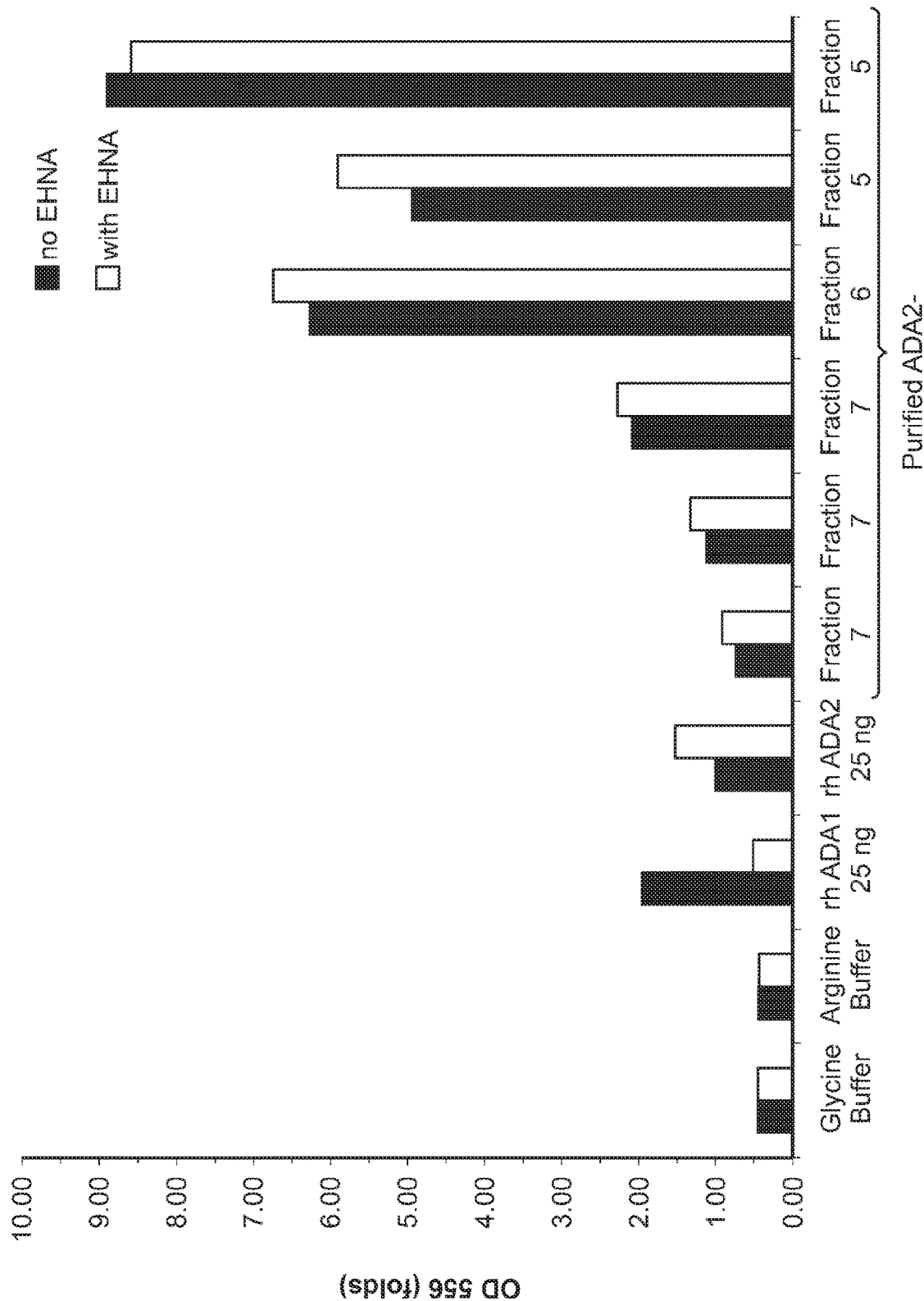
FIG. 4 depicts that purified ADA2-Fc fusion proteins from conditioned medium of HEK293-6E cells have high specific activities. Glycine Buffer comprises 62.5 mM Glycine and 375 mM Tris at pH 8.0. Arginine Buffer comprises 0.1 M glycine, 0.5 M arginine, 0.1 M betaine, and 60 mM Tris-HCl at pH 8.0. rhADA1 refers to Recombinant Human Adenosine Deaminase/ADA purchased from R&D Systems (Cat #7048-AD-010, Lot # DATP0614051). rhADA2 refers to Recombinant Human Adenosine Deaminase 2/CECR1 purchased from R&D Systems (Cat #7518-AD-010, Lot # DASB0414071). ADA2-wFc refers to ADA2 with a C-terminal wild-type Fc domain. Bars on the left of each grouping represent fractions not treated with EHNA. Bars on the right of each grouping represent fractions treated with EHNA.

As can be seen in FIGS. 4-6, purified ADA2-Fc fusion proteins have high specific activities and do not negatively affect the function of ADA2. The Fc fusion constructs, as well as an ADA2-2xCTP fusion (SEQ ID NO:23) serve to dramatically increase the half-life of the ADA2 polypeptide, thereby increasing the therapeutic effectiveness of the pharmaceutical compositions of the invention.

Figure 7:
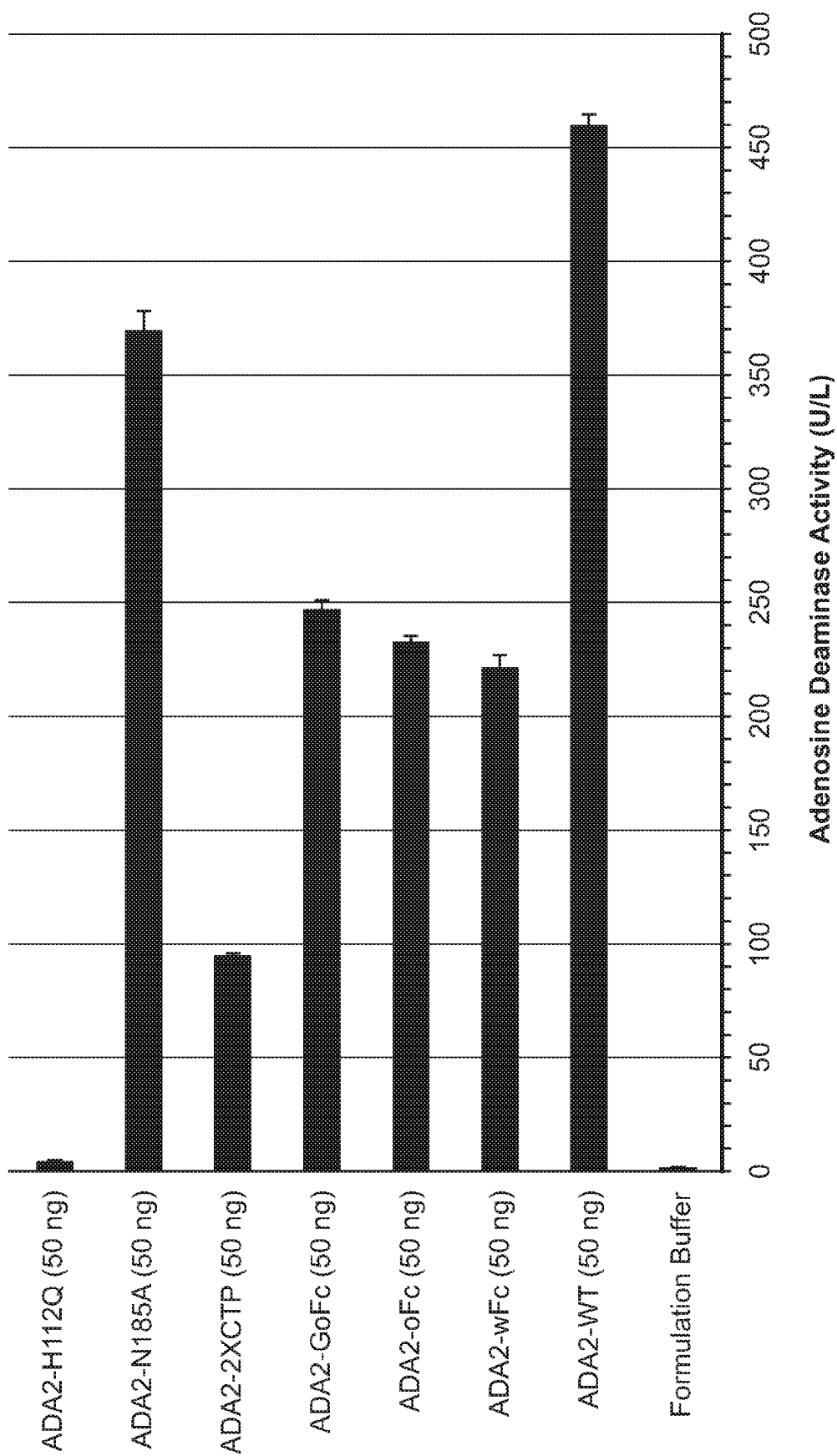
FIG. 7 depicts ADA2 enzymatic activities of the various forms of purified ADA2 proteins, ADA2-oFc (SEQ ID NO:21), ADA2-GoFc (SEQ ID NO: 25), ADA2-wFc (SEQ ID NO:27), ADA2-2xCTP (SEQ ID NO:23), ADA2 (SEQ ID NO:1), and ADA2-N185A (SEQ ID NO:7). Bars represent the amount of adenosine demaminase activity (U/L) for each protein.

In a second experiment, varying amounts of each purified ADA2 fusion protein and an ADA2-N185A mutant protein were also assayed for adenosine deaminase activity by using a commercially available ADA Assay Kit (Diazyme, cat # DZ117A-K) according to the manufacturer's instructions. As indicated by FIG. 7, 50 ng of each ADA2 protein was used, except that 15 ng of ADA2-2xCTP was used in the assay. The levels of ADA2 were determined by using a standard curve derived from an ADA calibrator supplied by the manufacturer of the assay. FIG. 7 confirms that ADA2 fusion proteins retain significant adenosine deaminase activity.

Figure 8:
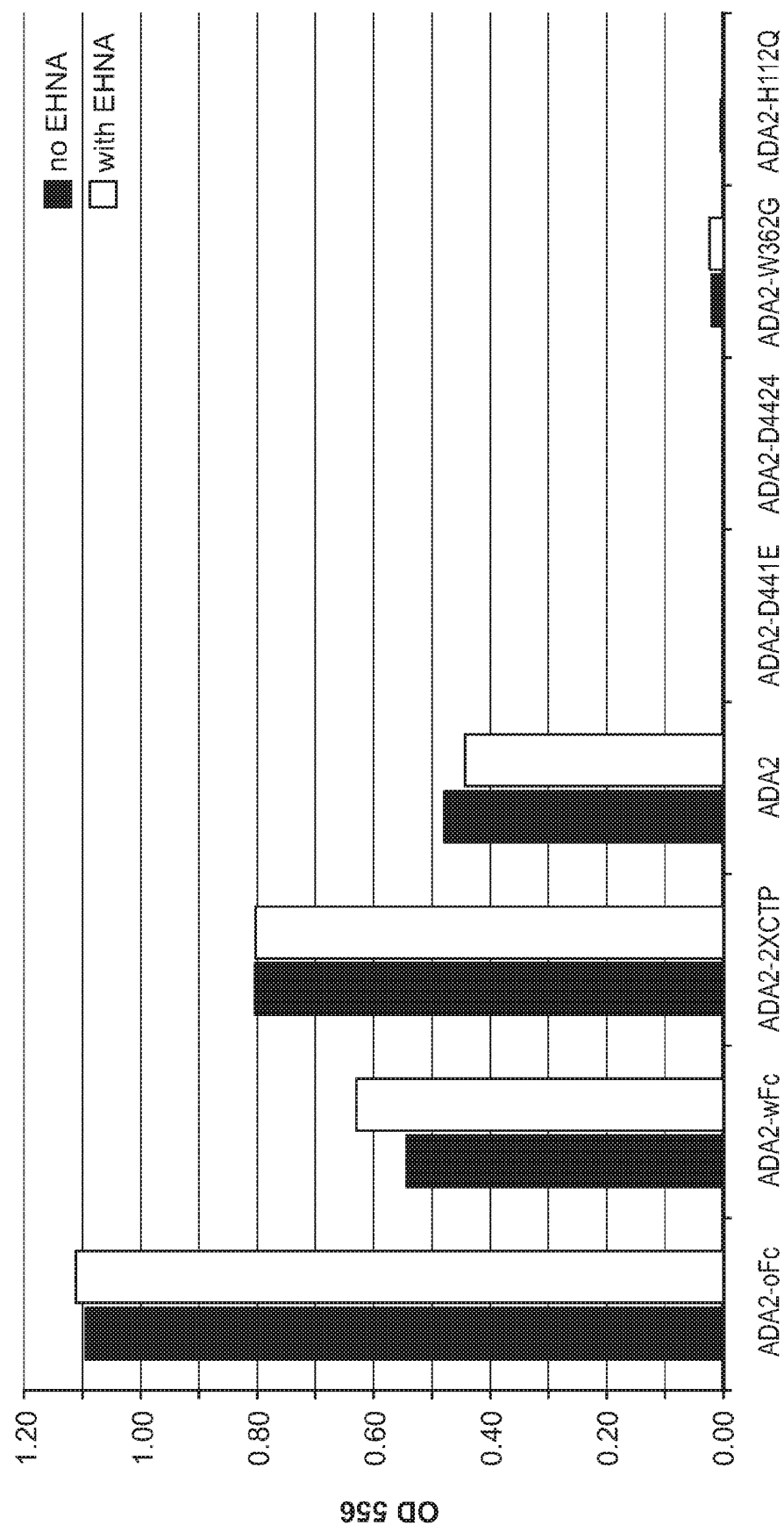
FIG. 8 depicts ADA2 enzymatic activities of the various forms of purified ADA2 proteins, ADA2-oFc (SEQ ID NO:21), ADA2-wFc (SEQ ID NO:19), ADA2-2xCTP (SEQ ID NO:23), and ADA2 (SEQ ID NO:1). Bars on the left of each grouping represent fractions not treated with EHNA. Bars on the right of each grouping represent fractions treated with EHNA.

In a second experiment, ADA2 proteins (0.4 pmole) were assayed for adenosine deaminase activities by using a commercially available ADA Assay Kit (Diazyme, cat # DZ117A-K) according to the manufacturer's instruction. Higher levels of adenosine deaminase activities were indicated by higher values of OD556. As can be seen in FIG. 8, purified ADA2 fusion proteins have high specific activities and do not negatively affect the function of ADA2. However, the ADA2 fusion proteins of the invention serve to dramatically increase the half-life of the recombinant ADA2 polypeptide.

Example 3: Pharmacokinetics Studies of ADA2 and ADA2 Fusion Proteins

Figure 9A:
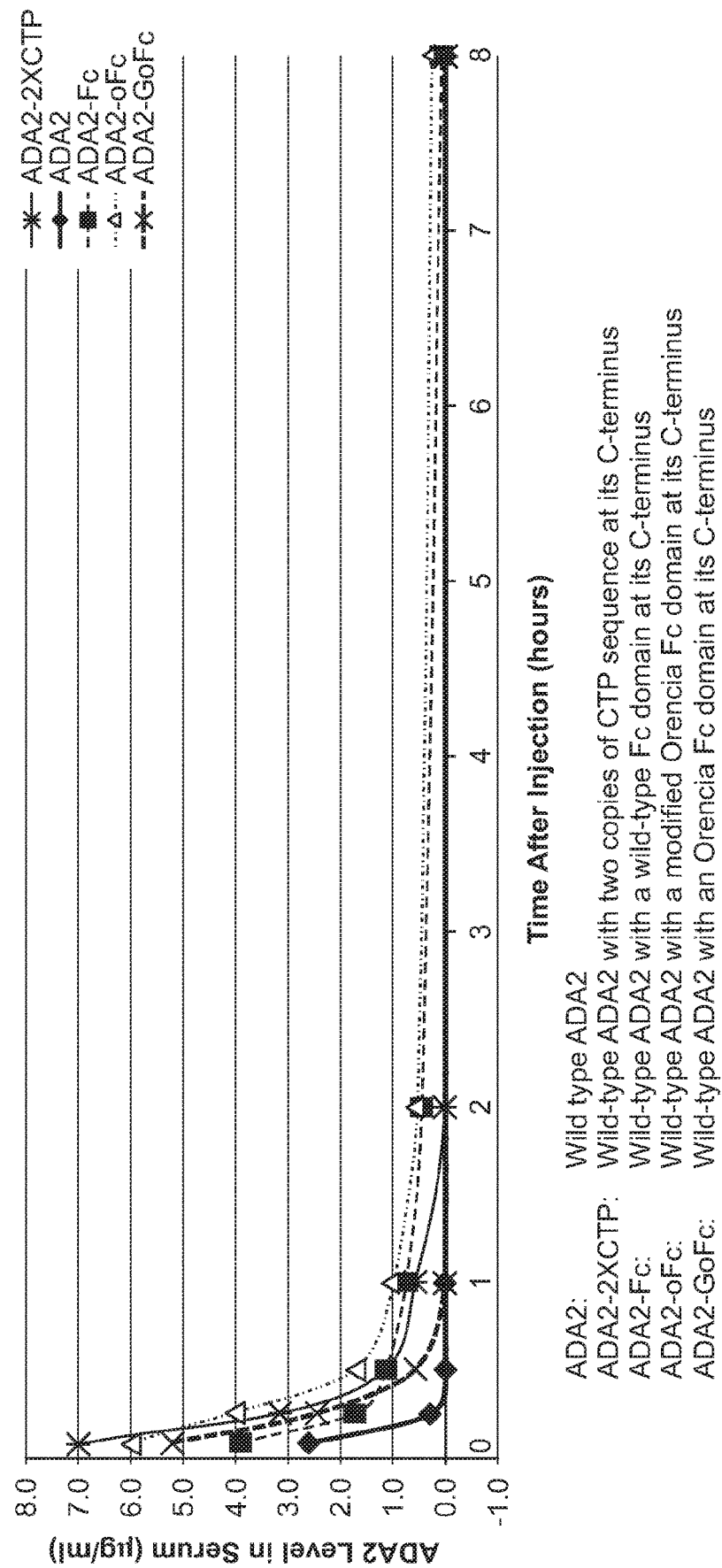

Various purified ADA2 proteins (wild-type ADA2 protein, wild-type ADA2 fusion protein containing two CTP molecules at the c-terminus, wild-type ADA2 fusion protein containing a wild-type Fc domain at the c-terminus, wild-type ADA2 fusion protein containing a modified Orencia Fc domain at the c-terminus, and wild-type ADA2 fusion protein containing an Orencia Fc domain at the c-terminus) were intravenously injected into 5-week old Sprague Dawley rats (n=3, about 150 g each). Serum samples were prepared from fresh blood at the time intervals indicated in FIGS. 9A and 9B and kept frozen until analysis. FIG. 9B depicts the same data as FIG. 9A over the course of the first 8 hours post-injection. Adenosine deaminase 2 activities were measured by using a commercially available ADA Assay Kit (Diazyme, cat # DZ117A-K) according to the manufacturer's instruction. The levels of ADA2 in serum were determined by using a standard curve derived from known quantities of a recombinant human ADA2 protein purchased from R&D Systems (cat #7518-AD-010). FIGS. 9A and 9B show that each of the ADA2 fusion proteins exhibited an increased half-life relative to wild-type ADA2. As compared to wild-type ADA2, each ADA2 fusion protein had a longer half-life in serum.

Example 4: ADA2 N-Glycosylation Mutants

Figure 10:
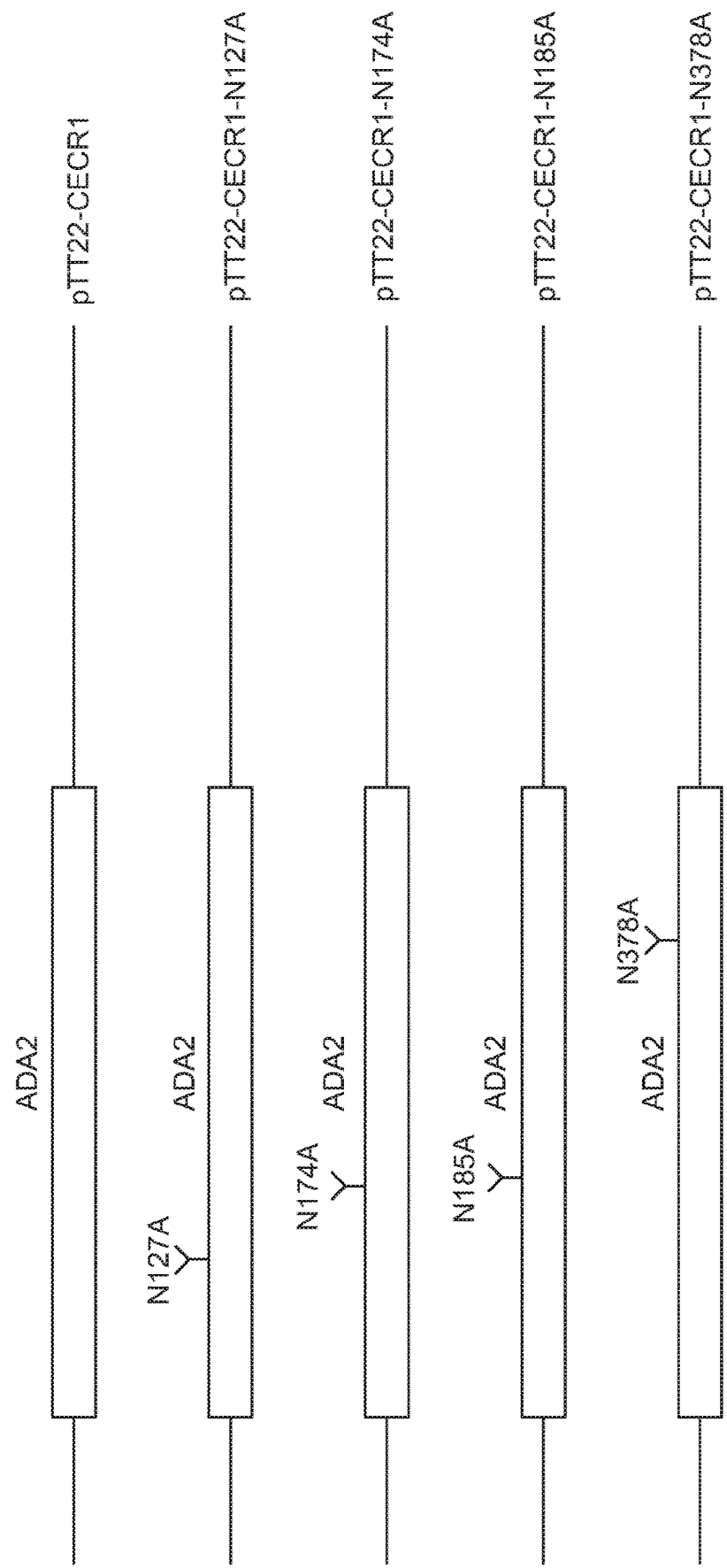
FIG. 10 depicts ADA2 mutant proteins of the invention. N to A mutations were introduced into wild-type ADA2 to remove the N-glycosylation site in order to improve its half-life in serum.

To increase the half-life of the ADA2 protein and ADA2 fusion proteins in serum, mutations were introduced into wild-type ADA2. Specifically, a number of ADA2 asparagine (N) to alanine (A) substitutions were generated to remove predicted N-glycosylation sites in the protein, including at positions 127, 174, 185 and 378 of SEQ ID NO: 1 (FIG. 10). The amino acid sequence of ADA2-N127A is set forth as SEQ ID NO: 3, ADA2-N174A is set forth as SEQ ID NO: 5, ADA2-N185A is set forth as SEQ ID NO: 7, and ADA2-N378A is set forth as SEQ ID NO: 9.

Figure 11A:
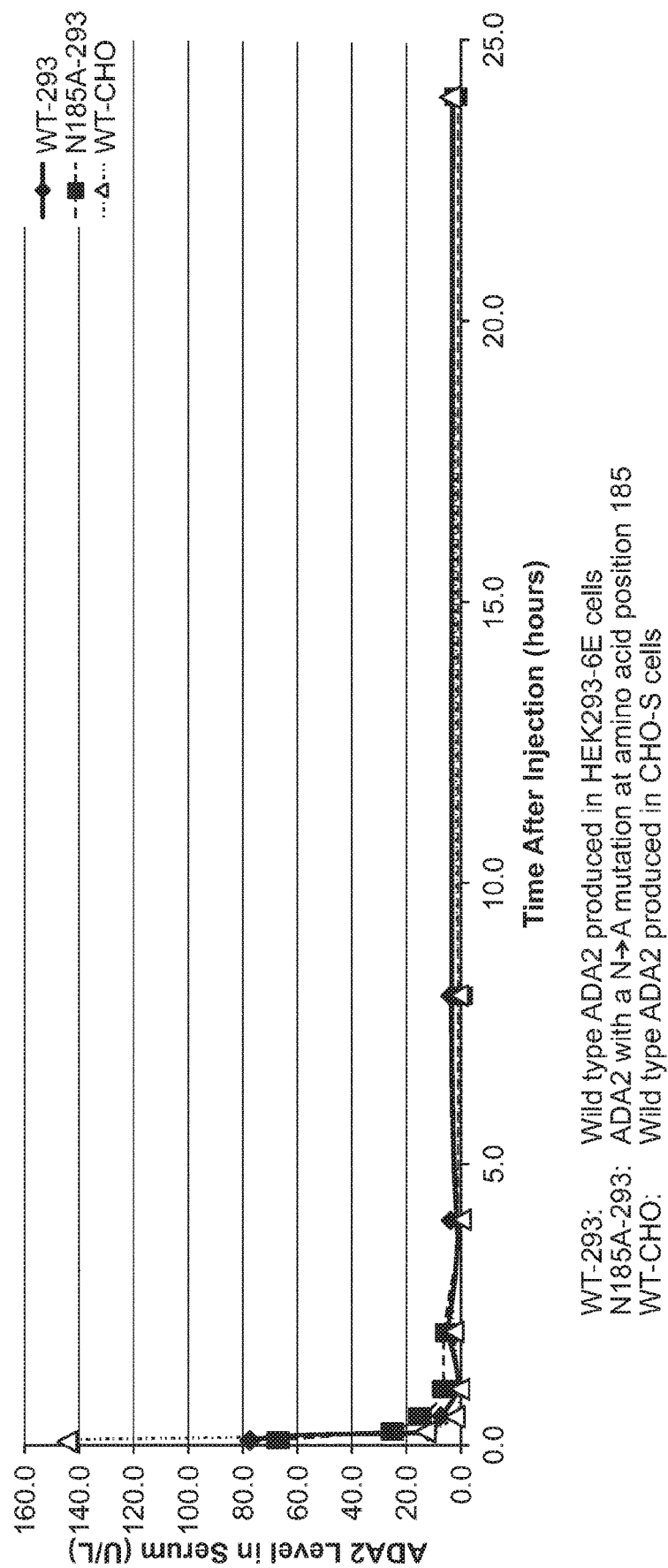
FIGS. 11A and 11B depict the results of pharmacokinetic studies of wild-type ADA2 produced in HEK293-6E cells, wild-type ADA2 produced in CHO-S cells, and an ADA2 mutant containing an N185A substitution in Sprague Dawley rats.
Figure 11B:
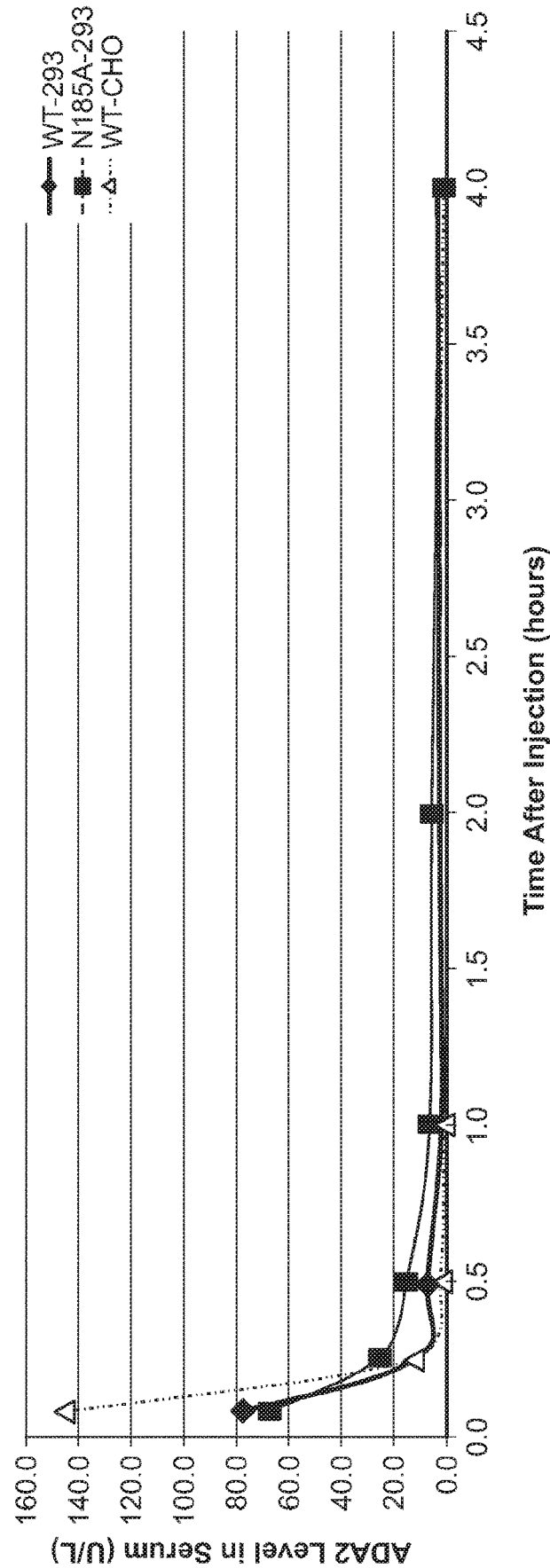

Example 5: Pharmacokinetics and Activity Studies of the ADA2-N-Glycosylation Mutants Various purified ADA2 proteins were intravenously injected into 5-week old Sprague Dawley rats (n=3, about 150 g each). Specifically, the following ADA2 proteins were injected: wild-type ADA2 produced in HEK293-6E cells, wild-type ADA2 produced in CHO-S cells, or an ADA2 mutant containing an N185A substitution. Alanine was substituted at position 185 of ADA2 to eliminate a predicted N-glycosylation site, and the mutant protein was produced in HEK292-6E cells. Serum samples were prepared from fresh blood at the time intervals indicated in FIGS. 11A and 11B and kept frozen until analysis. FIG. 11B depicts the same data as FIG. 11A over the course of the first 4 hours post-injection. Adenosine deaminase 2 activities were measured by using a commercially available ADA Assay Kit (Diazyme, cat # DZ117A-K) according to the manufacturer's instruction. The levels of ADA2 in serum were determined by using a standard curve derived from an ADA calibrator supplied by the manufacturer of the assay. FIGS. 11A and 11B show that the ADA2-N185A mutant protein exhibited an increased half-life relative to the wild-type ADA2 proteins produced in HEK293-6E and CHO-S cells at 15 minutes, 30 minutes and 1 hour post-injection. These data demonstrate that removing the N-glycosylated residue increases the half-life of the ADA2 protein, and that the mutant ADA2 protein still retains enzymatic activity.

Figure 12:
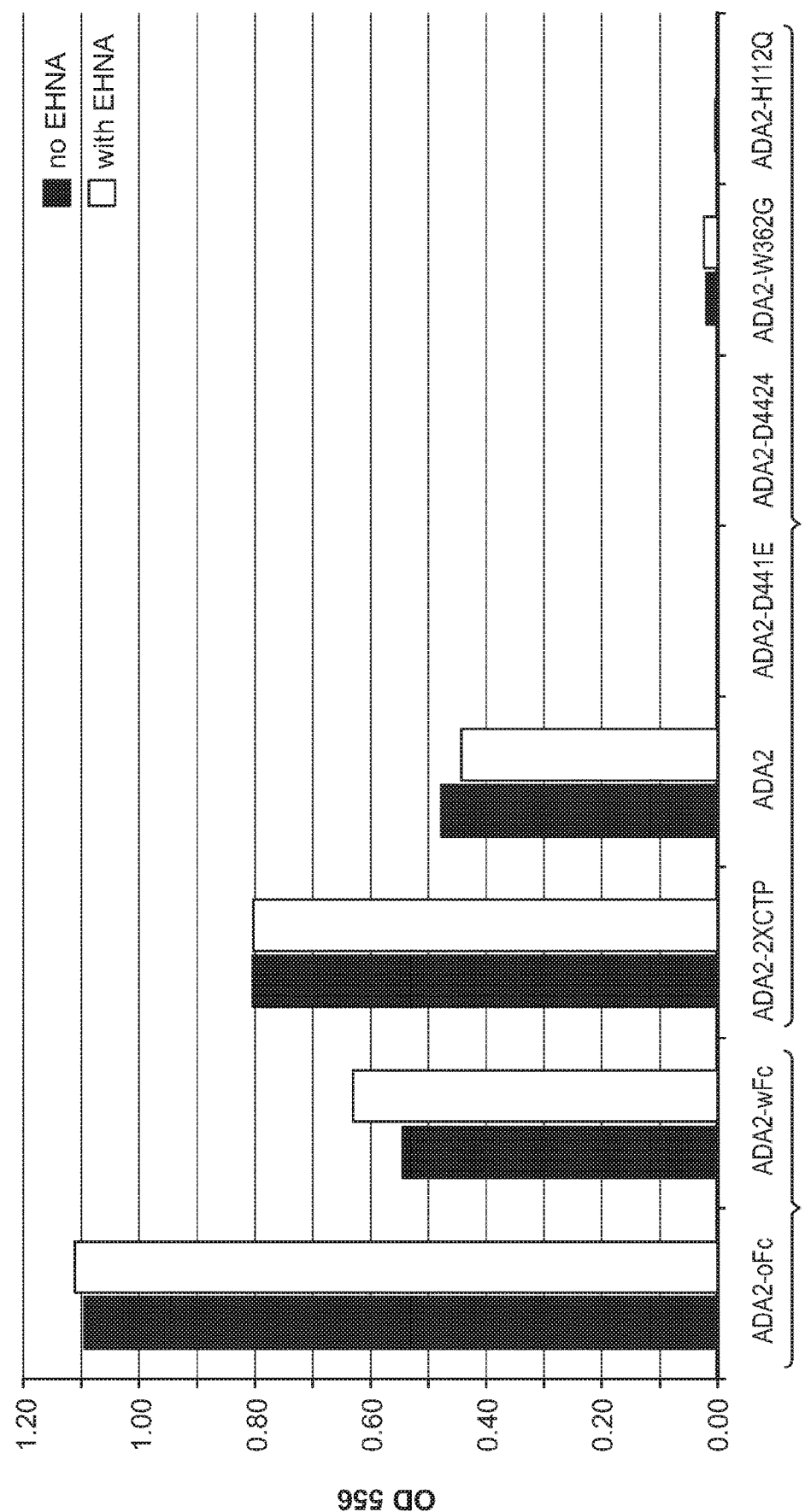
FIG. 12 depicts ADA2 enzymatic activities of the various forms of purified ADA2 proteins, ADA2-oFc (SEQ ID NO:21), ADAs-2Fc (SEQ ID NO:19), ADA2-2xCTP (SEQ ID NO:23), ADA2 (SEQ ID NO:1), ADA2-D441E (SEQ ID NO:11), ADA2-D442A (SEQ ID NO:13), ADA2-W362G (SEQ ID NO:15), and ADA2-H112Q (SEQ ID NO:17). Bars on the left of each grouping represent fractions not treated with EHNA. Bars on the right of each grouping represent fractions treated with EHNA.

As can be seen in FIG. 12, however, mutations in the catalytic domain of ADA2 (ADA2-D441E (SEQ ID NO:11) and ADA2-D442A (SEQ ID NO:13)), mutations in the dimerization domain of ADA2 (ADA2-W362G (SEQ ID NO:15)), and mutations in the zinc binding site of ADA2 (ADA2-H112Q (SEQ ID NO:17)) lead to loss of adenosine deaminase activity of the recombinant proteins.

Example 6: In Vitro Response of Human PBMCs

In order to determine whether ADA2 proteins or ADA2 fusion proteins would affect cell phonotype and differentiation, several constructs were generated. Due to the short half-life of ADA2 protein and biologically active fragments, an ADA2-Fc fusion (a wild-type Fc domain fused to the C-terminus of human ADA2) and an ADA2-oFc fusion (an Orencia Fc domain fused to the C-terminus of human ADA2) were generated. An ADA2-R&D fusion (human ADA2 with a 6×His tag) was also implemented as a control.

Figure 13:
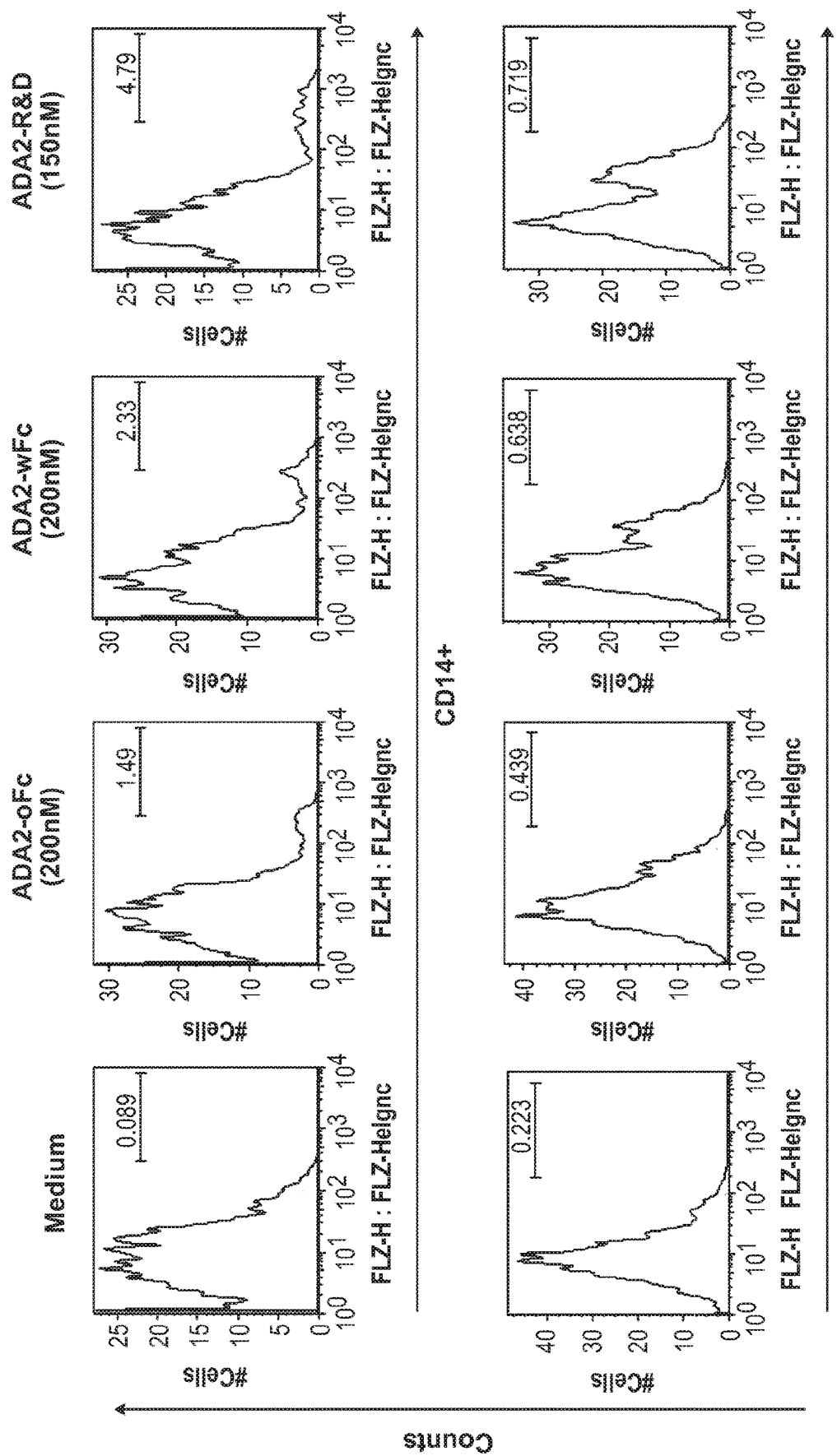
FIG. 13 depicts the count of CD14+ or CD163+ cells using flow cytometry after addition of medium alone, ADA2-oFc, ADA2-wFc or ADA2-R&D (His tagged). To briefly summarize, 9 mL of fresh blood was from St Mary's hospital on 15 Oct. 2014. $9 \times 10^6$ PBMC were obtained and about 1 million cells were cultured in a complete RPMI medium in 24-well plate ($10^6$ cell in 1 ml per well) for 44 hours in the presence or absence of various ADA2 version. Cells then were collected and stained with anti-CD14 PE and anti-CD163PE-Cy5. Flow cytometry data were acquired by FACScalibur and analyzed in FlowJo.

FIG. 13 depicts the count of CD14+ or CD163+(macrophage markers) cells using flow cytometry after addition of medium alone, ADA2-oFc, ADA2-wFc or ADA2-R&D (His tagged). To briefly summarize, 9 ml of fresh blood was from St Mary's hospital on 15 Oct. 2014. $9 \times 10^6$ PBMC were obtained and about 1 million cells were cultured in a complete RPMI medium in 24-well plate ($10^6$ cell in 1 ml per well) for 44 hours in the presence or absence of various ADA2 version. Cells then were collected and stained with anti-CD14 PE and anti-CD163PE-Cy5. Flow cytometry data were acquired by FACScalibur and analyzed in FlowJo.

FIG. 13 demonstrates that ADA2 proteins and ADA2 fusion proteins serve to dramatically shift the cell spectrum in vitro. This data is surprising, given the fact that it was previously unknown whether ADA2 had any effect on different macrophage subtypes. However, it appears that ADA2 surprisingly acts to increase differentiation of monocytes into macrophages, e.g., M2 macrophages, e.g., M2a macrophages, M2b macrophages or M2c macrophages, stimulate CD4+ T cell proliferation, and increase endothelial cell development.

Example 7: Gene Knockdown Model of Promonocytic U937 Cell Line

Figure 14:
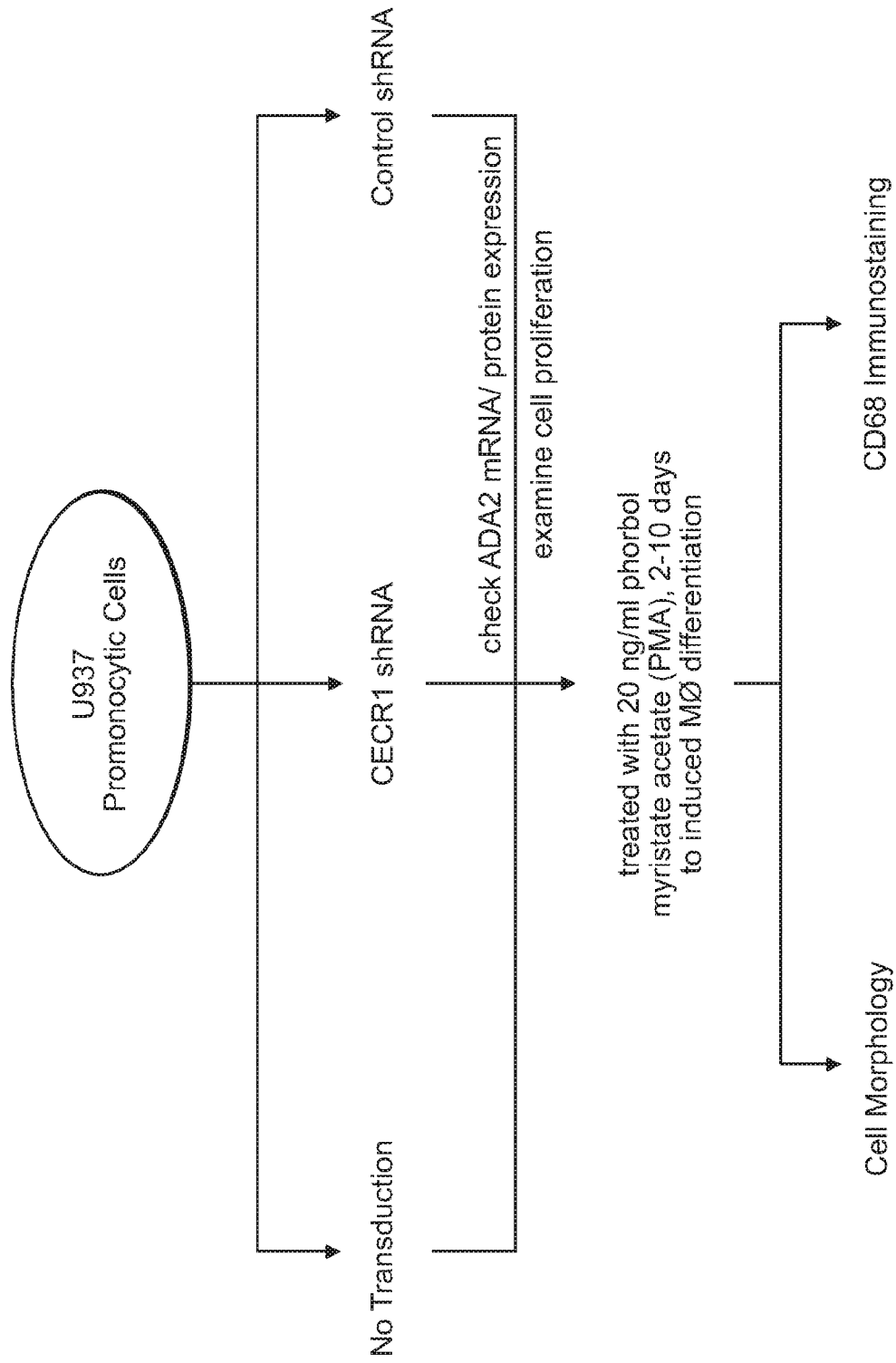
FIG. 14 depicts the study of ADA2 and Fc/CTP-ADA2 Fusions using a gene knockdown model of the Promonocytic U937 cell line.
Figure 15A:
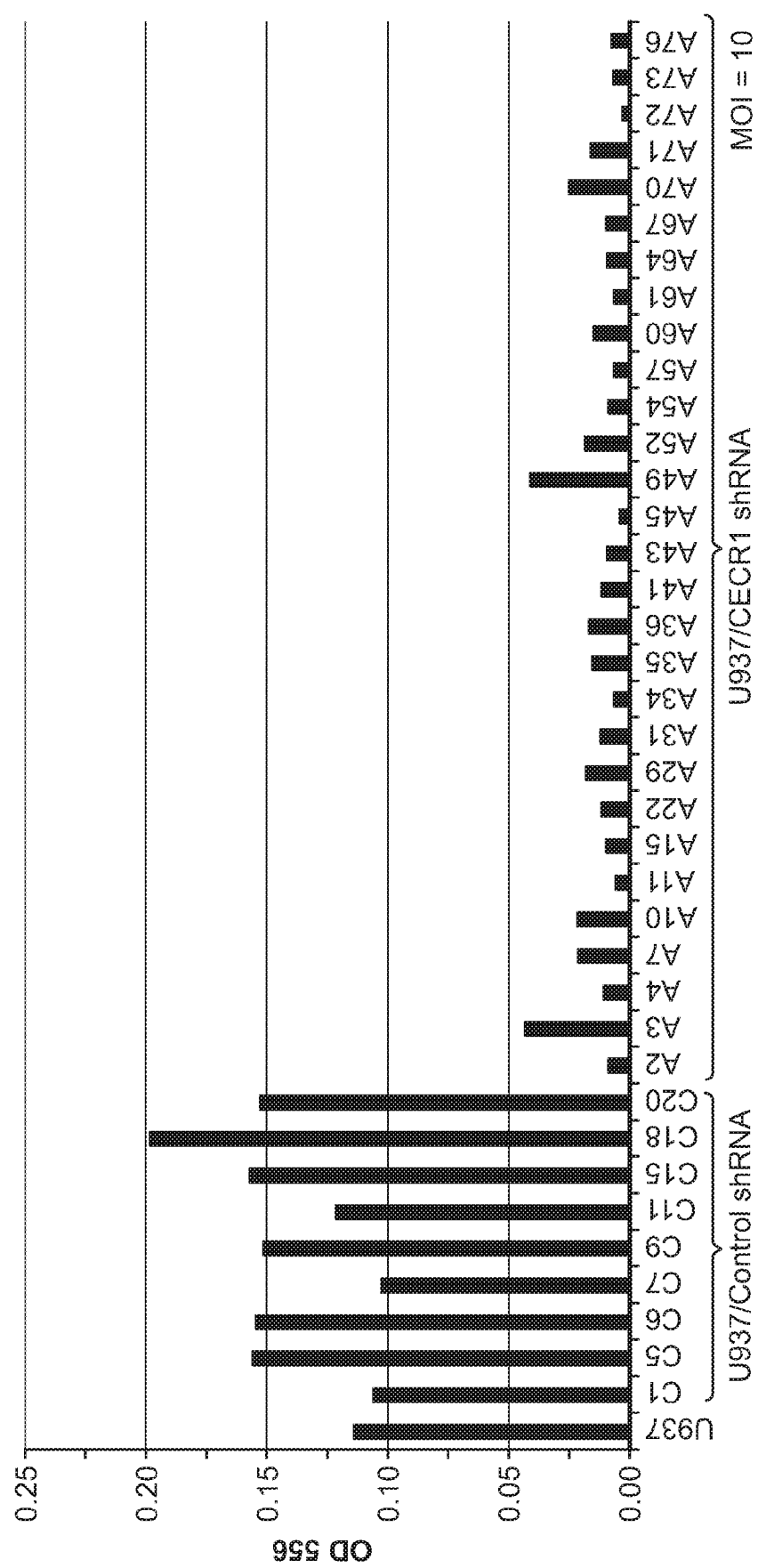
FIGS. 15A and 15B depicts ADA2 enzymatic activity in U937 cells expressing either a CECR1 shRNA or a scrambled shRNA control. A "C" demarcates that U937 clones infected with a lentiviral particle expressing a CECR1 shRNA. A, "A" demarcates those U937 clones infected with a lentiviral particle expressing a scrambled shRNA.
Figure 15B:
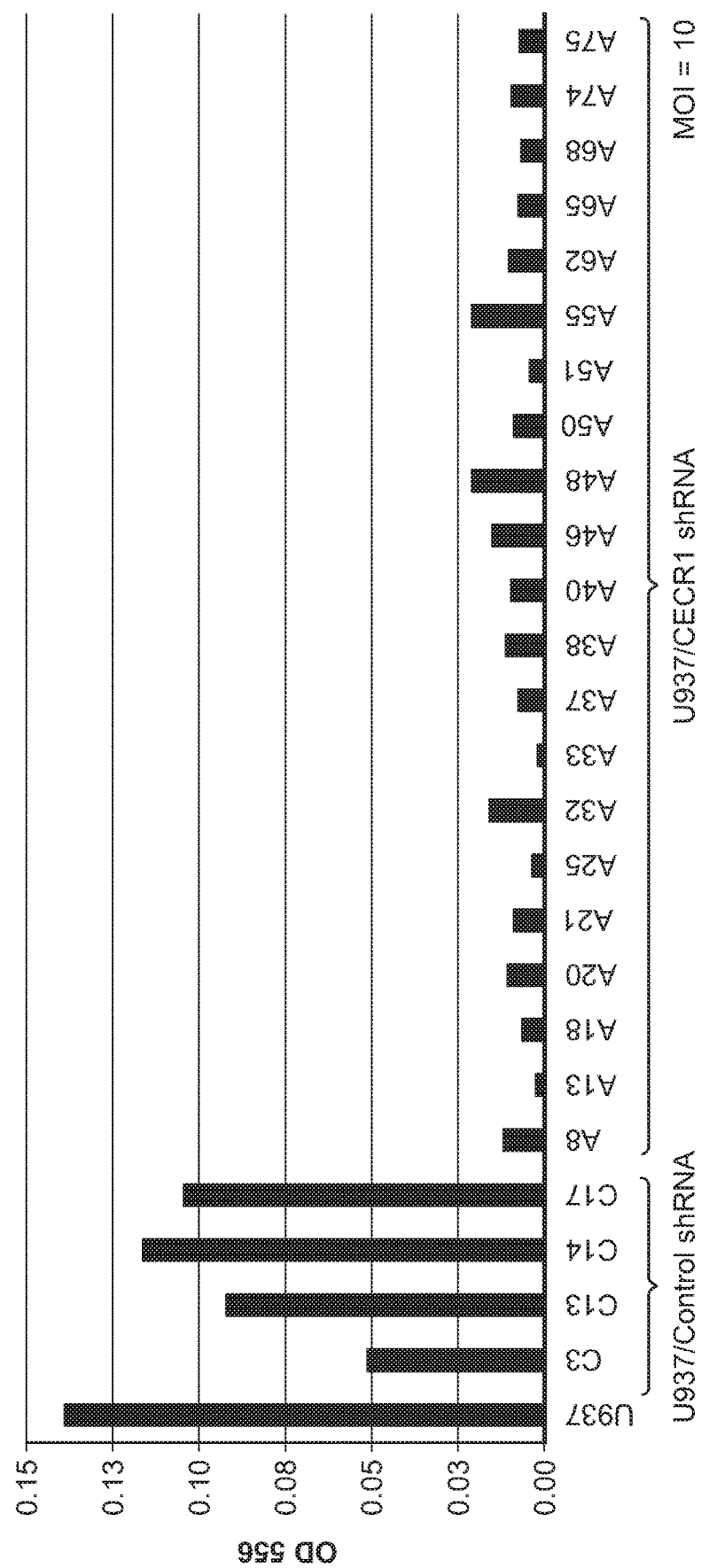

Previously, Zhou et al. (N. Engl. J. Med., 370:911-920, 2014) demonstrated that silencing of ADA2 in U937 cells significantly impairs induction of macrophage differentiation by phorbol 12-myristate 13-acetate (PMA). In order to determine ADA2 protein and ADA2 fusion protein functions in macrophage differentiation, a gene knockdown model of the Promonocytic U937 cell line was used (see, for example, FIG. 14). Briefly, stable U937 cell lines with silenced ADA2 expression were generated by lentiviral infection. The CECR1 shRNA lentiviral particles (cat # sc-72854-V) were purchased from Santa Cruz Biotechnology (designated with a C in the Figure). Control lentiviral particles (cat # sc-108080) encoding scrambled shRNA sequences that do not lead to the specific degradation of any cellular mRNA (designated as an A in the Figure) were used to generate control U937 cell lines. As depicted in FIG. 15, the silencing of ADA2 in U937 cells was confirmed by a significant reduction in ADA enzymatic activities as determined by a commercially available ADA Assay Kit (Diazyme, cat # DZ117A-K). Thus, these data demonstrate that PMA-induced macrophage differentiation can surprisingly be restored after CECR1 silencing by administering functional ADA2 or ADA2 protein fusions. U937/Control shRNA cell lines with high ADA2 expression and U937/CECR1 shRNA cell lines with minimal ADA2 expression were selected for subsequent experiments.

Example 8: In Vitro Response of U937 Cells

Figure 16:
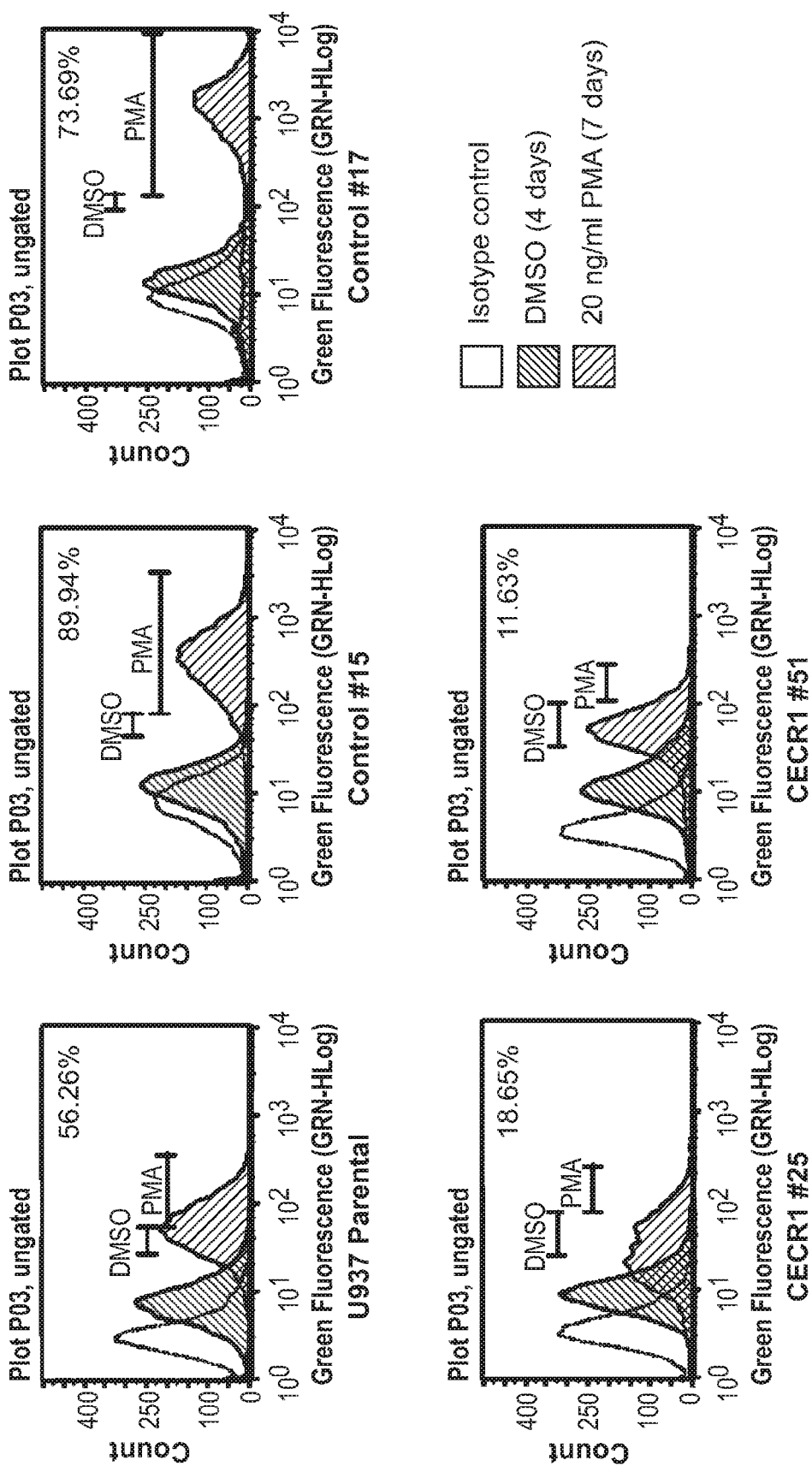
FIG. 16 depicts the results of a flow cytometric analysis of CD68 after silencing of ADA2 expression in PMA-treated U937 cells treated with CECR1 shRNA.
Figure 17:
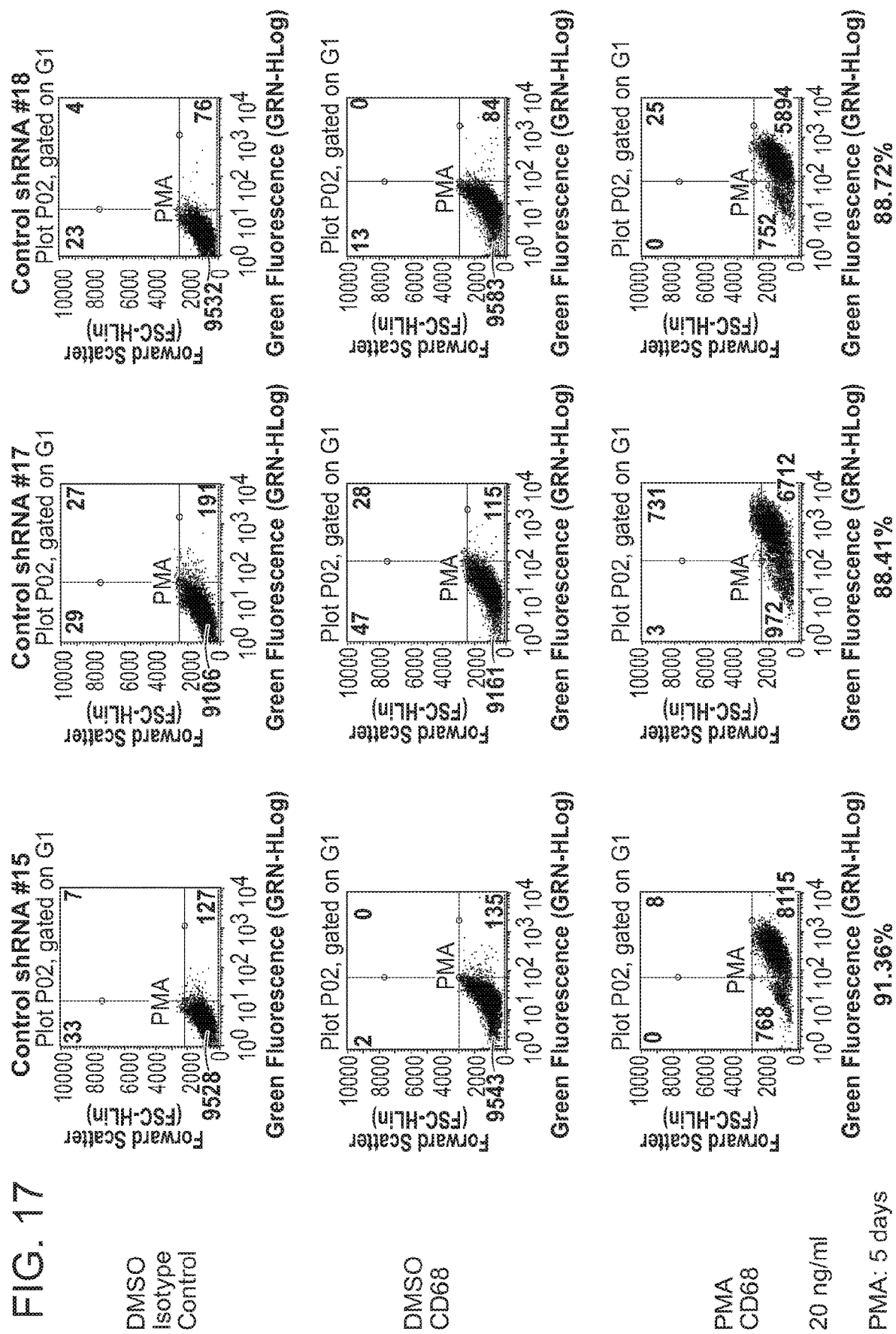
FIG. 17 depicts the results of a flow cytometric analysis of CD68 after silencing of ADA2 expression in PMA-treated U937 cells treated with CECR1 shRNA.

To determine CD68 expression as a marker for macrophage differentiation of the monocytic U937 cell line, U937 cells with or without silenced ADA2 expression were treated with DMSO (vehicle) or 20 ng/ml of PMA for 3 to 7 days. The cells were harvested, stained for CD68 expression, and analyzed by flow cytometry. FIG. 16 demonstrates that the percentage of CD68-expressing U937 cells was significantly reduced with ADA2 silencing. Therefore, these data indicate that ADA2 plays a role in the differentiation of monocytes to macrophages, and that an ADA2-deficient cell will not differentiate into a macrophage but, rather, will remain a monocyte. FIG. 17 demonstrates that almost all of the U937 cells infected with the control shRNA differentiated into macrophages after incubation with 20 ng/ml of PMA for 5 days, as indicated by the expression of CD68. Similarly, FIG. 18 demonstrates that the percentage of CD68-expressing U937 cells was significantly reduced with ADA2 silencing, indicating that ADA2 is critical for differentiation of monocytes into macrophages.

Example 9: In Vitro Macrophage Differentiation

To further determine the functions of the ADA2 proteins and fusion proteins in macrophage differentiation, cells were assayed for expression of CD68, a pan marker for M1 and M2 macrophages, and CD163, a marker for M2 macrophages.

U937 cells expressing control or CECR1 shRNA were seeded into 60 mm culture dishes and treated with DMSO or 20 ng/ml of phorbol 12-myristate 13-acetate (PMA) for 5 days with or without ADA2 stimulation. The cells were harvested and washed twice with ice-cold FACS buffer (1×PBS, 0.5% FBS, 0.1% $NaN_3$). The washed cells were then fixed in BD CytoFix buffer (BDB 554655) at 4° C. for 30 min. The fixed cells were washed twice and stored in cold FACS buffer at 4° C. until staining.

For analysis of CD68 expression, $1 \times 10^6$ fixed cells were washed twice with ice-cold BD Perm/Wash buffer (contains saponin, BDB 554723), resuspended in the same buffer and incubated 4° C. for 30 min. Non-specific signals were blocked by incubating the cells with 2.5 mg of Human BD Fc Block (BDB 564220) in 100 ml of BD Perm/Wash buffer at room temperature for 10 min. The cells were then stained for CD68 expression by incubating in the dark with an Alexa Fluor 488-conjugated CD68 antibody from BioLegend (Cat #333812, clone Y1/82A) at 4° C. for 30 min. An Alexa Fluor 488-conjugated IgG2bk (Cat #400329, clone MPC-11) isotype control was used as background staining control. The cells were subsequently washed 3 times in BD Perm/Wash buffer and analyzed by Millipore's Guava EasyCyte HT Sampling Flow Cytometer.

Figure 18:
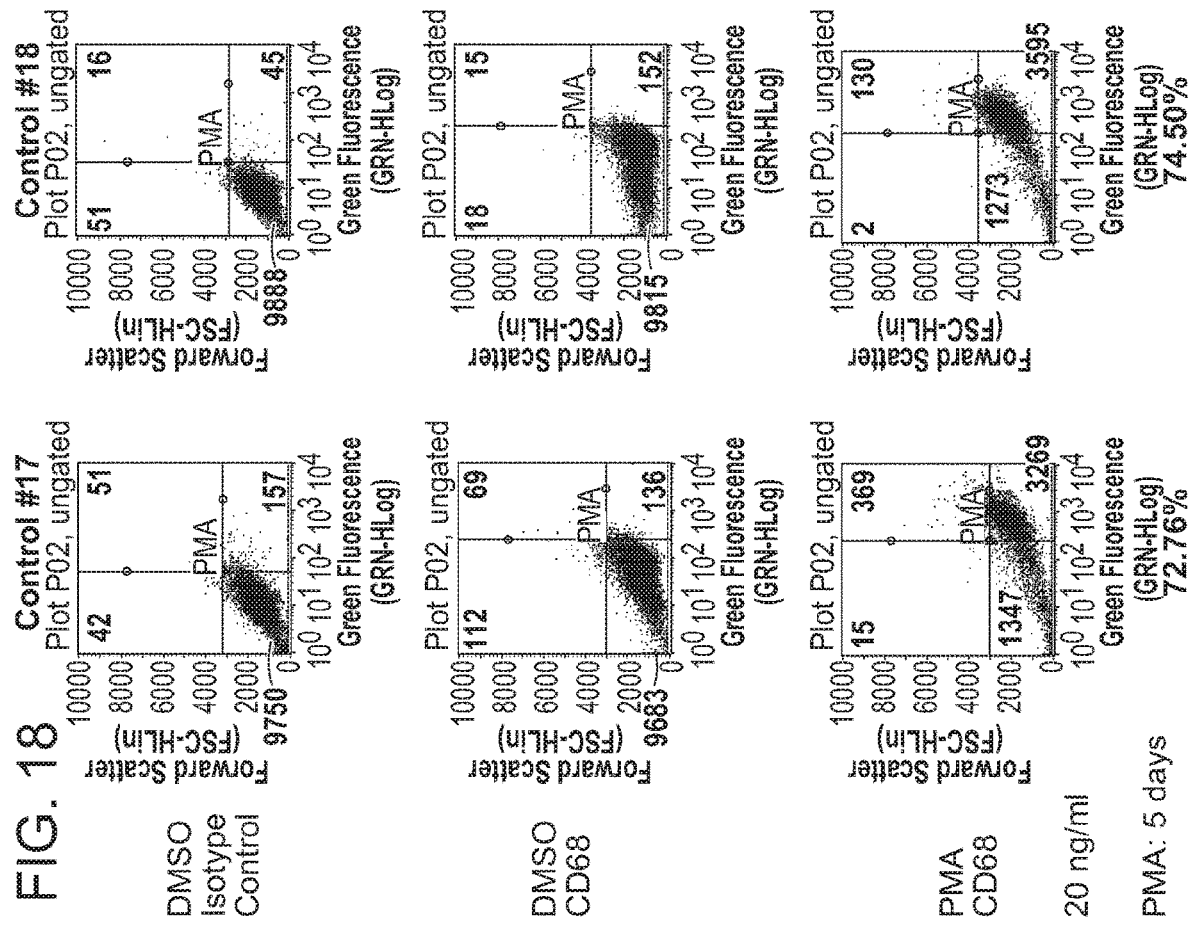
FIG. 18 depicts the results of a flow cytometric analysis of CD68 after silencing of ADA2 expression in PMA-treated U937 cells treated with CECR1 shRNA.

FIG. 17 shows that PMA treatment significantly increases expression of CD68, a pan marker for both M1 and M2 macrophages, in U937 cells transduced to express non-ADA2-specific shRNA (shRNA #15, #17, and #18). Almost all of the U937 cells infected with the control shRNA differentiated into macrophages after incubation with 20 ng/ml of PMA for 5 days. However, FIG. 16 shows that silencing of ADA2 in U937 cells by the transduced expression of CECR1 shRNA (CECR1 shRNA #25 or #51) substantially reduces the percentage of PMA-induced cells expressing CD68, The results confirm that ADA2 is critical in promoting the differentiation of monocytes into macrophages. FIG. 18 depicts similar results for U937 cells induced with PMA for 7 days, expressing control shRNA or CECR1 shRNA.

For analysis of CD163 or CD206 expression, 1×10⁶ fixed cells were washed twice with ice-cold BD Perm/Wash buffer (containing saponin, BDB 554723). Non-specific signals were blocked by incubating the cells with 2.5 mg of Human BD Fc Block (BDB 564220) in 100 ml of BD Perm/Wash buffer at room temperature for 10 min. The cells were then stained for CD163 or CD206 by incubating in the dark with an Alexa Fluor 488-conjugated CD163 antibody (Cat # FAB1607G) or CD206 antibody (Cat # FAB25342G) from R&D Systems at 4° C. for 30 min. An Alexa Fluor 488-conjugated IgG1 or IgG2A isotype control was used as background staining control. The cells were subsequently washed 3 times in BD Perm/Wash buffer and analyzed by Millipore's Guava EasyCyte HT Sampling Flow Cytometer.

Figure 19:
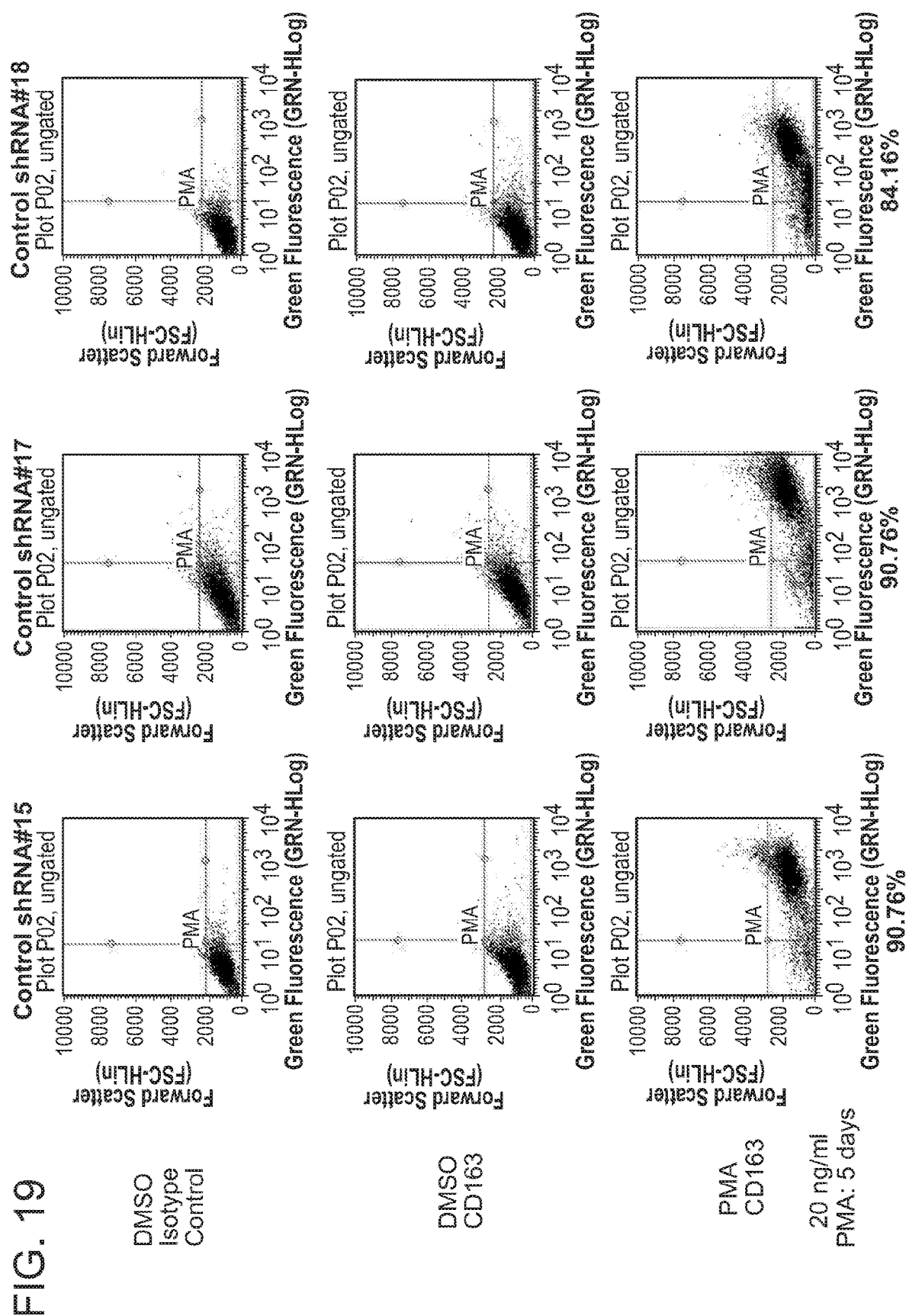
FIG. 19 depicts the results of a flow cytometric analysis of CD163 after silencing of ADA2 expression in PMA-treated U937 cells treated with CECR1 shRNA. PMA significantly increased the expression of CD163 in U937 cells transduced with control shRNA.
Figure 20:
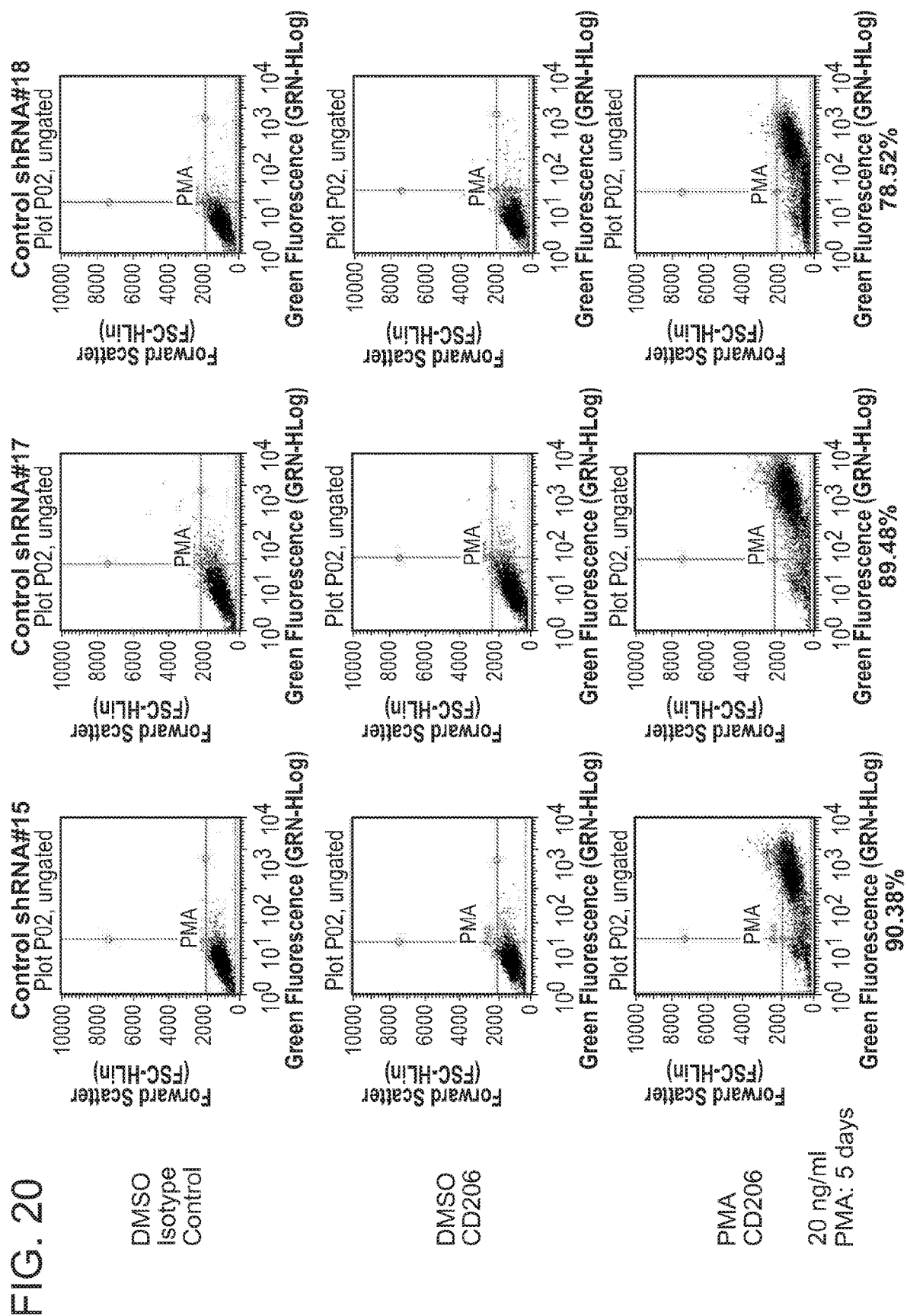
FIG. 20 depicts the results of a flow cytometric analysis of CD206 after silencing of ADA2 expression in PMA-treated U937 cells treated with CECR1 shRNA.
Figure 21:
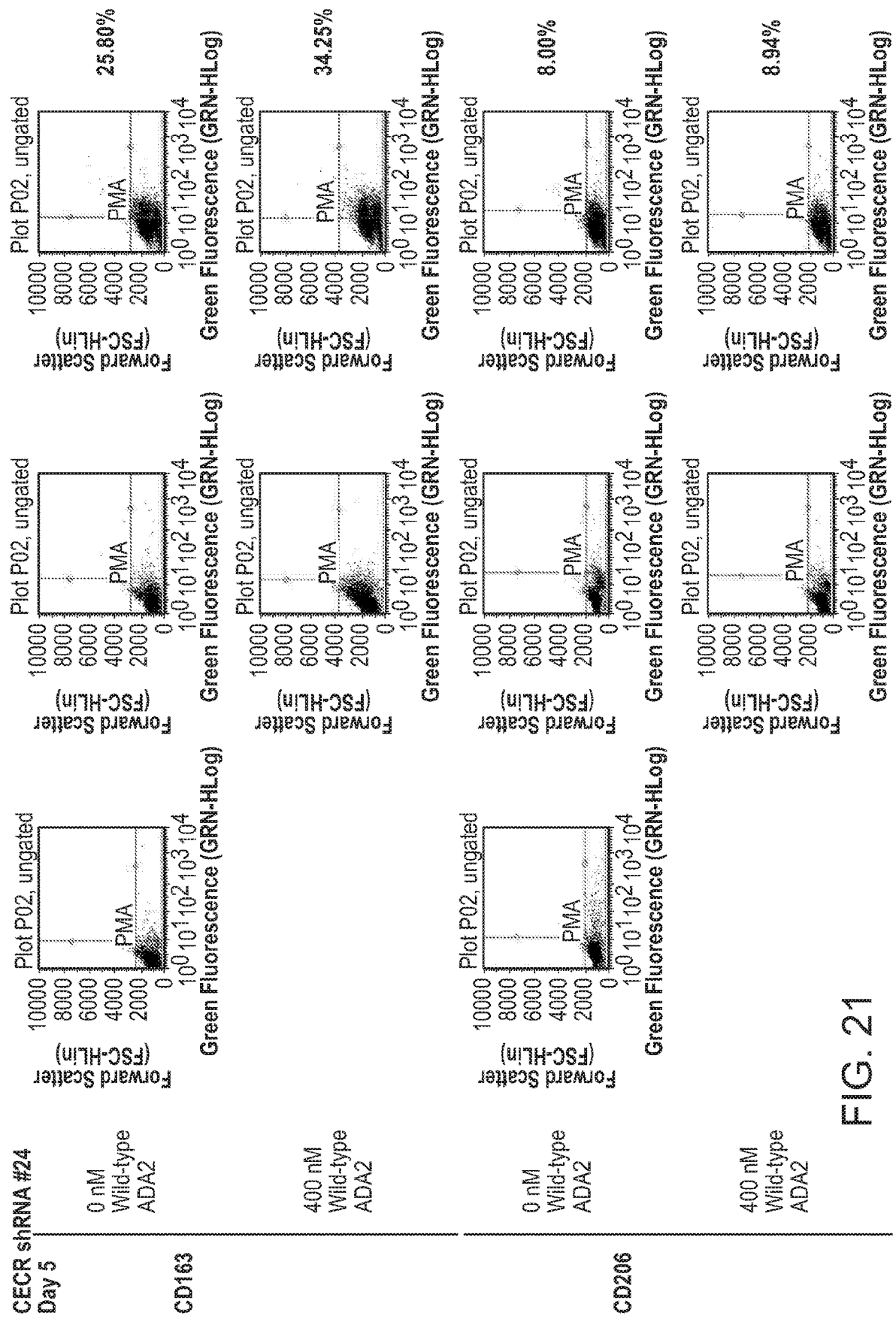
FIG. 21 depicts the results of a flow cytometric analysis of CD163 and CD206 after silencing of ADA2 expression in PMA-treated U937 cells treated with CECR1 shRNA.
Figure 22:
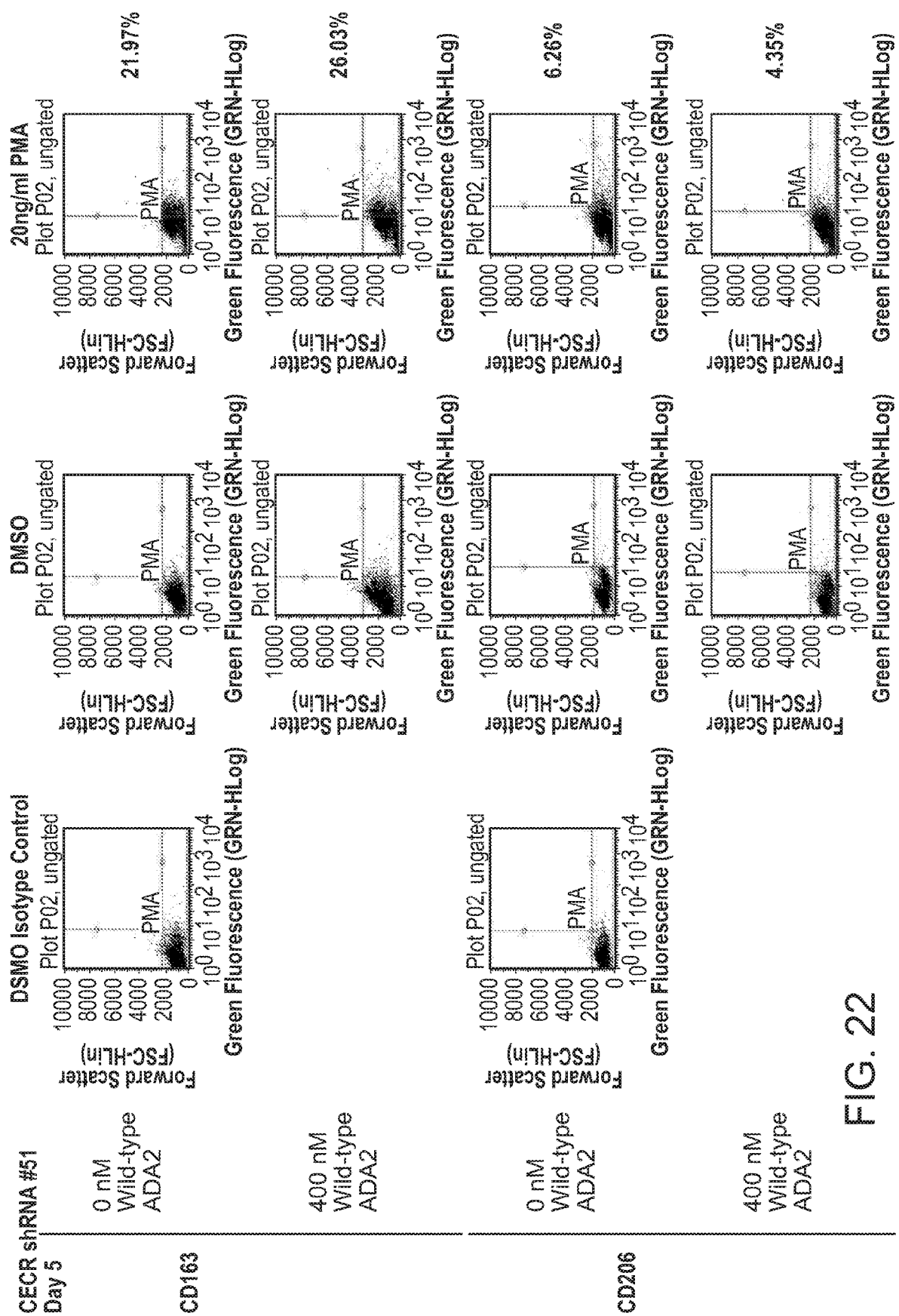
FIG. 22 depicts the results of a flow cytometric analysis of CD163 after silencing of ADA2 expression in PMA-treated U937 cells treated with CECR1 shRNA.

FIGS. 19 and 20 show that PMA treatment significantly increases expression of CD163 (FIG. 19) and CD206 (FIG. 20) in U937 cells transduced to express non-ADA2-specific shRNA (shRNA #15, #17 or #18). Figure M shows that silencing of ADA2 in U937 cells by transduced expression of CECR1 shRNA (CECR1 shRNA #25) substantially reduces PMA-induced CD163 and CD206 expression. FIG. 21 shows further that treatment with 400 nM of wild-type ADA2 increased expression of CD163, indicating that the administration of functional wild-type ADA2 can restore CD163 expression and promote M2 macrophage differentiation. FIG. 22 depicts similar results using a different CECR1 shRNA #51.

Example 10: In Vivo Disease Model

The ADA2 proteins and ADA2 fusion proteins of the invention can be used to treat subjects having an ADA-associated disease or disorder. In order to further study subject response, an ADA2 deficient zebrafish model was used (see, for example, Zhou et al., 2014, N. Engl. J. Med., 370(10):911-920), and the ADA2 protein was administered to the ADA2 deficient zebrafish to study their response.

Wild-type (Wt) rhADA2 protein and a SMARTpool of equal amounts of four siRNAs was injected into zebrafish in a knockdown rescue study. Knockdown of ADA2 gene (cerc1b) expression was performed with 3.125 uM of siRNA in 20 nL. A non-targeting siRNA sequence was used as a negative control. Wt rhADA2 protein was injected into zebrafish in 0.3 picograms (pg), 1 pg, 3 pg, or 10 pg amounts in 50 nL.

Figure 23A:
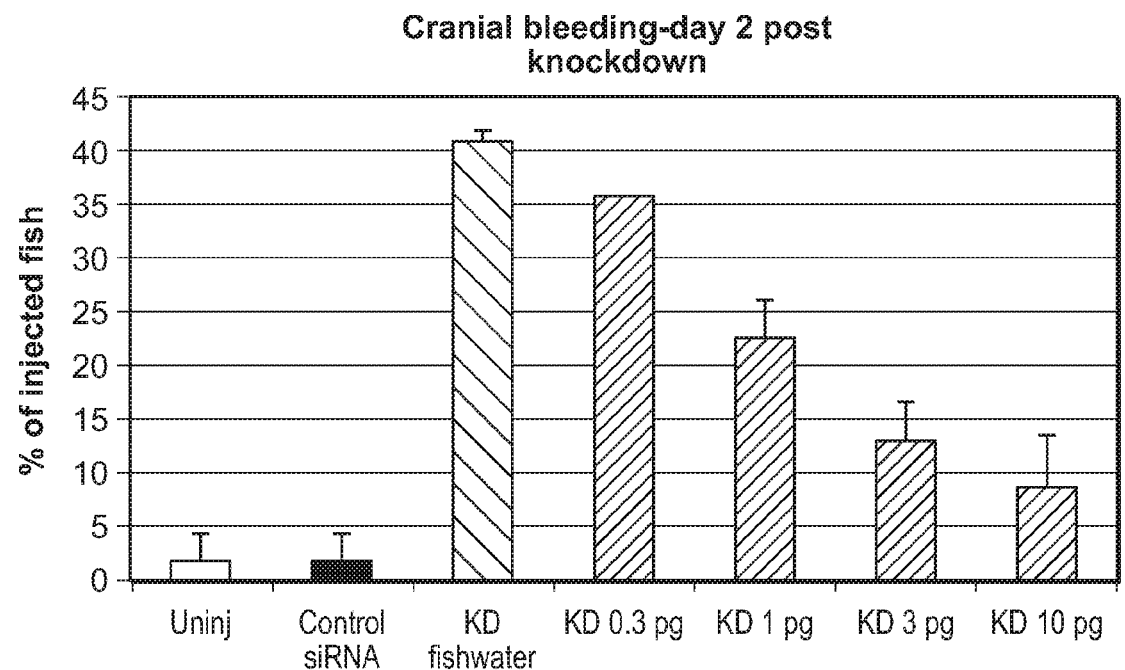
FIGS. 23A and 23B depict rescue of cranial bleeding in a zebrafish ADA2 knockdown model using ADA2 protein replacement.
Figure 23B:
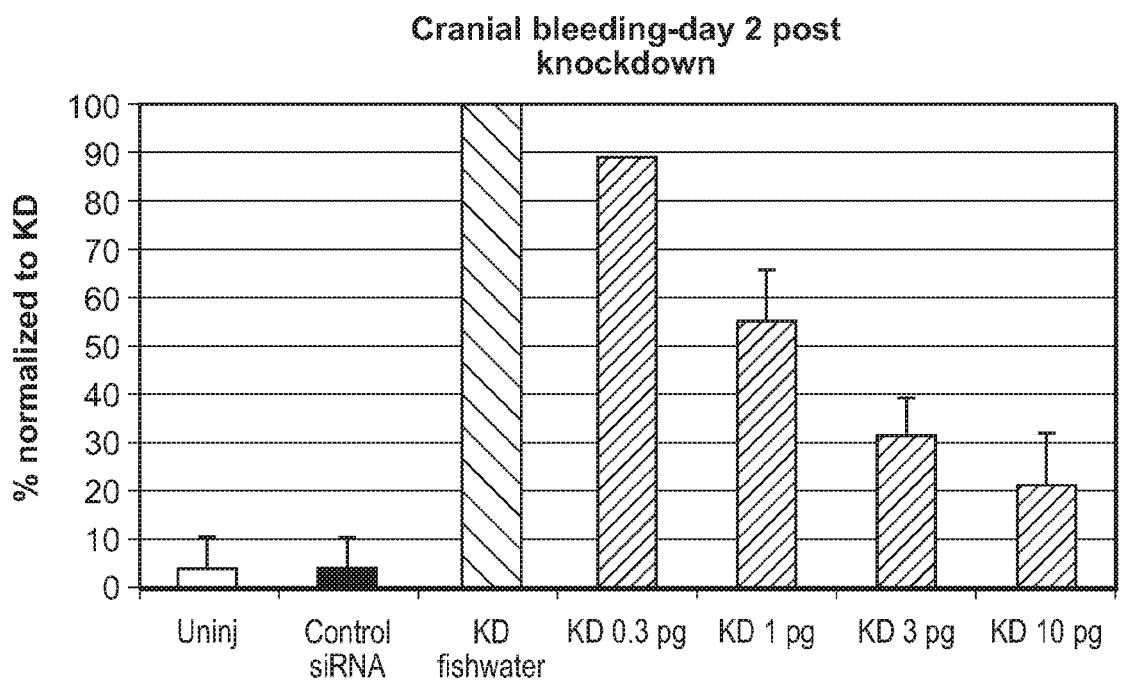

FIGS. 23A and 23B show that ADA2 protein replacement can rescue the cranial bleeding phenotype of zebrafish Jacking endogenous ADA2. The ADA2 gene (cecr1b) was knocked down by injecting four siRNAs into 1-2 cell stage zebrafish. The sense and antisense strands of the four siRNAs were as follows: sense strand GGGAAAGAUUAUAAGGAAAUU (SEQ ID NO: 37) and antisense strand UUUCCUUAUAAUCUUUCCCUU (SEQ ID NO: 38); sense strand CCAUUGAGAUGCAGA-GAAAUU (SEQ ID NO: 39) and antisense strand UUU-CUCUGCAUCUCAAUGGUU (SEQ ID NO: 40); sense strand AAAUUAAACUGCAGGGUAAUU (SEQ ID NO: 41) and antisense strand 5' PUUACCCUGCA-GUUUAAUUUUU (SEQ ID NO: 42); and sense strand CAGCACAACUGCAGGAUAAUU (SEQ ID NO: 43) and antisense strand UUAUCCUGCAGUUGUGCUGUU (SEQ ID NO: 44). Twenty four hours after siRNA injection, ADA2 protein or fish water (control) was injected in the yolk sac of fish embryos. Twenty four hours after ADA2 or fish water injection, the incidence of cranial bleeding was visualized under the microscope using O-dianisidine staining (red blood cell dye).

Figure 24:
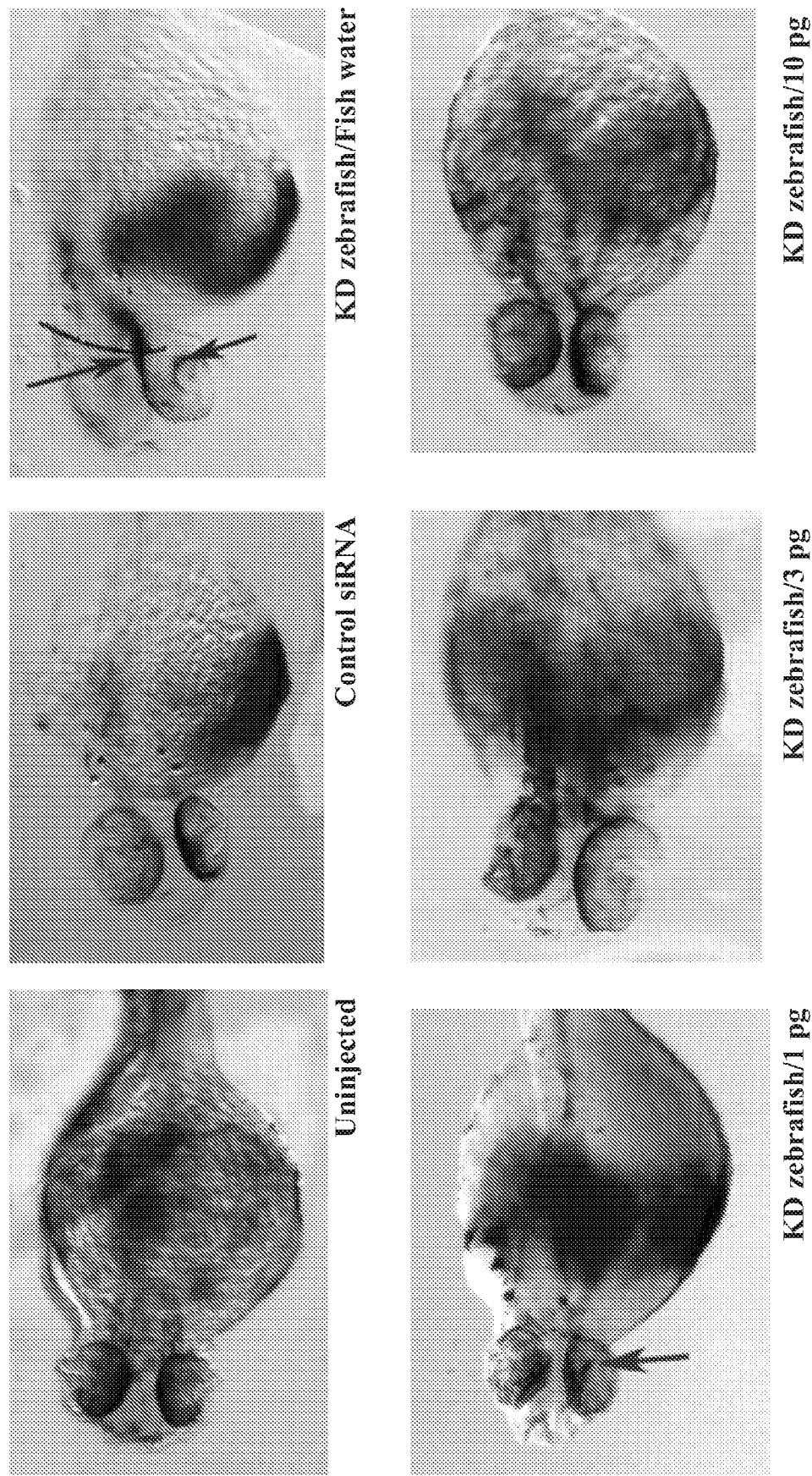
FIG. 24 depicts the cranial bleeding phenotype of rescued and control zebrafish embryos (2 dpf KD). Arrows indicate areas of cranial bleeding.

Knockdown of cecr1b using siRNAs led to a very significant increase in the incidence of cranial bleeding in zebrafish, as exhibited by the siRNA-fishwater control, indicating that ADA2 depletion can cause cranial bleeding. Wt rhADA2 protein replacement was shown to rescue cranial bleeding in a dose dependent manner (FIGS. 23A, 23B and 24). 10 pg of Wt rhADA2 produced the highest rate of rescue. FIG. 24 visually depicts the cranial bleeding phenotype in control and ADA2-rescued 2 dpf KD zebrafish embryos.

Example 11: Determination of Function Using Proliferation of CD4+ T Cells

In order to examine the function of the ADA2 proteins and ADA2 fusion proteins of the invention, proliferation of CD4+ T cells will be studied. To briefly summarize, CD4+ T cells and CD14+ monocytes will be isolated from PBMCs using a kit from Iltenyi Biotech, labeled, and analyzed via flow cytometry. Viability of macrophages will be assessed by staining the cells with a BD PharMingen Annexin V apoptosis detection kit, and visualizing them using microscopy.

Example 12: Methods of Treatment

ADA2 proteins and ADA2 fusion proteins of the invention will be formulated for pharmaceutical administration to humans. After administration, the clinical outcome of each patient will be monitored. The administration of the ADA2 proteins and ADA2 fusion proteins of the invention will reduce acute-phase reactants, reduce in gastrointestinal manifestations (e.g., abdominal pain), reduce in neurological manifestations (e.g., pain or numbness), reduce in stroke occurrence, ameliorate of fever and rash, reduce in neutrophil and macrophage infiltration in skin biopsies, and/or ameliorate hypertension in cases with renal hypertension.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising an isolated human adenosine deaminase 2 (ADA2) protein, or biologically active fragment thereof, and a pharmaceutically acceptable carrier, wherein the ADA2 protein, or biologically active fragment thereof, increases differentiation of monocytes into M2 macrophages, and wherein the ADA2 protein, or biologically active fragment thereof, comprises SEQ ID NO:1, or a functional peptide having one or more asparagine-to-alanine substitutions at amino acid position 127, 174, 185, and/or 378 of SEQ ID NO:1.

2. The pharmaceutical composition of claim 1, wherein the biologically active fragment comprises an adenosine deaminase domain of human adenosine deaminase 2 (ADA2).

3. The pharmaceutical composition of claim 1, wherein the macrophages are M2 macrophages that express cluster of differentiation 163 (CD163).

4. The pharmaceutical composition of claim 1, wherein the adenosine deaminase 2 (ADA2) protein, or biologically active fragment thereof, comprises one or more amino acid substitutions that remove one or more N-glycosylation sites, thereby increasing the half-life of the ADA2 protein, or biologically active fragment thereof.

5. A method of producing the pharmaceutical composition of claim 1 comprising an isolated human adenosine deaminase 2 (ADA2) protein, the method comprising culturing a host cell including a vector which comprises a nucleic acid encoding the ADA2 protein under conditions permitting the production of the ADA2 protein.

6. The method of claim 5, further comprising recovering the adenosine deaminase 2 (ADA2) fusion protein.

7. A method of producing the pharmaceutical composition of claim 1 comprising an isolated human adenosine deaminase 2 (ADA2) protein, the method comprising: expressing the human ADA2 protein in an oviduct cell of an avian, and isolating the human ADA2 protein from egg white of an egg produced by the avian.

8. The method of claim 7, wherein the avian comprises a transgene which includes a retroviral vector comprising a human adenosine deaminase 2 (ADA2) nucleic acid sequence operably linked to a promoter such that the avian expresses the human ADA2 nucleic acid in the oviduct cell of an avian.

9. A method of producing the pharmaceutical composition of claim 1 comprising an isolated human adenosine deaminase 2 (ADA2) protein, the method comprising: expressing the ADA2 protein in an oviduct cell of an avian, and isolating the ADA2 protein from egg white of an egg produced by the avian.

10. A method of treating a subject having an adenosine deaminase 2 (ADA2)-associated disease or disorder, the method comprising administering to the subject the pharmaceutical composition of claim 1.

11. The method of claim 10, wherein the adenosine deaminase 2 (ADA2)-associated disease or disorder is a disease or disorder selected from the group consisting of polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, low serum IgM, microscopic polyangitis, Wegener's granulamatosis, Churg-Strauss syndrome, Takayasu arteritis, giant cell arteritis, Livedoid vasculopathy and small vessel vasculitis.

12. The method of claim 11, wherein the adenosine deaminase 2 (ADA2)-associated disease or disorder is polyarteritis *nodosa* (PAN).

13. A method of increasing the differentiation of monocytes into M2 macrophages in a subject, the method comprising administering to the subject the pharmaceutical composition of claim 1.

14. The method of claim 13, wherein the subject has an adenosine deaminase 2 (ADA2)-associated disease or disorder.

15. The method of claim 14, wherein the adenosine deaminase 2 (ADA2)-associated disease or disorder is a disease or disorder selected from the group consisting of polyarteritis nodosa, Sneddon Syndrome, vasculitis, ischemic stroke, hemorrhagic stroke, lacunar stroke, aneurysm in the celiac artery, skin rash, skin necrosis, livedo racemosa, hepatosplenomegaly, organ failure, retinal artery occlusion, optic nerve atrophy, diplopia, cranial nerve palsy, strabismus, low serum IgM, microscopic polyangitis, Wegener's granulamatosis, Churg-Strauss syndrome, Takayasu arteritis, giant cell arteritis, Livedoid vasculopathy and small vessel vasculitis.

16. The method of claim 10, wherein the subject is a human.

17. The method of claim 13, wherein the subject is a human.

* * * * *

SEQUENCE LISTING

<160> NUMBER OF SEQ ID NOS: 44

<210> SEQ ID NO 1
<211> LENGTH: 511
<212> TYPE: PRT

-continued

<213> ORGANISM: Homo Sapiens

<400> SEQUENCE: 1

| Met | Leu | Val | Asp | Gly | Pro | Ser | Glu | Arg | Pro | Ala | Leu | Cys | Phe | Leu | Leu |
|---|---|---|---|---|---|---|---|---|---|---|---|---|---|---|---|
| 1 | | | | 5 | | | | | 10 | | | | | 15 | |

| Leu | Ala | Val | Ala | Met | Ser | Phe | Phe | Gly | Ser | Ala | Leu | Ser | Ile | Asp | Glu |
| | | | 20 | | | | | 25 | | | | | 30 | | |

| Thr | Arg | Ala | His | Leu | Leu | Leu | Lys | Glu | Lys | Met | Met | Arg | Leu | Gly | Gly |
| | | 35 | | | | | 40 | | | | | 45 | | | |

| Arg | Leu | Val | Leu | Asn | Thr | Lys | Glu | Glu | Leu | Ala | Asn | Glu | Arg | Leu | Met |
| 50 | | | | | 55 | | | | | 60 | | | | | |

| Thr | Leu | Lys | Ile | Ala | Glu | Met | Lys | Glu | Ala | Met | Arg | Thr | Leu | Ile | Phe |
| 65 | | | | | 70 | | | | | 75 | | | | | 80 |

| Pro | Pro | Ser | Met | His | Phe | Phe | Gln | Ala | Lys | His | Leu | Ile | Glu | Arg | Ser |
| | | | | 85 | | | | | 90 | | | | | 95 | |

| Gln | Val | Phe | Asn | Ile | Leu | Arg | Met | Met | Pro | Lys | Gly | Ala | Ala | Leu | His |
| | | | | 100 | | | | | 105 | | | | | 110 | |

| Leu | His | Asp | Ile | Gly | Ile | Val | Thr | Met | Asp | Trp | Leu | Val | Arg | Asn | Val |
| | | | 115 | | | | | 120 | | | | | 125 | | |

| Thr | Tyr | Arg | Pro | His | Cys | His | Ile | Cys | Phe | Thr | Pro | Arg | Gly | Ile | Met |
| | 130 | | | | | 135 | | | | | 140 | | | | |

| Gln | Phe | Arg | Phe | Ala | His | Pro | Thr | Pro | Arg | Pro | Ser | Glu | Lys | Cys | Ser |
| 145 | | | | | 150 | | | | | 155 | | | | | 160 |

| Lys | Trp | Ile | Leu | Leu | Glu | Asp | Tyr | Arg | Lys | Arg | Val | Gln | Asn | Val | Thr |
| | | | | 165 | | | | | 170 | | | | | 175 | |

| Glu | Phe | Asp | Asp | Ser | Leu | Leu | Arg | Asn | Phe | Thr | Leu | Val | Thr | Gln | His |
| | | | 180 | | | | | 185 | | | | | 190 | | |

| Pro | Glu | Val | Ile | Tyr | Thr | Asn | Gln | Asn | Val | Val | Trp | Ser | Lys | Phe | Glu |
| | | | 195 | | | | | 200 | | | | | 205 | | |

| Thr | Ile | Phe | Phe | Thr | Ile | Ser | Gly | Leu | Ile | His | Tyr | Ala | Pro | Val | Phe |
| | 210 | | | | | 215 | | | | | 220 | | | | |

| Arg | Asp | Tyr | Val | Phe | Arg | Ser | Met | Gln | Glu | Phe | Tyr | Glu | Asp | Asn | Val |
| 225 | | | | | 230 | | | | | 235 | | | | | 240 |

| Leu | Tyr | Met | Glu | Ile | Arg | Ala | Arg | Leu | Leu | Pro | Val | Tyr | Glu | Leu | Ser |
| | | | | 245 | | | | | 250 | | | | | 255 | |

| Gly | Glu | His | His | Asp | Glu | Glu | Trp | Ser | Val | Lys | Thr | Tyr | Gln | Glu | Val |
| | | | 260 | | | | | 265 | | | | | 270 | | |

| Ala | Gln | Lys | Phe | Val | Glu | Thr | His | Pro | Glu | Phe | Ile | Gly | Ile | Lys | Ile |
| | | 275 | | | | | 280 | | | | | 285 | | | |

| Ile | Tyr | Ser | Asp | His | Arg | Ser | Lys | Asp | Val | Ala | Val | Ile | Ala | Glu | Ser |
| | 290 | | | | | 295 | | | | | 300 | | | | |

| Ile | Arg | Met | Ala | Met | Gly | Leu | Arg | Ile | Lys | Phe | Pro | Thr | Val | Val | Ala |
| 305 | | | | | 310 | | | | | 315 | | | | | 320 |

| Gly | Phe | Asp | Leu | Val | Gly | His | Glu | Asp | Thr | Gly | His | Ser | Leu | His | Asp |
| | | | | 325 | | | | | 330 | | | | | 335 | |

| Tyr | Lys | Glu | Ala | Leu | Met | Ile | Pro | Ala | Lys | Asp | Gly | Val | Lys | Leu | Pro |
| | | | 340 | | | | | 345 | | | | | 350 | | |

| Tyr | Phe | Phe | His | Ala | Gly | Glu | Thr | Asp | Trp | Gln | Gly | Thr | Ser | Ile | Asp |
| | | | | 355 | | | | | 360 | | | | | 365 | |

| Arg | Asn | Ile | Leu | Asp | Ala | Leu | Met | Leu | Asn | Thr | Thr | Arg | Ile | Gly | His |
| | 370 | | | | | 375 | | | | | 380 | | | | |

| Gly | Phe | Ala | Leu | Ser | Lys | His | Pro | Ala | Val | Arg | Thr | Tyr | Ser | Trp | Lys |
| 385 | | | | | 390 | | | | | 395 | | | | | 400 |

Lys Asp Ile Pro Ile Glu Val Cys Pro Ile Ser Asn Gln Val Leu Lys
            405                 410                 415

Leu Val Ser Asp Leu Arg Asn His Pro Val Ala Thr Leu Met Ala Thr
        420                 425                 430

Gly His Pro Met Val Ile Ser Ser Asp Asp Pro Ala Met Phe Gly Ala
        435                 440                 445

Lys Gly Leu Ser Tyr Asp Phe Tyr Glu Val Phe Met Gly Ile Gly Gly
        450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
            485                 490                 495

Trp Lys Lys Arg Trp Asp Lys Phe Ile Ala Asp Val Ala Thr Lys
                500                 505                 510

<210> SEQ ID NO 2
<211> LENGTH: 1536
<212> TYPE: DNA
<213> ORGANISM: Homo Sapiens

<400> SEQUENCE: 2
atgttggtgg atggcccatc tgagcggcca gccctgtgct tcttgctgtt ggctgtggca      60
atgtctttct tcggctcagc tctatccata gatgaaacac gggcgcatct gttgttgaaa    120
gaaaagatga tgcggctggg ggggcggctg gtgctgaaca ccaaggagga gctggccaat    180
gagaggctca tgacgctcaa aatcgctgag atgaaggagg ccatgaggac cctgatattc    240
ccacccagca tgcactttt tccaggccaag catctcattg agagaagtca agtgtttaat    300
attctaagga tgatgccaaa aggggctgcc ttgcacctcc atgacattgg catcgtgact    360
atggactggc tggtgaggaa tgtcacctac aggcctcact gccacatctg tttcacccca    420 aggggggatca tgcagttcag atttgctcac ccaactcccc gtccatcaga aaatgttcc    480 aagtggattc tgctggagga ttatcggaag cgggtgcaga acgtcactga gtttgatgac    540
agcttgctga ggaatttcac tctggtgacc cagcacccgg aggtgattta cacaaaccaa    600
aatgttgtct ggtcgaaatt tgaaaccatc ttcttcacca tctctggtct catccattac    660
gcaccagtgt tcagagacta tgtcttccgg agcatgcagg agttctacga ggacaacgtg    720
ctctacatgg agatcagagc caggctgctg ccggtgtatg agctcagtgg agagcaccat    780
gacgaagagt ggtcagtgaa gacttaccag gaagtagctc agaagtttgt ggaaactcac    840
cctgagttta ttggaatcaa aatcatttat tcggatcaca gatccaaaga gtggctgtc    900 atcgcagaat ccatccgaat ggccatgggg ctccgaatca agttccccac ggtggtggca    960
gggtttgacc tggtggggca tgaggacact ggccactcct gcatgactaa caaggaagct   1020
ctgatgatcc ccgccaagga tggcgttaag ctgccttact tcttccacgc cggagaaaca   1080
gactggcagg gtacttccat agacaggaac attctggatg ctctgatgct gaacactacc   1140
agaatcggcc atggatttgc tttgagcaaa caccccgcag tcaggactta ctcctggaaa   1200
aaggacatcc ccatagaagt ctgtcccatc tctaaccagg tgctgaaact ggtgtctgac   1260
ttgaggaacc accctgtagc cactctgatg gccactgggc accccatggt gatcagctct   1320
gatgacccag ctatgtttgg tgccaaaggc ttgtcctatg atttctatga ggtcttcatg   1380
ggcattgggg gatgaaggc tgacctgagg accctcaaac agctggccat gaactctatc   1440
aagtacagta ccctgttgga gagtgagaaa aatactttca tggaaatctg gaagaagaga   1500
tgggataagt tcatagcaga tgtggctaca aagtga                                      1536

<210> SEQ ID NO 3
<211> LENGTH: 511
<212> TYPE: PRT
<213> ORGANISM: Artificial Sequence
<220> FEATURE:
<223> OTHER INFORMATION: Synthetic

<400> SEQUENCE: 3

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Lys Glu Lys Met Met Arg Leu Gly Gly
        35                  40              45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Ala Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
```

```
                  355                  360                  365
Arg Asn Ile Leu Asp Ala Leu Met Leu Asn Thr Thr Arg Ile Gly His
    370                  375                  380
Gly Phe Ala Leu Ser Lys His Pro Ala Val Arg Thr Tyr Ser Trp Lys
385                  390                  395                  400
Lys Asp Ile Pro Ile Glu Val Cys Pro Ile Ser Asn Gln Val Leu Lys
                405                  410                  415
Leu Val Ser Asp Leu Arg Asn His Pro Val Ala Thr Leu Met Ala Thr
                420                  425                  430
Gly His Pro Met Val Ile Ser Ser Asp Asp Pro Ala Met Phe Gly Ala
            435                  440                  445
Lys Gly Leu Ser Tyr Asp Phe Tyr Glu Val Phe Met Gly Ile Gly Gly
            450                  455                  460
Met Lys Ala Asp Leu Arg Thr Leu Lys Gln Leu Ala Met Asn Ser Ile
465                  470                  475                  480
Lys Tyr Ser Thr Leu Leu Glu Ser Glu Lys Asn Thr Phe Met Glu Ile
                485                  490                  495
Trp Lys Lys Arg Trp Asp Lys Phe Ile Ala Asp Val Ala Thr Lys
                500                  505                  510
```

<210> SEQ ID NO 4
<211> LENGTH: 1536
<212> TYPE: DNA
<213> ORGANISM: Homo sapiens

<400> SEQUENCE: 4

```
atgttggtgg atgcccatc  tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa aatcgctgag atgaaggagg ccatgaggac cctgatattc     240
ccacccagca tgcactttt  ccaggccaag catctcattg agagaagtca agtgtttaat     300
attctaagga tgatgccaaa aggggctgcc ttgcacctcc atgacattgg catcgtgact     360
atggactggc tggtgagggc cgtcacctac aggcctcact gccacatctg tttcacccca     420
agggggatca tgcagttcag atttgctcac ccaactcccc gtccatcaga aaatgttcc      480
aagtggattc tgctggagga ttatcggaag cgggtgcaga acgtcactga gtttgatgac     540
agcttgctga ggaatttcac tctggtgacc agcacccgg  aggtgattta cacaaaccaa     600
aatgttgtct ggtcgaaatt tgaaaccatc ttcttcacca tctctggtct catccattac     660
gctccagtgt tcagagacta tgtcttccgg agcatgcagg agttctacga ggacaacgtg     720
ctctacatgg agatcagagc caggctgctg ccggtgtatg agctcagtgg agagcaccat     780
gacgaagagt ggtcagtgaa gacttatcag gaagtagctc agaagtttgt ggaaactcat     840
cctgagttta ttggaatcaa atcatttat  tcggatcaca gatccaaaga gtgtggctgtc    900
atcgcagaat ccatccgaat ggccatgggg ctccgaatca agttccccac ggtggtggca     960
gggtttgacc tggtggggca tgaggacact ggccactcct tgcatgacta caaggaagct    1020
ctgatgatcc ccgccaagga tggcgttaag ctgccttact tcttccacgc cggagaaaca    1080
gactggcagg gtacttccat agacaggaac attctggatg ctctgatgct gaacactacc    1140
agaatcggcc atgatttgc  tttgagcaaa caccccgcag tcaggactta ttcctggaaa    1200
aaggacatcc ccatagaagt ctgtcccatc tctaaccagg tgctgaaact ggtgtctgac    1260
```

-continued

```
ttgaggaacc accctgtagc cactctgatg gccactgggc accccatggt gatcagctct    1320
gatgacccag ctatgtttgg tgccaaaggc ttgtcctatg atttctatga ggtcttcatg    1380
ggcattgggg ggatgaaggc tgatctgagg accctcaaac agctggccat gaactctatc    1440
aagtacagta ccctgttgga gagtgagaaa aatactttca tggaaatatg gaagaagaga    1500
tgggataagt tcatagcaga tgtggctaca aagtga                              1536
```

<210> SEQ ID NO 5
<211> LENGTH: 511
<212> TYPE: PRT
<213> ORGANISM: Artificial Sequence
<220> FEATURE:
<223> OTHER INFORMATION: Synthetic

<400> SEQUENCE: 5

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Ala Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320
```

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
                340                 345                 350

Tyr Phe Phe His Ala Gly Glu Thr Asp Trp Gln Gly Thr Ser Ile Asp
                355                 360                 365

Arg Asn Ile Leu Asp Ala Leu Met Leu Asn Thr Thr Arg Ile Gly His
                370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
                420                 425                 430

Gly His Pro Met Val Ile Ser Ser Asp Asp Pro Ala Met Phe Gly Ala
                435                 440                 445

Lys Gly Leu Ser Tyr Asp Phe Tyr Glu Val Phe Met Gly Ile Gly Gly
                450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
                500                 505                 510

<210> SEQ ID NO 6
<211> LENGTH: 1536
<212> TYPE: DNA
<213> ORGANISM: Artificial Sequence
<220> FEATURE:
<223> OTHER INFORMATION: Synthetic

<400> SEQUENCE: 6
atgttggtgg atggcccatc tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa atcgctgaga tgaaggagg ccatgaggac cctgatattc      240
ccacccagca tgcactttt ccaggccaag catctcattg agagaagtca agtgtttaat      300
attctaagga tgatgccaaa aggggctgcc ttgcacctcc atgacattgg catcgtgact     360
atggactggc tggtgaggaa tgtcacctac aggcctcact gccacatctg tttcacccca     420 aggggggatca tgcagttcag atttgctcac ccaactcccc gtccatcaga aaaatgttcc     480
aagtggattc tgctggagga ttatcggaag cgggtgcagg ccgtcactga gtttgatgac     540
agcttgctga ggaatttcac tctggtgacc agcaccccgg aggtgattta cacaaaccaa     600
aatgttgtct ggtcgaaatt tgaaaccatc ttcttcacca tctctggtct catccattac     660
gctccagtgt tcagagacta tgtcttccgg agcatgcagg agttctacga ggacaacgtg     720
ctctacatgg agatcagagc caggctgctg ccggtgtatg agctcagtgg agagcaccat     780
gacgaagagt ggtcagtgaa gacttatcag gaagtagctc agaagtttgt ggaaactcat     840 cctgagtta ttggaatcaa aatcatttat tcggatcaca gatccaaaga tgtggctgtc      900
atcgcagaat ccatccgaat ggccatgggg ctccgaatca agttccccac ggtggtggca     960

```
gggtttgacc tggtggggca tgaggacact ggccactcct tgcatgacta caaggaagct    1020
ctgatgatcc ccgccaagga tggcgttaag ctgccttact tcttccacgc cggagaaaca    1080
gactggcagg gtacttccat agacaggaac attctggatg ctctgatgct gaacactacc    1140
agaatcggcc atggatttgc tttgagcaaa caccccgcag tcaggactta ttcctggaaa    1200
aaggacatcc ccatagaagt ctgtcccatc tctaaccagg tgctgaaact ggtgtctgac    1260
ttgaggaacc accctgtagc cactctgatg gccactgggc accccatggt gatcagctct    1320
gatgacccag ctatgtttgg tgccaaaggc ttgtcctatg atttctatga ggtcttcatg    1380
ggcattgggg ggatgaaggc tgatctgagg accctcaaac agctggccat gaactctatc    1440
aagtacagta ccctgttgga gagtgagaaa aatactttca tggaaatatg gaagaagaga    1500
tgggataagt tcatagcaga tgtggctaca aagtga                              1536
```

<210> SEQ ID NO 7
<211> LENGTH: 511
<212> TYPE: PRT
<213> ORGANISM: Artificial Sequence
<220> FEATURE:
<223> OTHER INFORMATION: Synthetic

<400> SEQUENCE: 7

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Ala Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
```

```
                    260                 265                 270
Ala Gln Lys Phe Val Glu Thr His Pro Glu Phe Ile Gly Ile Lys Ile
            275                 280                 285

Ile Tyr Ser Asp His Arg Ser Lys Asp Val Ala Val Ile Ala Glu Ser
        290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
        355                 360                 365

Arg Asn Ile Leu Asp Ala Leu Met Leu Asn Thr Thr Arg Ile Gly His
370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Asp Pro Ala Met Phe Gly Ala
        435                 440                 445

Lys Gly Leu Ser Tyr Asp Phe Tyr Glu Val Phe Met Gly Ile Gly Gly
    450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
            500                 505                 510

<210> SEQ ID NO 8
<211> LENGTH: 1536
<212> TYPE: DNA
<213> ORGANISM: Artificial Sequence
<220> FEATURE:
<223> OTHER INFORMATION: Synthetic

<400> SEQUENCE: 8
atgttggtgg atggcccatc tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa atcgctgagc atgaaggagg ccatgaggac cctgatattc     240
ccacccagca tgcactttt tccaggccaag catctcattg agagaagtca agtgtttaat     300
attctaagga tgatgccaaa aggggctgcc ttgcacctcc atgacattgg catcgtgact     360
atggactggc tggtgaggaa tgtcacctac aggcctcact gccacatctg tttcaccccc     420 aggggatca tgcagttcag atttgctcac ccaactcccc gtccatcaga aaatgttcc      480 aagtggattc tgctggagga ttatcggaag cgggtgcaga acgtcactga gtttgatgac     540
agcttgctga ggccttcac tctggtgacc cagcaccgg aggtgattta cacaaaccaa     600
aatgttgtct ggtcgaaatt tgaaaccatc ttcttcacca tctctggtct catccattac     660
```

```
gctccagtgt tcagagacta tgtcttccgg agcatgcagg agttctacga ggacaacgtg      720
ctctacatgg agatcagagc caggctgctg ccggtgtatg agctcagtgg agagcaccat      780
gacgaagagt ggtcagtgaa gacttatcag gaagtagctc agaagtttgt ggaaactcat      840
cctgagttta ttggaatcaa aatcatttat tcggatcaca gatccaaaga tgtggctgtc      900
atcgcagaat ccatccgaat ggccatgggg ctccgaatca agttccccac ggtggtggca      960
gggtttgacc tggtggggca tgaggacact ggccactcct tgcatgacta caaggaagct     1020
ctgatgatcc ccgccaagga tggcgttaag ctgccttact tcttccacgc cggagaaaca     1080
gactggcagg gtacttccat agacaggaac attctggatg ctctgatgct gaacactacc     1140
agaatcggcc atggatttgc tttgagcaaa cacccgcag tcaggactta ttcctggaaa      1200
aaggacatcc ccatagaagt ctgtcccatc tctaaccagg tgctgaaact ggtgtctgac     1260
ttgaggaacc accctgtagc cactctgatg gccactgggc accccatggt gatcagctct     1320
gatgacccag ctatgtttgg tgccaaaggc ttgtcctatg atttctatga ggtcttcatg     1380
ggcattgggg ggatgaaggc tgatctgagg accctcaaac agctggccat gaactctatc     1440
aagtacagta ccctgttgga gagtgagaaa atactttca tggaaatatg gaagaagaga      1500
tgggataagt tcatagcaga tgtggctaca aagtga                                1536

<210> SEQ ID NO 9
<211> LENGTH: 511
<212> TYPE: PRT
<213> ORGANISM: Artificial Sequence
<220> FEATURE:
<223> OTHER INFORMATION: Synthetic

<400> SEQUENCE: 9

Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205
```

Thr Ile Phe Phe Thr Ile Ser Gly Leu Ile His Tyr Ala Pro Val Phe
210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
            245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
        355                 360                 365

Arg Asn Ile Leu Asp Ala Leu Met Leu Ala Thr Thr Arg Ile Gly His
370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Asp Pro Ala Met Phe Gly Ala
        435                 440                 445

Lys Gly Leu Ser Tyr Asp Phe Tyr Glu Val Phe Met Gly Ile Gly Gly
450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
            500                 505                 510

<210> SEQ ID NO 10
<211> LENGTH: 1536
<212> TYPE: DNA
<213> ORGANISM: Artificial Sequence
<220> FEATURE:
<223> OTHER INFORMATION: Synthetic

<400> SEQUENCE: 10
atgttggtgg atggcccatc tgagcggcca gccctgtgct tcttgctgtt ggctgtggca      60
atgtctttct tcggctctgc tctatccata gatgaaacac gggcgcatct gttgttgaaa     120 gaaagatga tgcggctggg ggggcggctg gtgctgaaca ccaaggagga gctggccaat     180
gagaggctca tgacgctcaa atcgctgag atgaaggagg ccatgaggac cctgatattc     240
ccacccagca tgcactttt ccaggccaag catctcattg agagaagtca agtgtttaat     300
attctaagga tgatgccaaa aggggctgcc ttgcacctcc atgacattgg catcgtgact     360

```
atggactggc tggtgaggaa tgtcacctac aggcctcact gccacatctg tttcacccca    420
agggggatca tgcagttcag atttgctcac ccaactcccc gtccatcaga aaatgttcc     480 aagtggattc tgctggagga ttatcggaag cgggtgcaga acgtcactga gtttgatgac    540
agcttgctga ggaatttcac tctggtgacc cagcacccgg aggtgattta cacaaaccaa    600
aatgttgtct ggtcgaaatt tgaaaccatc ttcttcacca tctctggtct catccattac    660
gctccagtgt tcagagacta tgtcttccgg agcatgcagg agttctacga ggacaacgtg    720
ctctacatgg agatcagagc caggctgctg ccggtgtatg agctcagtgg agagcaccat    780
gacgaagagt ggtcagtgaa gacttatcag gaagtagctc agaagtttgt ggaaactcat    840
cctgagttta ttggaatcaa aatcatttat tcggatcaca gatccaaaga tgtggctgtc    900
atcgcagaat ccatccgaat ggccatgggg ctccgaatca agttcccac ggtggtggca     960 gggtttgacc tggtggggca tgaggacact ggccactcct gcatgactaa caaggaagct   1020
ctgatgatcc ccgccaagga tggcgttaag ctgccttact tcttccacgc cggagaaaca   1080
gactggcagg tacttccat agacaggaac attctggatg ctctgatgct ggccactacc    1140
agaatcggcc atggatttgc tttgagcaaa caccccgcag tcaggactta ttcctggaaa   1200
aaggacatcc ccatagaagt ctgtcccatc tctaaccagg tgctgaaact ggtgtctgac   1260
ttgaggaacc accctgtagc cactctgatg gccactgggc accccatggt gatcagctct   1320
gatgacccag ctatgtttgg tgccaaaggc ttgtcctatg atttctatga ggtcttcatg   1380
ggcattgggg ggatgaaggc tgatctgagg accctcaaac agctggccat gaactctatc   1440
aagtacagta ccctgttgga gagtgagaaa aatactttca tggaaatatg gaagaagaga   1500
tgggataagt tcatagcaga tgtggctaca aagtga                             1536
```

<210> SEQ ID NO 11
<211> LENGTH: 511
<212> TYPE: PRT
<213> ORGANISM: Artificial Sequence
<220> FEATURE:
<223> OTHER INFORMATION: Synthetic

<400> SEQUENCE: 11

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160
```

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
        355                 360                 365

Arg Asn Ile Leu Asp Ala Leu Met Leu Asn Thr Thr Arg Ile Gly His
    370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Glu Asp Pro Ala Met Phe Gly Ala
        435                 440                 445

Lys Gly Leu Ser Tyr Asp Phe Tyr Glu Val Phe Met Gly Ile Gly Gly
    450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
            500                 505                 510

<210> SEQ ID NO 12
<211> LENGTH: 1536
<212> TYPE: DNA
<213> ORGANISM: Artificial Sequence
<220> FEATURE:
<223> OTHER INFORMATION: Synthetic

<400> SEQUENCE: 12
atgctggtcg acggcccttc agaacggcct gctctgtgct tcctgctgct ggctgtcgca         60

```
atgagcttct tggtagtgc cctgtccatc gacgagaccc gggcccacct gctgctgaag    120
gagaagatga tgaggctggg cggcagactg gtgctgaaca ccaaggagga gctggctaat    180
gagcggctga tgacactgaa gatcgccgag atgaaggagg ctatgaggac cctgatcttc    240
ccccttcca tgcacttctt tcaagccaag cacctgattg agagatctca ggtgtttaac    300
atcctgcgga tgatgcccaa gggcgccgct ctgcacctgc acgacatcgg catcgtgacc    360
atggattggc tggtgcggaa tgtgacatac aggcctcact gccacatctg tttcacccca    420
cggggcatca tgcagttcag atttgcccac ccaacacccc ggccttctga agtgcagc     480
aagtggatcc tgctggagga ctaccggaag gggtgcaga cgtgaccga gttcgacgat     540
tccctgctgc ggaacttcac cctggtgaca cagcaccctg aagtgatcta caccaaccag    600
aatgtggtgt ggtctaagtt cgagaccatc ttctttacaa tcagcggcct gatccactac    660
gccccagtgt tcagagacta cgtgttccgg agcatgcagg agttttacga ggataacgtg    720
ctgtatatgg agatcagagc tcggctgctg cccgtgtacg agctgtccgg cgagcaccac    780
gatgaggagt ggtctgtgaa gacctaccag gaggtggccc agaagttcgt ggagacacac    840
cccgagttta tcggcatcaa gatcatctat tccgaccacc ggtctaagga tgtggccgtg    900
atcgctgaga gcatccggat ggccatgggc ctgaggatca agttccctac agtggtggct    960
ggctttgacc tggtcggcca cgaggataca ggccactccc tgcacgacta caaggaggcc   1020
ctgatgatcc ccgctaagga tggcgtgaag ctgccttatt tctttcacgc cggcgagacc   1080
gattggcagg gcacaagcat cgacaggaac atcctggatg ctctgatgct gaataccaca   1140
agaatcggcc acggcttcgc cctgagcaag caccctgctg tgcggaccta ctcctggaag   1200
aaggacatcc aatcgaggt gtgccccatc tctaaccaag tgctgaagct ggtgagcgat   1260
ctgcggaatc acccagtggc caccctgatg gctacaggcc acccaatggt catcagctcc   1320
gaagatcccg ccatgtttgg cgctaagggc ctgtcttacg acttctatga ggtgtttatg   1380
ggcatcggcg gcatgaaggc cgatctgcgg accctgaagc agctggctat gaacagcatc   1440
aagtattcca cactgctgga gagcgagaag aatacattca tggaaatctg gaagaaacgg   1500
tgggacaagt tcatcgctga cgtggctact aaatga                             1536
```

<210> SEQ ID NO 13
<211> LENGTH: 511
<212> TYPE: PRT
<213> ORGANISM: Artificial Sequence
<220> FEATURE:
<223> OTHER INFORMATION: Synthetic

<400> SEQUENCE: 13

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
```

```
                100             105             110
Leu His Asp Ile Gly Ile Val Thr Met Asp Trp Leu Val Arg Asn Val
            115                 120             125
Thr Tyr Arg Pro His Cys His Ile Cys Phe Thr Pro Arg Gly Ile Met
            130                 135             140
Gln Phe Arg Phe Ala His Pro Thr Pro Arg Pro Ser Glu Lys Cys Ser
145             150                 155                     160
Lys Trp Ile Leu Leu Glu Asp Tyr Arg Lys Arg Val Gln Asn Val Thr
                165                 170             175
Glu Phe Asp Asp Ser Leu Leu Arg Asn Phe Thr Leu Val Thr Gln His
            180                 185             190
Pro Glu Val Ile Tyr Thr Asn Gln Asn Val Val Trp Ser Lys Phe Glu
            195                 200             205
Thr Ile Phe Phe Thr Ile Ser Gly Leu Ile His Tyr Ala Pro Val Phe
            210                 215             220
Arg Asp Tyr Val Phe Arg Ser Met Gln Glu Phe Tyr Glu Asp Asn Val
225             230                 235                     240
Leu Tyr Met Glu Ile Arg Ala Arg Leu Leu Pro Val Tyr Glu Leu Ser
                245                 250             255
Gly Glu His His Asp Glu Glu Trp Ser Val Lys Thr Tyr Gln Glu Val
            260                 265             270
Ala Gln Lys Phe Val Glu Thr His Pro Glu Phe Ile Gly Ile Lys Ile
            275                 280             285
Ile Tyr Ser Asp His Arg Ser Lys Asp Val Ala Val Ile Ala Glu Ser
            290                 295             300
Ile Arg Met Ala Met Gly Leu Arg Ile Lys Phe Pro Thr Val Val Ala
305             310                 315                     320
Gly Phe Asp Leu Val Gly His Glu Asp Thr Gly His Ser Leu His Asp
                325                 330             335
Tyr Lys Glu Ala Leu Met Ile Pro Ala Lys Asp Gly Val Lys Leu Pro
            340                 345             350
Tyr Phe Phe His Ala Gly Glu Thr Asp Trp Gln Gly Thr Ser Ile Asp
            355                 360             365
Arg Asn Ile Leu Asp Ala Leu Met Leu Asn Thr Thr Arg Ile Gly His
370             375                 380
Gly Phe Ala Leu Ser Lys His Pro Ala Val Arg Thr Tyr Ser Trp Lys
385             390                 395                     400
Lys Asp Ile Pro Ile Glu Val Cys Pro Ile Ser Asn Gln Val Leu Lys
                405                 410             415
Leu Val Ser Asp Leu Arg Asn His Pro Val Ala Thr Leu Met Ala Thr
            420                 425             430
Gly His Pro Met Val Ile Ser Ser Asp Ala Pro Ala Met Phe Gly Ala
            435                 440             445
Lys Gly Leu Ser Tyr Asp Phe Tyr Glu Val Phe Met Gly Ile Gly Gly
            450                 455             460
Met Lys Ala Asp Leu Arg Thr Leu Lys Gln Leu Ala Met Asn Ser Ile
465                 470                 475                 480
Lys Tyr Ser Thr Leu Leu Glu Ser Glu Lys Asn Thr Phe Met Glu Ile
                485                 490             495
Trp Lys Lys Arg Trp Asp Lys Phe Ile Ala Asp Val Ala Thr Lys
                500                 505             510

<210> SEQ ID NO 14
```

<211> LENGTH: 1536
<212> TYPE: DNA
<213> ORGANISM: Artificial Sequence
<220> FEATURE:
<223> OTHER INFORMATION: Synthetic

<400> SEQUENCE: 14

| | | | | | |
|---|---|---|---|---|---|
| atgctggtcg | acggcccttc | agaacggcct | gctctgtgct | tcctgctgct | ggctgtcgca | 60 |
| atgagcttct | ttggtagtgc | cctgtccatc | gacgagaccc | gggcccacct | gctgctgaag | 120 |
| gagaagatga | tgaggctggg | cggcagactg | gtgctgaaca | ccaaggagga | gctggctaat | 180 |
| gagcggctga | tgacactgaa | gatcgccgag | atgaaggagg | ctatgaggac | cctgatcttc | 240 |
| cccccttcca | tgcacttctt | tcaagccaag | cacctgattg | agagatctca | ggtgtttaac | 300 |
| atcctgcgga | tgatgcccaa | gggcgccgct | ctgcacctgc | acgacatcgg | catcgtgacc | 360 |
| atggattggc | tggtgcggaa | tgtgacatac | aggcctcact | gccacatctg | tttcacccca | 420 |
| cggggcatca | tgcagttcag | atttgcccac | ccaacacccc | ggccttctga | aagtgcagc | 480 |
| aagtggatcc | tgctggagga | ctaccggaag | agggtgcaga | acgtgaccga | gttcgacgat | 540 |
| tccctgctgc | ggaacttcac | cctggtgaca | cagcaccctg | aagtgatcta | caccaaccag | 600 |
| aatgtggtgt | ggtctaagtt | cgagaccatc | ttctttacaa | tcagcggcct | gatccactac | 660 |
| gccccagtgt | tcagagacta | cgtgttccgg | agcatgcagg | agttttacga | ggataacgtg | 720 |
| ctgtatatgg | agatcagagc | tcggctgctg | ccgtgtacg | agctgtccgg | cgagcaccac | 780 |
| gatgaggagt | ggtctgtgaa | gacctaccag | gaggtggccc | agaagttcgt | ggagacacac | 840 |
| cccgagttta | tcggcatcaa | gatcatctat | tccgaccacc | ggtctaagga | tgtggccgtg | 900 |
| atcgctgaga | gcatccggat | ggccatgggc | ctgaggatca | agttccctac | agtggtggct | 960 |
| ggctttgacc | tggtcggcca | cgaggataca | ggccactccc | tgcacgacta | caaggaggcc | 1020 |
| ctgatgatcc | ccgctaagga | tggcgtgaag | ctgccttatt | tctttcacgc | cggcgagacc | 1080 |
| gattggcagg | gcacaagcat | cgacaggaac | atcctggatg | ctctgatgct | gaataccaca | 1140 |
| agaatcggcc | acggcttcgc | cctgagcaag | caccctgctg | tgcggaccta | ctcctggaag | 1200 |
| aaggacatcc | caatcgaggt | gtgccccatc | tctaaccaag | tgctgaagct | ggtgagcgat | 1260 |
| ctgcggaatc | acccagtggc | caccctgatg | gctacaggcc | acccaatggt | catcagctcc | 1320 |
| gacgctcccg | ccatgtttgg | cgctaagggc | ctgtcttacg | acttctatga | ggtgtttatg | 1380 |
| ggcatcggcg | gcatgaaggc | cgatctgcgg | accctgaagc | agctggctat | gaacagcatc | 1440 |
| aagtattcca | cactgctgga | gagcgagaag | aatacattca | tggaaatctg | gaagaaacgg | 1500 |
| tgggacaagt | tcatcgctga | cgtggctact | aaatga | | 1536 |

<210> SEQ ID NO 15
<211> LENGTH: 511
<212> TYPE: PRT
<213> ORGANISM: Artificial Sequence
<220> FEATURE:
<223> OTHER INFORMATION: Synthetic

<400> SEQUENCE: 15

Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
                20                  25                  30

Thr Arg Ala His Leu Leu Leu Lys Glu Lys Met Met Arg Leu Gly Gly
            35                  40                  45

```
Arg Leu Val Leu Asn Thr Lys Glu Glu Leu Ala Asn Glu Arg Leu Met
 50                  55                  60

Thr Leu Lys Ile Ala Glu Met Lys Glu Ala Met Arg Thr Leu Ile Phe
 65                  70                  75                  80

Pro Pro Ser Met His Phe Phe Gln Ala Lys His Leu Ile Glu Arg Ser
                 85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Gly Gln Gly Thr Ser Ile Asp
        355                 360                 365

Arg Asn Ile Leu Asp Ala Leu Met Leu Asn Thr Thr Arg Ile Gly His
370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Asp Pro Ala Met Phe Gly Ala
        435                 440                 445

Lys Gly Leu Ser Tyr Asp Phe Tyr Glu Val Phe Met Gly Ile Gly Gly
450                 455                 460

Met Lys Ala Asp Leu Arg Thr Leu Lys Gln Leu Ala Met Asn Ser Ile
```

Lys Tyr Ser Thr Leu Leu Glu Ser Glu Lys Asn Thr Phe Met Glu Ile
465                 470                 475                 480

Trp Lys Lys Arg Trp Asp Lys Phe Ile Ala Asp Val Ala Thr Lys
            485                 490                 495
        500                 505                 510

<210> SEQ ID NO 16
<211> LENGTH: 1536
<212> TYPE: DNA
<213> ORGANISM: Artificial Sequence
<220> FEATURE:
<223> OTHER INFORMATION: Synthetic

<400> SEQUENCE: 16

```
atgctggtcg acggcccttc agaacggcct gctctgtgct tcctgctgct ggctgtcgca      60
atgagcttct ttggtagtgc cctgtccatc gacgagaccc gggcccacct gctgctgaag     120
gagaagatga tgaggctggg cggcagactg gtgctgaaca ccaaggagga gctggctaat     180
gagcggctga tgacactgaa gatcgccgag atgaaggagg ctatgaggac cctgatcttc     240
ccccttcca tgcacttctt tcaagccaag cacctgattg agagatctca ggtgtttaac     300
atcctgcgga tgatgcccaa gggcgccgct ctgcacctgc acgacatcgg catcgtgacc     360
atggattggc tggtgcggaa tgtgacatac aggcctcact ccacatctg tttcacccca     420
cggggcatca tgcagttcag atttgcccac ccaacacccc ggccttctga agtgcagc      480
aagtggatcc tgctggagga ctaccggaag agggtgcaga acgtgaccga gttcgacgat     540
tccctgctgc ggaacttcac cctggtgaca cagcaccctg aagtgatcta caccaaccag     600
aatgtggtgt ggtctaagtt cgagaccatc ttctttacaa tcagcggcct gatccactac     660
gccccagtgt tcagagacta cgtgttccgg agcatgcagg agtttacga ggataacgtg      720
ctgtatatgg agatcagagc tcggctgctg cccgtgtacg agctgtccgg cgagcaccac     780
gatgaggagt ggtctgtgaa gacctaccag gaggtggccc agaagttcgt ggagacacac     840
cccgagttta tcggcatcaa gatcatctat tccgaccacc ggtctaagga tgtggccgtg     900
atcgctgaga gcatccggat ggccatgggc ctgaggatca agttccctac agtggtggct     960
ggctttgacc tggtcggcca cgaggataca ggccactccc tgcacgacta caaggaggcc    1020
ctgatgatcc ccgctaagga tggcgtgaag ctgccttatt tctttcacgc cggcgagacc    1080
gatggccagg gcacaagcat cgacaggaac atcctggatg ctctgatgct gaataccaca    1140
agaatcggcc acggcttcgc cctgagcaag caccctgctg tgcggaccta ctcctggaag    1200
aaggacatcc aatcgaggt gtgccccatc tctaaccaag tgctgaagct ggtgagcgat    1260
ctgcggaatc acccagtggc caccctgatg gctacaggcc acccaatggt catcagctcc    1320
gacgatcccg ccatgtttgg cgctaagggc ctgtcttacg acttctatga ggtgtttatg    1380
ggcatcggcg gcatgaaggc cgatctgcgg acccctgaagc agctggctat gaacagcatc    1440
aagtattcca cactgctgga gagcgagaag aatacattca tggaaatctg gaagaaacgg    1500
tgggacaagt tcatcgctga cgtggctact aaatga                              1536
```

<210> SEQ ID NO 17
<211> LENGTH: 511
<212> TYPE: PRT
<213> ORGANISM: Artificial Sequence
<220> FEATURE:
<223> OTHER INFORMATION: Synthetic

<400> SEQUENCE: 17

-continued

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu Gln
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
        355                 360                 365

Arg Asn Ile Leu Asp Ala Leu Met Leu Asn Thr Thr Arg Ile Gly His
    370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415
```

```
Leu Val Ser Asp Leu Arg Asn His Pro Val Ala Thr Leu Met Ala Thr
            420                 425                 430

Gly His Pro Met Val Ile Ser Ser Asp Asp Pro Ala Met Phe Gly Ala
            435                 440                 445

Lys Gly Leu Ser Tyr Asp Phe Tyr Glu Val Phe Met Gly Ile Gly Gly
            450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
            500                 505                 510
```

<210> SEQ ID NO 18
<211> LENGTH: 1536
<212> TYPE: DNA
<213> ORGANISM: Artificial Sequence
<220> FEATURE:
<223> OTHER INFORMATION: Synthetic

<400> SEQUENCE: 18

```
atgctggtcg acggcccttc agaacggcct gctctgtgct tcctgctgct ggctgtcgca    60
atgagcttct ttggtagtgc cctgtccatc gacgagaccc gggcccacct gctgctgaag   120
gagaagatga tgaggctggg cggcagactg gtgctgaaca ccaaggagga gctggctaat   180
gagcggctga tgacactgaa gatcgccgag atgaaggagg ctatgaggac cctgatcttc   240
cccccttcca tgcacttctt tcaagccaag cacctgattg agagatctca ggtgtttaac   300
atcctgcgga tgatgcccaa gggcgccgct ctgcaactgc acgacatcgg catcgtgacc   360
atggattggc tggtgcggaa tgtgacatac aggcctcact gccacatctg tttcacccca   420
cggggcatca tgcagttcag atttgcccac caacaccccc ggccttctga agtgcagc    480
aagtggatcc tgctggagga ctaccggaag agggtgcaga cgtgaccga gttcgacgat   540
tccctgctgc ggaacttcac cctggtgaca cagcaccctg aagtgatcta caccaaccag   600
aatgtggtgt ggtctaagtt cgagaccatc ttctttacaa tcagcggcct gatccactac   660
gccccagtgt tcagagacta cgtgttccgg agcatgcagg agttttacga ggataacgtg   720
ctgtatatgg agatcagagc tcggctgctg cccgtgtacg agctgtccgg cgagcaccac   780
gatgaggagt ggtctgtgaa gacctaccag gaggtggccc agaagttcgt ggagacacac   840
cccgagttta tcggcatcaa gatcatctat tccgaccacc ggtctaagga tgtggccgtg   900
atcgctgaga gcatccggat ggccatgggc ctgaggatca gttccctac agtggtggct   960
ggctttgacc tggtcggcca cgaggataca ggccactccc tgcacgacta caaggaggcc  1020
ctgatgatcc ccgctaagga tggcgtgaag ctgccttatt tctttcacgc cggcgagacc  1080
gattggcagg gcacaagcat cgacaggaac atcctggatg ctctgatgct gaataccaca  1140
agaatcggcc acggcttcgc cctgagcaag caccctgctg tgcggaccta ctcctggaag  1200
aaggacatcc aatcgaggt gtgccccatc tctaaccaag tgctgaagct ggtgagcgat  1260
ctgcggaatc acccagtggc caccctgatg gctacaggcc acccaatggt catcagctcc  1320
gacgatcccg ccatgtttgg cgctaagggc ctgtcttacg acttctatga ggtgtttatg  1380
ggcatcggcg gcatgaaggc cgatctgcgg accctgaagc agctggctat gaacagcatc  1440
aagtattcca cactgctgga gagcgagaag aatacattca tggaaatctg gaagaaacgg  1500
tgggacaagt tcatcgctga cgtggctact aaatga                             1536
```

```
<210> SEQ ID NO 19
<211> LENGTH: 743
<212> TYPE: PRT
<213> ORGANISM: Artificial Sequence
<220> FEATURE:
<223> OTHER INFORMATION: Synthetic

<400> SEQUENCE: 19

Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
                20                  25                  30

Thr Arg Ala His Leu Leu Lys Glu Lys Met Met Arg Leu Gly Gly
            35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
                100                 105                 110

Leu His Asp Ile Gly Ile Val Thr Met Asp Trp Leu Val Arg Asn Val
            115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
                180                 185                 190

Pro Glu Val Ile Tyr Thr Asn Gln Asn Val Val Trp Ser Lys Phe Glu
            195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
                260                 265                 270

Ala Gln Lys Phe Val Glu Thr His Pro Glu Phe Ile Gly Ile Lys Ile
            275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
                340                 345                 350

Tyr Phe Phe His Ala Gly Glu Thr Asp Trp Gln Gly Thr Ser Ile Asp
            355                 360                 365
```

Arg Asn Ile Leu Asp Ala Leu Met Leu Asn Thr Thr Arg Ile Gly His
    370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Pro Ala Met Phe Gly Ala
        435                 440                 445

Lys Gly Leu Ser Tyr Asp Phe Tyr Glu Val Phe Met Gly Ile Gly Gly
450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys Glu
                500                 505                 510

Pro Lys Ser Cys Asp Lys Thr His Thr Cys Pro Cys Pro Ala Pro
            515                 520                 525

Glu Leu Leu Gly Gly Pro Ser Val Phe Leu Phe Pro Pro Lys Pro Lys
530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
            580                 585                 590

Asn Ser Thr Tyr Arg Val Val Ser Val Leu Thr Val Leu His Gln Asp
        595                 600                 605

Trp Leu Asn Gly Lys Glu Tyr Lys Cys Lys Val Ser Asn Lys Ala Leu
610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Val Leu Asp Ser Asp Gly Ser Phe Phe Leu Tyr Ser
690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 20
<211> LENGTH: 2232
<212> TYPE: DNA
<213> ORGANISM: Artificial Sequence
<220> FEATURE:

<223> OTHER INFORMATION: Synthetic

<400> SEQUENCE: 20

```
atgttggtgg atggcccatc tgagcggcca gccctgtgct tcttgctgtt ggctgtggca        60
atgtctttct tcggctctgc tctatccata gatgaaacac gggcgcatct gttgttgaaa       120
gaaaagatga tgcggctggg ggggcggctg gtgctgaaca ccaaggagga gctggccaat       180
gagaggctca tgacgctcaa aatcgctgag atgaaggagg ccatgaggac cctgatattc       240
ccacccagca tgcactttt ccaggccaag catctcattg agagaagtca agtgtttaat        300
attctaagga tgatgccaaa aggggctgcc ttgcacctcc atgacattgg catcgtgact       360
atggactggc tggtgaggaa tgtcacctac aggcctcact gccacatctg tttcacccca       420
aggggggatca tgcagttcag atttgctcac ccaactcccc gtccatcaga aaaatgttcc      480
aagtggattc tgctggagga ttatcggaag cgggtgcaga acgtcactga gtttgatgac       540
agcttgctga ggaatttcac tctggtgacc cagcacccgg aggtgattta cacaaaccaa       600
aatgttgtct ggtcgaaatt tgaaaccatc ttcttcacca tctctggtct catccattac       660
gctccagtgt tcagagacta tgtcttccgg agcatgcagg agttctacga ggacaacgtg       720
ctctacatgg agatcagagc caggctgctg ccggtgtatg agctcagtgg agagcaccat       780
gacgaagagt ggtcagtgaa gacttatcag gaagtagctc agaagtttgt ggaaactcat       840
cctgagttta ttggaatcaa aatcattat tcggatcaca gatccaaaga tgtggctgtc        900
atcgcagaat ccatccgaat ggccatgggg ctccgaatca agttccccac ggtggtggca       960
gggtttgacc tggtggggca tgaggacact ggccactcct tgcatgacta caaggaagct      1020
ctgatgatcc ccgccaagga tggcgttaag ctgccttact tcttccacgc cggagaaaca      1080
gactggcagg gtacttccat agacaggaac attctggatg ctctgatgct gaacactacc      1140
agaatcggcc atggatttgc tttgagcaaa cacccgcag tcaggactta ttcctggaaa       1200
aaggacatcc ccatagaagt ctgtcccatc tctaaccagg tgctgaaact ggtgtctgac      1260
ttgaggaacc accctgtagc cactctgatg gccactgggc accccatggt gatcagctct      1320
gatgacccag ctatgtttgg tgccaaaggc ttgtcctatg atttctatga ggtcttcatg      1380
ggcattgggg ggatgaaggc tgatctgagg accctcaaac agctggccat gaactctatc      1440
aagtacagta ccctgttgga gagtgagaaa atactttca tggaaatatg gaagaagaga        1500
tgggataagt tcatagcaga tgtggctaca aaggagccca atcttgtga caaaactcac        1560
acatgcccac cgtgcccagc acctgaactc ctggggggac cgtcagtctt cctcttcccc      1620
ccaaaaccca aggacaccct catgatctcc cggacccctg aggtcacatg cgtggtggtg      1680
gacgtgagcc acgaagaccc tgaggtcaag ttcaactggt acgtggacgg cgtggaggtg      1740
cataatgcca agacaaagcc gcgggaggag cagtacaaca gcacgtaccg tgtggtcagc      1800
gtcctcaccg tcctgcacca ggactggctg aatggcaagg agtacaagtg caaggtctcc      1860
aacaaagccc tcccagcccc catcgagaaa accatctcca agccaaagg gcagccccga       1920
gaaccacagg tgtacaccct gcccccatcc cgggaggaga tgaccaagaa ccaggtcagc      1980
ctgacctgcc tggtcaaagg cttctatccc agcgacatcg ccgtggagtg ggagagcaat      2040
gggcagccgg agaacaacta caagaccacg cctcccgtgc tggactccga cggctccttc      2100
ttcctctaca gcaagctcac cgtggacaag agcaggtggc agcaggggaa cgtcttctca      2160
tgctccgtga tgcatgaggc tctgcacaac cactacacgc agaagagcct ctccctgtcc      2220
ccgggtaaat ga                                                          2232
```

```
<210> SEQ ID NO 21
<211> LENGTH: 743
<212> TYPE: PRT
<213> ORGANISM: Artificial Sequence
<220> FEATURE:
<223> OTHER INFORMATION: Synthetic

<400> SEQUENCE: 21
```

| | | | | | | | | | | | | | | | |
|---|---|---|---|---|---|---|---|---|---|---|---|---|---|---|---|
| Met | Leu | Val | Asp | Gly | Pro | Ser | Glu | Arg | Pro | Ala | Leu | Cys | Phe | Leu | Leu |
| 1 | | | | 5 | | | | | 10 | | | | | 15 | |
| Leu | Ala | Val | Ala | Met | Ser | Phe | Phe | Gly | Ser | Ala | Leu | Ser | Ile | Asp | Glu |
| | | | 20 | | | | | 25 | | | | | 30 | | |
| Thr | Arg | Ala | His | Leu | Leu | Lys | Glu | Lys | Met | Met | Arg | Leu | Gly | Gly | |
| | | 35 | | | | | 40 | | | | | 45 | | | |
| Arg | Leu | Val | Leu | Asn | Thr | Lys | Glu | Glu | Leu | Ala | Asn | Glu | Arg | Leu | Met |
| | 50 | | | | | 55 | | | | | 60 | | | | |
| Thr | Leu | Lys | Ile | Ala | Glu | Met | Lys | Glu | Ala | Met | Arg | Thr | Leu | Ile | Phe |
| 65 | | | | | 70 | | | | | 75 | | | | | 80 |
| Pro | Pro | Ser | Met | His | Phe | Phe | Gln | Ala | Lys | His | Leu | Ile | Glu | Arg | Ser |
| | | | | 85 | | | | | 90 | | | | | 95 | |
| Gln | Val | Phe | Asn | Ile | Leu | Arg | Met | Met | Pro | Lys | Gly | Ala | Ala | Leu | His |
| | | | 100 | | | | | 105 | | | | | 110 | | |
| Leu | His | Asp | Ile | Gly | Ile | Val | Thr | Met | Asp | Trp | Leu | Val | Arg | Asn | Val |
| | | | | 115 | | | | | 120 | | | | | 125 | |
| Thr | Tyr | Arg | Pro | His | Cys | His | Ile | Cys | Phe | Thr | Pro | Arg | Gly | Ile | Met |
| | | | 130 | | | | | 135 | | | | | 140 | | |
| Gln | Phe | Arg | Phe | Ala | His | Pro | Thr | Pro | Arg | Pro | Ser | Glu | Lys | Cys | Ser |
| 145 | | | | | 150 | | | | | 155 | | | | | 160 |
| Lys | Trp | Ile | Leu | Leu | Glu | Asp | Tyr | Arg | Lys | Arg | Val | Gln | Asn | Val | Thr |
| | | | | 165 | | | | | 170 | | | | | 175 | |
| Glu | Phe | Asp | Asp | Ser | Leu | Leu | Arg | Asn | Phe | Thr | Leu | Val | Thr | Gln | His |
| | | | 180 | | | | | 185 | | | | | 190 | | |
| Pro | Glu | Val | Ile | Tyr | Thr | Asn | Gln | Asn | Val | Val | Trp | Ser | Lys | Phe | Glu |
| | | | | 195 | | | | | 200 | | | | | 205 | |
| Thr | Ile | Phe | Phe | Thr | Ile | Ser | Gly | Leu | Ile | His | Tyr | Ala | Pro | Val | Phe |
| | | | 210 | | | | | 215 | | | | | 220 | | |
| Arg | Asp | Tyr | Val | Phe | Arg | Ser | Met | Gln | Glu | Phe | Tyr | Glu | Asp | Asn | Val |
| 225 | | | | | 230 | | | | | 235 | | | | | 240 |
| Leu | Tyr | Met | Glu | Ile | Arg | Ala | Arg | Leu | Leu | Pro | Val | Tyr | Glu | Leu | Ser |
| | | | | 245 | | | | | 250 | | | | | 255 | |
| Gly | Glu | His | His | Asp | Glu | Glu | Trp | Ser | Val | Lys | Thr | Tyr | Gln | Glu | Val |
| | | | 260 | | | | | 265 | | | | | 270 | | |
| Ala | Gln | Lys | Phe | Val | Glu | Thr | His | Pro | Glu | Phe | Ile | Gly | Ile | Lys | Ile |
| | | | | 275 | | | | | 280 | | | | | 285 | |
| Ile | Tyr | Ser | Asp | His | Arg | Ser | Lys | Asp | Val | Ala | Val | Ile | Ala | Glu | Ser |
| | | | 290 | | | | | 295 | | | | | 300 | | |
| Ile | Arg | Met | Ala | Met | Gly | Leu | Arg | Ile | Lys | Phe | Pro | Thr | Val | Val | Ala |
| 305 | | | | | 310 | | | | | 315 | | | | | 320 |
| Gly | Phe | Asp | Leu | Val | Gly | His | Glu | Asp | Thr | Gly | His | Ser | Leu | His | Asp |
| | | | | 325 | | | | | 330 | | | | | 335 | |
| Tyr | Lys | Glu | Ala | Leu | Met | Ile | Pro | Ala | Lys | Asp | Gly | Val | Lys | Leu | Pro |
| | | | 340 | | | | | 345 | | | | | 350 | | |
| Tyr | Phe | Phe | His | Ala | Gly | Glu | Thr | Asp | Trp | Gln | Gly | Thr | Ser | Ile | Asp |
| | | | | 355 | | | | | 360 | | | | | 365 | |

Arg Asn Ile Leu Asp Ala Leu Met Leu Asn Thr Thr Arg Ile Gly His
    370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Pro Ala Met Phe Gly Ala
        435                 440                 445

Lys Gly Leu Ser Tyr Asp Phe Tyr Glu Val Phe Met Gly Ile Gly Gly
450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys Glu
            500                 505                 510

Pro Lys Ser Ser Asp Lys Thr His Thr Cys Pro Pro Cys Pro Ala Pro
        515                 520                 525

Glu Ala Ala Gly Gly Ser Ser Val Phe Leu Phe Pro Pro Lys Pro Lys
530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
            580                 585                 590

Asn Ser Thr Tyr Arg Val Val Ser Val Leu Thr Val Leu His Gln Asp
        595                 600                 605

Trp Leu Asn Gly Lys Glu Tyr Lys Cys Lys Val Ser Asn Lys Ala Leu
610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Val Leu Asp Ser Asp Gly Ser Phe Phe Leu Tyr Ser
690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 22
<211> LENGTH: 2232
<212> TYPE: DNA
<213> ORGANISM: Artificial Sequence
<220> FEATURE:

<223> OTHER INFORMATION: Synthetic

<400> SEQUENCE: 22

```
atgttggtgg atggcccatc tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa aatcgctgag atgaaggagg ccatgaggac cctgatattc     240
ccacccagca tgcactttt tccaggccaag catctcattg agagaagtca agtgtttaat     300
attctaagga tgatgccaaa aggggctgcc ttgcacctcc atgacattgg catcgtgact     360
atggactggc tggtgaggaa tgtcacctac aggcctcact gccacatctg tttcacccca     420
agggggatca tgcagttcag atttgctcac ccaactcccc gtccatcaga aaaatgttcc     480
aagtggattc tgctggagga ttatcggaag cgggtgcaga acgtcactga gtttgatgac     540
agcttgctga ggaatttcac tctggtgacc cagcacccgg aggtgattta cacaaaccaa     600
aatgttgtct ggtcgaaatt tgaaaccatc ttcttcacca tctctggtct catccattac     660
gctccagtgt tcagagacta tgtcttccgg agcatgcagg agttctacga ggacaacgtg     720
ctctacatgg agatcagagc caggctgctg ccggtgtatg agctcagtgg agagcaccat     780
gacgaagagt ggtcagtgaa gacttatcag gaagtagctc agaagtttgt ggaaactcat     840
cctgagttta ttggaatcaa aatcatttat tcggatcaca gatccaaaga tgtggctgtc     900
atcgcagaat ccatccgaat ggccatgggg ctccgaatca agttccccac ggtggtggca     960
gggtttgacc tggtggggca tgaggacact ggccactcct tgcatgacta caaggaagct    1020
ctgatgatcc ccgccaagga tggcgttaag ctgccttact tcttccacgc cggagaaaca    1080
gactggcagg gtacttccat agacaggaac attctggatg ctctgatgct gaacactacc    1140
agaatcggcc atggatttgc tttgagcaaa caccccgcag tcaggactta ttcctggaaa    1200
aaggacatcc cctagaagt ctgtcccatc tctaaccagg tgctgaaact ggtgtctgac    1260
ttgaggaacc accctgtagc cactctgatg gccactgggc accccatggt gatcagctct    1320
gatgacccag ctatgtttgg tgccaaaggc ttgtcctatg atttctatga ggtcttcatg    1380
ggcattgggg ggatgaaggc tgatctgagg accctcaaac agctggccat gaactctatc    1440
aagtacagta ccctgttgga gagtgagaaa aatactttca tggaaatatg aagaagaga    1500
tgggataagt tcatagcaga tgtggctaca aaggagccca atcctccga caagacacac    1560
acatgtcctc cctgtcccgc tcctgaagct gccggaggat ccagcgtgtt tctcttccct    1620
cctaagccca aggacaccct catgatcagc agaaccccg aagtcacctg cgtcgtggtc    1680
gacgtctccc acgaggaccc cgaagtgaag ttcaactggt acgtgacgg agtcgaggtc    1740
cacaacgcca agaccaagcc cagggaggag cagtacaaca gcacatacag ggtggtgagc    1800
gtcctcaccg tcctccatca ggactggctg aacggcaagg agtacaaatg caaggtgagc    1860
aataaggccc tccctgcccc catcgaaaag accatctcca aagccaaggg ccaacctaga    1920
gaaccccagg tctataccct ccctccctcc agagacgagc tcacaaagaa ccaggtcagc    1980
ctgacctgtc tggtgaaggg attctaccct tccgacattg ccgtcgagtg ggagtccaat    2040
ggccagcccg agaacaatta caagaccaca ccccctgtcc tcgactccga cggctccttc    2100
ttcctgtact ccaagctgac cgtcgacaag tccaggtggc aacagggcaa cgtcttcagc    2160
tgctccgtca tgcatgaggc cctccacaac cactacacac agaagtccct ctccctgagc    2220
cccggcaagt ga                                                         2232
```

<210> SEQ ID NO 23
<211> LENGTH: 567
<212> TYPE: PRT
<213> ORGANISM: Artificial Sequence
<220> FEATURE:
<223> OTHER INFORMATION: Synthetic

<400> SEQUENCE: 23

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
                100                 105                 110

Leu His Asp Ile Gly Ile Val Thr Met Asp Trp Leu Val Arg Asn Val
            115                 120                 125

Thr Tyr Arg Pro His Cys His Ile Cys Phe Thr Pro Arg Gly Ile Met
        130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                325                 330                 335

Tyr Lys Glu Ala Leu Met Ile Pro Ala Lys Asp Gly Val Lys Leu Pro
            340                 345                 350

Tyr Phe Phe His Ala Gly Glu Thr Asp Trp Gln Gly Thr Ser Ile Asp
        355                 360                 365
```

Arg Asn Ile Leu Asp Ala Leu Met Leu Asn Thr Thr Arg Ile Gly His
    370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
                420                 425                 430

Gly His Pro Met Val Ile Ser Ser Asp Pro Ala Met Phe Gly Ala
                435                 440                 445

Lys Gly Leu Ser Tyr Asp Phe Tyr Glu Val Phe Met Gly Ile Gly Gly
    450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys Ser
                500                 505                 510

Ser Ser Ser Lys Ala Pro Pro Ser Leu Pro Ser Pro Ser Arg Leu
    515                 520                 525

Pro Gly Pro Ser Asp Thr Pro Ile Leu Pro Gln Ser Ser Ser Ser Lys
530                 535                 540

Ala Pro Pro Pro Ser Leu Pro Ser Pro Ser Arg Leu Pro Gly Pro Ser
545                 550                 555                 560

Asp Thr Pro Ile Leu Pro Gln
                565

<210> SEQ ID NO 24
<211> LENGTH: 1704
<212> TYPE: DNA
<213> ORGANISM: Artificial Sequence
<220> FEATURE:
<223> OTHER INFORMATION: Synthetic

<400> SEQUENCE: 24

```
atgttggtgg atggcccatc tgagcggcca gccctgtgct tcttgctgtt ggctgtggca        60
atgtctttct tcggctctgc tctatccata gatgaaacac gggcgcatct gttgttgaaa       120
gaaaagatga tgcggctggg ggggcggctg gtgctgaaca ccaaggagga gctggccaat       180
gagaggctca tgacgctcaa atcgctgag atgaaggagg ccatgaggac cctgatattc        240
ccacccagca tgcactttt ccaggccaag catctcattg agagaagtca gtgtttaat        300 attctaagga tgatgccaaa agggctgcc ttgcacctcc atgacattgg catcgtgact        360
atggactggc tggtgaggaa tgtcacctac aggcctcact gccacatctg tttcacccca       420 aggggggatca tgcagttcag atttgctcac ccaactcccc gtccatcaga aaaatgttcc      480
aagtggattc tgctggagga ttatcggaag cgggtgcaga cgtcactga gtttgatgac        540 agcttgctga ggaatttcac tctggtgacc cagcacccgg aggtgattta cacaaaccaa       600
aatgttgtct ggtcgaaatt tgaaaccatc ttcttcacca tctctggtct catccattac       660
gctccagtgt tcagagacta tgtcttccgg agcatgcagg agttctacga ggacaacgtg       720
ctctacatgg agatcagagc caggctgctg ccggtgtatg agctcagtgg agagcaccat       780
gacgaagagt ggtcagtgaa gacttatcag gaagtagctc agaagtttgt ggaaactcat       840
cctgagttta ttggaatcaa aatcattat tcggatcaca gatccaaaga tgtggctgtc       900
```

```
atcgcagaat ccatccgaat ggccatgggg ctccgaatca agttccccac ggtggtggca      960
gggtttgacc tggtgggca tgaggacact ggccactcct tgcatgacta caaggaagct     1020
ctgatgatcc ccgccaagga tggcgttaag ctgccttact tcttccacgc cggagaaaca     1080
gactggcagg gtacttccat agacaggaac attctggatg ctctgatgct gaacactacc     1140
agaatcggcc atggatttgc tttgagcaaa cacccgcag tcaggactta ttcctggaaa      1200
aaggacatcc ccatagaagt ctgtcccatc tctaaccagg tgctgaaact ggtgtctgac     1260
ttgaggaacc accctgtagc cactctgatg gccactgggc accccatggt gatcagctct     1320
gatgacccag ctatgtttgg tgccaaaggc ttgtcctatg atttctatga ggtcttcatg     1380
ggcattgggg ggatgaaggc tgatctgagg accctcaaac agctggccat gaactctatc     1440
aagtacagta ccctgttgga gagtgagaaa aatactttca tggaaatatg aagaagaga     1500
tgggataagt tcatagcaga tgtggctaca aagtcctctt cctcaaaggc acctccacct     1560
agccttccaa gtccatcccg actcccgggg ccctcggaca cccgatcct cccacaatct     1620
tcctcttcca aagctccccc tccatccta ccttctcctt cgcgtctccc tggtccttcc     1680
gatacaccaa ttctaccca gtga                                            1704
```

<210> SEQ ID NO 25
<211> LENGTH: 743
<212> TYPE: PRT
<213> ORGANISM: Artificial Sequence
<220> FEATURE:
<223> OTHER INFORMATION: Synthetic

<400> SEQUENCE: 25

```
Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
```

```
            210                 215                 220
Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                    245                 250                 255

Gly Glu His His Asp Glu Glu Trp Ser Val Lys Thr Tyr Gln Glu Val
                260                 265                 270

Ala Gln Lys Phe Val Glu Thr His Pro Glu Phe Ile Gly Ile Lys Ile
            275                 280                 285

Ile Tyr Ser Asp His Arg Ser Lys Asp Val Ala Val Ile Ala Glu Ser
        290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
                    325                 330                 335

Tyr Lys Glu Ala Leu Met Ile Pro Ala Lys Asp Gly Val Lys Leu Pro
                340                 345                 350

Tyr Phe Phe His Ala Gly Glu Thr Asp Trp Gln Gly Thr Ser Ile Asp
            355                 360                 365

Arg Asn Ile Leu Asp Ala Leu Met Leu Asn Thr Thr Arg Ile Gly His
370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                    405                 410                 415

Leu Val Ser Asp Leu Arg Asn His Pro Val Ala Thr Leu Met Ala Thr
                420                 425                 430

Gly His Pro Met Val Ile Ser Ser Asp Asp Pro Ala Met Phe Gly Ala
            435                 440                 445

Lys Gly Leu Ser Tyr Asp Phe Tyr Glu Val Phe Met Gly Ile Gly Gly
        450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                    485                 490                 495

Trp Lys Lys Arg Trp Asp Lys Phe Ile Ala Asp Val Ala Thr Lys Glu
                500                 505                 510

Pro Lys Ser Ser Asp Lys Thr His Thr Ser Pro Pro Ser Pro Ala Pro
            515                 520                 525

Glu Leu Leu Gly Gly Ser Ser Val Phe Leu Phe Pro Pro Lys Pro Lys
        530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                    565                 570                 575

Gly Val Glu Val His Asn Ala Lys Thr Lys Pro Arg Glu Glu Gln Tyr
                580                 585                 590

Asn Ser Thr Tyr Arg Val Val Ser Val Leu Thr Val Leu His Gln Asp
            595                 600                 605

Trp Leu Asn Gly Lys Glu Tyr Lys Cys Lys Val Ser Asn Lys Ala Leu
        610                 615                 620

Pro Ala Pro Ile Glu Lys Thr Ile Ser Lys Ala Lys Gly Gln Pro Arg
625                 630                 635                 640
```

```
Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Val Leu Asp Ser Asp Gly Ser Phe Phe Leu Tyr Ser
    690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740
```

<210> SEQ ID NO 26
<211> LENGTH: 2232
<212> TYPE: DNA
<213> ORGANISM: Artificial Sequence
<220> FEATURE:
<223> OTHER INFORMATION: Synthetic

<400> SEQUENCE: 26

```
atgttggtgg atggcccatc tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa atcgctgagt atgaaggagg ccatgaggac cctgatattc     240
ccacccagca tgcacttttt ccaggccaag catctcattg agagaagtca agtgtttaat     300
attctaagga tgatgccaaa aggggctgcc ttgcacctcc atgacattgg catcgtgact     360
atggactggc tggtgaggaa tgtcacctac aggcctcact gccacatctg tttcacccca     420
agggggatca tgcagttcag atttgctcac ccaactcccc gtccatcaga aaaatgttcc     480
aagtggattc tgctggagga ttatcggaag cgggtgcaga acgtcactga gtttgatgac     540
agcttgctga ggaatttcac tctggtgacc agcacccgg aggtgattta cacaaaccaa     600
aatgttgtct ggtcgaaatt tgaaaccatc ttcttcacca tctctggtct catccattac     660
gctccagtgt tcagagacta tgtcttccgg agcatgcagg agttctacga ggacaacgtg     720
ctctacatgg agatcagagc caggctgctg ccggtgtatg agctcagtgg agagcaccat     780
gacgaagagt ggtcagtgaa gacttatcag gaagtagctc agaagtttgt ggaaactcat     840
cctgagttta ttggaatcaa aatcatttat tcggatcaca gatccaaaga gtgtggctgtc    900 atcgcagaat ccatccgaat ggccatgggg ctccgaatca gttccccac ggtggtggca      960 gggtttgacc tggtggggca tgaggacact ggccactcct tgcatgacta caaggaagct    1020
ctgatgatcc ccgccaagga tggcgttaag ctgccttact tcttccacgc cggagaaaca    1080
gactggcagg gtacttccat agacaggaac attctggatg ctctgatgct gaacactacc    1140
agaatcggcc atggatttgc tttgagcaaa caccccgcag tcaggactta ttcctggaaa    1200
aaggacatcc ccatagaagt ctgtcccatc tctaaccagg tgctgaaact ggtgtctgac    1260
ttgaggaacc accctgtagc cactctgatg gccactgggc accccatggt gatcagctct    1320
gatgacccag ctatgtttgg tgccaaaggc ttgtcctatg atttctatga ggtcttcatg    1380
ggcattgggg ggatgaaggc tgatctgagg accctcaaac agctggccat gaactctatc    1440
```

-continued

```
aagtacagta ccctgttgga gagtgagaaa aatactttca tggaaatatg gaagaagaga    1500
tgggataagt tcatagcaga tgtggctaca aaggagccca atcttctga caaaactcac    1560 acatccccac cgtccccagc acctgaactc ctgggggggat cgtcagtctt cctcttcccc    1620
ccaaaaccca aggacaccct catgatctcc cggacccctg aggtcacatg cgtggtggtg    1680
gacgtgagcc acgaagaccc tgaggtcaag ttcaactggt acgtggacgg cgtggaggtg    1740
cataatgcca agacaaagcc gcgggaggag cagtacaaca gcacgtaccg tgtggtcagc    1800
gtcctcaccg tcctgcacca ggactggctg aatggcaagg agtacaagtg caaggtctcc    1860
aacaaagccc tcccagcccc catcgagaaa accatctcca aagccaaagg cagccccga    1920 gaaccacagg tgtacaccct gcccccatcc cgggatgagc tgaccaagaa ccaggtcagc    1980
ctgacctgcc tggtcaaagg cttctatccc agcgacatcg ccgtggagtg ggagagcaat    2040
gggcagccgg agaacaacta caagaccacg cctcccgtgc tggactccga cggctccttc    2100
ttcctctaca gcaagctcac cgtggacaag agcaggtggc agcaggggaa cgtcttctca    2160
tgctccgtga tgcatgaggc tctgcacaac cactacacgc agaagagcct ctccctgtcc    2220
ccgggtaaat ga                                                        2232
```

<210> SEQ ID NO 27
<211> LENGTH: 232
<212> TYPE: PRT
<213> ORGANISM: Artificial Sequence
<220> FEATURE:
<223> OTHER INFORMATION: Synthetic

<400> SEQUENCE: 27

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

Ser Leu Ser Leu Ser Pro Gly Lys
225                 230

<210> SEQ ID NO 28
<211> LENGTH: 232
<212> TYPE: PRT
<213> ORGANISM: Artificial Sequence
<220> FEATURE:
<223> OTHER INFORMATION: Synthetic

<400> SEQUENCE: 28

Glu Pro Lys Ser Ser Asp Lys Thr His Thr Cys Pro Pro Cys Pro Ala
1               5                   10                  15

Pro Glu Ala Ala Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 29
<211> LENGTH: 28
<212> TYPE: PRT
<213> ORGANISM: Artificial Sequence
<220> FEATURE:
<223> OTHER INFORMATION: Synthetic

<400> SEQUENCE: 29

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 30
<211> LENGTH: 56

```
<212> TYPE: PRT
<213> ORGANISM: Artificial Sequence
<220> FEATURE:
<223> OTHER INFORMATION: Synthetic

<400> SEQUENCE: 30

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln Ser Ser Ser
            20                  25                  30

Lys Ala Pro Pro Ser Leu Pro Ser Pro Ser Arg Leu Pro Gly Pro
        35                  40                  45

Ser Asp Thr Pro Ile Leu Pro Gln
    50                  55

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Gly Gly Gly Ser Gly Gly Gly Ala Ser
1               5

<210> SEQ ID NO 32
<211> LENGTH: 13
<212> TYPE: PRT
<213> ORGANISM: Artificial Sequence
<220> FEATURE:
<223> OTHER INFORMATION: Synthetic

<400> SEQUENCE: 32

Gly Gly Gly Ser Gly Gly Gly Ser Gly Gly Gly Ala Ser
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Synthetic

<400> SEQUENCE: 33

Ser His Gly Gly Gly Ser Gly Gly Gly Ser Gly Gly Gly Ser Gly Gly
1               5                   10                  15

Gly Ala Ser

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

Gly Gly Gly Ser Gly Gly Gly Ser Gly Gly Ser Gly Gly Gly Ala
1               5                   10                  15

Ser

<210> SEQ ID NO 35
<211> LENGTH: 5
<212> TYPE: PRT
```

<213> ORGANISM: Artificial Sequence
<220> FEATURE:
<223> OTHER INFORMATION: Synthetic

<400> SEQUENCE: 35

Gly Gly Gly Ala Ser
1               5

<210> SEQ ID NO 36
<211> LENGTH: 1536
<212> TYPE: DNA
<213> ORGANISM: Artificial Sequence
<220> FEATURE:
<223> OTHER INFORMATION: Synthetic

<400> SEQUENCE: 36

```
atgttggtgg atggcccatc tgagcggcca gccctgtgct tcttgctgtt ggctgtggca      60
atgtctttct tcggctctgc tctatccata gatgaaacac gggcgcatct gttgttgaaa     120
gaaaagatga tgcggctggg ggggcggctg gtgctgaaca ccaaggagga gctggccaat     180
gagaggctca tgacgctcaa atcgctgag atgaaggagg ccatgaggac cctgatattc      240
ccacccagca tgcactttt ccaggccaag catctcattg agaagtca agtgtttaat        300
attctaagga tgatgccaaa aggggctgcc ttgcacctcc atgacattgg catcgtgact     360
atggactggc tggtgaggaa tgtcacctac aggcctcact gccacatctg tttcacccca     420
agggggatca tgcagttcag atttgctcac ccaactcccc gtccatcaga aaatgttcc      480
aagtggattc tgctggagga ttatcggaag cgggtgcaga acgtcactga gtttgatgac     540
agcttgctga ggaatttcac tctggtgacc cagcacccgg aggtgattta cacaaaccaa     600
aatgttgtct ggtcgaaatt tgaaaccatc ttcttcacca tctctggtct catccattac     660
gctccagtgt tcagagacta tgtcttccgg agcatgcagg agttctacga ggacaacgtg     720
ctctacatgg agatcagagc caggctgctg ccggtgtatg agctcagtgg agagcaccat     780
gacgaagagt ggtcagtgaa gacttatcag gaagtagctc agaagtttgt ggaaactcat     840
cctgagttta ttggaatcaa aatcatttat tcggatcaca gatccaaaga tgtggctgtc     900
atcgcagaat ccatccgaat ggccatgggg ctccgaatca agttccccac ggtggtggca     960
gggtttgacc tggtggggca tgaggacact ggccactcct tgcatgacta caaggaagct    1020
ctgatgatcc ccgccaagga tggcgttaag ctgccttact tcttccacgc cggagaaaca    1080
gactggcagg gtacttccat agacaggaac attctggatg ctctgatgct gaacactacc    1140
agaatcggcc atggatttgc tttgagcaaa caccccgcag tcaggactta ttcctggaaa    1200
aaggacatcc ccatagaagt ctgtcccatc tctaaccagg tgctgaaact ggtgtctgac    1260
ttgaggaacc accctgtagc cactctgatg gccactgggc accccatggt gatcagctct    1320
gatgacccag ctatgtttgg tgccaaaggc ttgtcctatg atttctatga ggtcttcatg    1380
ggcattgggg ggatgaaggc tgatctgagg accctcaaac agctggccat gaactctatc    1440
aagtacagta ccctgttgga gagtgagaaa aatactttca tggaaatatg gaagaagaga    1500
tgggataagt tcatagcaga tgtggctaca aagtga                              1536
```

<210> SEQ ID NO 37
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 37
gggaaagauu auaaggaaau u                                             21

<210> SEQ ID NO 38
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 38
uuuccuuaua aucuuucccu u                                             21

<210> SEQ ID NO 39
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 39
ccauugagau gcagagaaau u                                             21

<210> SEQ ID NO 40
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 40
uuucucugca ucucaauggu u                                             21

<210> SEQ ID NO 41
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 41
aaauuaaacu gcaggguaau u                                             21

<210> SEQ ID NO 42
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphate on 5' end

<400> SEQUENCE: 42
uuacccugca guuuaauuuu u                                             21

<210> SEQ ID NO 43
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 43
cagcacaacu gcaggauaau u                                             21

```
<210> SEQ ID NO 44
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 44
uuauccugca guugugcugu u                                              21
```

UNITED STATES PATENT AND TRADEMARK OFFICE
CERTIFICATE OF CORRECTION

PATENT NO.         : 10,557,161 B2
APPLICATION NO.    : 15/527176
DATED              : February 11, 2020
INVENTOR(S)        : Anthony Quinn et al.

Page 1 of 1

It is certified that error appears in the above-identified patent and that said Letters Patent is hereby corrected as shown below:

In the Claims

At Column 152, Line 36, change "*nodosa*" to -- nodosa --

Signed and Sealed this
Thirty-first Day of March, 2020

Andrei Iancu
*Director of the United States Patent and Trademark Office*